(12) United States Patent
Que et al.

(10) Patent No.: US 8,916,567 B2
(45) Date of Patent: Dec. 23, 2014

(54) CERTAIN CRYSTALLINE HYDRATES, PHARMACEUTICAL COMPOSITIONS THEREOF AND METHODS FOR PREPARATION AND USE THEREOF

(75) Inventors: Feng Que, Atherton, CA (US); Ying Wang, Sichuan Province (CN)

(73) Assignee: Universal Technology Alliance, Inc., Atherton, CA (US)

( * ) Notice: Subject to any disclaimer, the term of this patent is extended or adjusted under 35 U.S.C. 154(b) by 673 days.

(21) Appl. No.: 12/938,555

(22) Filed: Nov. 3, 2010

(65) Prior Publication Data

US 2011/0136822 A1    Jun. 9, 2011

Related U.S. Application Data

(60) Provisional application No. 61/257,924, filed on Nov. 4, 2009.

(51) Int. Cl.
| | | |
|---|---|---|
| *A61K 31/497* | (2006.01) | |
| *C07D 413/10* | (2006.01) | |
| *A61P 31/04* | (2006.01) | |
| *C07D 263/22* | (2006.01) | |
| *A61K 31/496* | (2006.01) | |

(52) U.S. Cl.
CPC .......... *C07D 263/22* (2013.01); *A61K 31/496* (2013.01)
USPC .................................. 514/254.02; 544/369

(58) Field of Classification Search
CPC ........................... A61K 31/496; C07D 413/10
USPC .................................. 514/254.02; 544/369
See application file for complete search history.

(56) References Cited

U.S. PATENT DOCUMENTS

| | | | |
|---|---|---|---|
| 5,565,571 A | 10/1996 | Barbachyn et al. | |
| 5,846,514 A | 12/1998 | Foster et al. | |
| 6,334,997 B1 | 1/2002 | Foster et al. | |

FOREIGN PATENT DOCUMENTS

| | | | |
|---|---|---|---|
| CN | 1355165 | * | 12/2001 |
| CN | 1355165 | | 6/2002 |
| WO | WO 99/02525 | | 1/1999 |
| WO | WO 00/21960 | | 4/2000 |

OTHER PUBLICATIONS

Barbara Rodriguez-Spong, Christopher P. Price, Adivaraha Jayasankar, Adam J. Matzger, Nair Rodriguez-Hornedo, General principles of pharmaceutical solid polymorphism: a supramolecular perspective, Advanced Drug Delivery Reviews 56 (2004) 241-274.*
Yu et al., "Synthesis and antibacterial activity of linezolid analogues," Bioorganic & Medicinal Chemistry Letters, vol. 12 (6), pp. 857-859 (2002).
George W. Kabalka and Rajender S. Varma, *The Synthesis of Radiolabeled Compounds via Organometallic Intermediates*, Tetrahedron, 45 (21), pp. 6601-6621(1989).
E. Anthony Evans, *Synthesis of Radiolabeled Compounds*, Journal of Radioanalytical Chemistry, 64 (1-2), pp. 9-32 (1981).
International Search Report and Written Opinion from the Chinese Patent Office for International Application No. PCT/CN2010/078377, mailed Feb. 10, 2011.

\* cited by examiner

*Primary Examiner* — Sreeni Padmanabhan
*Assistant Examiner* — Jason A. Deck
(74) *Attorney, Agent, or Firm* — Finnegan, Henderson, Farabow, Garrett & Dunner LLP

(57) ABSTRACT

At least one crystalline hydrate of (S)—[N-3-(3'-fluoro-4'-(4"-phenyl piperazinyl))phenyl-2-oxo-5-oxazolidinyl]methyl acetamide, such as those with the following formula:

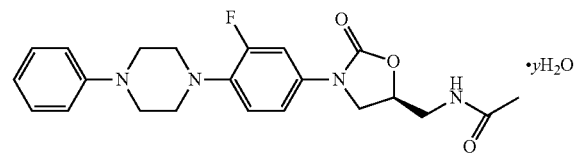

wherein y is a number ranging from 1/12 to 1. Also provided are methods for the preparation of such crystalline hydrates, pharmaceutical compositions comprising such crystalline hydrates, and methods for their uses.

50 Claims, 29 Drawing Sheets

CERTAIN CRYSTALLINE HYDRATES, PHARMACEUTICAL COMPOSITIONS THEREOF AND METHODS FOR PREPARATION AND USE THEREOF

This application claims the benefit of U.S. Provisional Patent Application No. 61/257,924, filed Nov. 4, 2009, entitled "CERTAIN CRYSTALLINE HEMI-HYDRATES, PHARMACEUTICAL COMPOSITIONS THEREOF AND METHODS FOR PREPARATION AND USE THEREOF."

Provided are certain crystalline hydrates of [N-3-(3'-fluoro-4'-(4"-phenyl piperazinyl))phenyl-2-oxo-5-oxazolidinyl]methyl acetamide, and particularly certain crystalline hydrates of (S)—[N-3-(3'-fluoro-4'-(4"-phenyl piperazinyl))phenyl-2-oxo-5-oxazolidinyl]methyl acetamide, pharmaceutical compositions thereof, and methods for the preparation and use thereof.

Currently, because of the limited number of effective antimicrobial agents, finding an effective treatment for infections caused by multiple-drug resistant gram positive bacterium is challenging. In addition, the drug resistant mechanisms of pathogenic bacterium are constantly evolving, increasing the difficulty of clinical treatment. Thus, there is a demand for effective antimicrobial agents.

Oxazolidinone antibiotics can exhibit a broad antibacterial spectrum against gram positive bacterium. For instance, some of the oxazolidinone antibiotics are known to have antibacterial activities against methicillin-resistant Staphylococci, vancomycin-resistant Staphylococci, vancomycin-resistant enterococci, penicillin-resistant pneumococci, and anaerobes.

Although certain oxazolidinone antibiotics may exhibit a high level of biological activity, their physicochemical properties may be less than ideal and their bioavailability may also be less than ideal. It may be possible to improve the physicochemical properties of oxazolidinone antibiotics by forming those compounds into salts. However, it can be rather challenging to develop a reliable process of forming, selecting, and characterizing a suitable salt for clinical application. For example, the conditions for forming the salt form of (S)—N-3-(3'-fluoro-4'-(4"-phenyl piperazinyl))phenyl-2-oxo-5-oxazolidinyl]methyl acetamide or crystalline hydrates thereof have yet to be found. And the overall properties of the salt form may be unpredictable.

The inventors have developed at least one new crystalline hydrate of (S)—N-3-(3'-fluoro-4'-(4"-phenyl piperazinyl))phenyl-2-oxo-5-oxazolidinyl]methyl acetamide. Those new hydrates can possess improved thermal stability and higher solubility compared to the anhydrous form of (S)—N-3-(3'-fluoro-4'-(4"-phenyl piperazinyl))phenyl-2-oxo-5-oxazolidinyl]methyl acetamide. Moreover, the disclosed crystalline hydrates can also have good bioavailability and drug efficacy, and can even be manufactured at a relatively low cost.

Thus, provided is at least one crystalline hydrate of (S)—[N-3-(3'-fluoro-4'-(4"-phenyl piperazinyl))phenyl-2-oxo-5-oxazolidinyl]methyl acetamide. Desirably, the at least one crystalline hydrate is at least 99% free of crystalline hydrates of (R)—[N-3-(3'-fluoro-4'-(4"-phenyl piperazinyl))phenyl-2-oxo-5-oxazolidinyl]methyl acetamide, the at least one crystalline hydrate can also be at least 95% free of crystalline hydrates of (R)—[N-3-(3'-fluoro-4'-(4"-phenyl piperazinyl))phenyl-2-oxo-5-oxazolidinyl]methyl acetamide, further the at least one crystalline hydrate can also be at least 90% free of crystalline hydrates of (R)—[N-3-(3'-fluoro-4'-(4"-phenyl piperazinyl))phenyl-2-oxo-5-oxazolidinyl]methyl acetamide, still further the at least one crystalline hydrate can be at least 80% free of crystalline hydrates of (R)—[N-3-(3'-fluoro-4'-(4"-phenyl piperazinyl))phenyl-2-oxo-5-oxazolidinyl]methyl acetamide, even further still the at least one crystalline hydrate can be at least 70% free of crystalline hydrates of (R)—[N-3-(3'-fluoro-4'-(4"-phenyl piperazinyl))phenyl-2-oxo-5-oxazolidinyl]methyl acetamide, and yet further still the at least one crystalline hydrate can be at least 60% free of crystalline hydrates of (R)—[N-3-(3'-fluoro-4'-(4"-phenyl piperazinyl))phenyl-2-oxo-5-oxazolidinyl]methyl acetamide, and even yet further still the at least one crystalline hydrate can be at least more than 50% free of crystalline hydrates of (R)—[N-3-(3'-fluoro-4'-(4"-phenyl piperazinyl))phenyl-2-oxo-5-oxazolidinyl]methyl acetamide.

Also provided are methods for the preparation of at least one crystalline (S)—[N-3-(3'-fluoro-4'-(4"-phenyl piperazinyl))phenyl-2-oxo-5-oxazolidinyl]methyl acetamide hydrate.

Also provided is a product of any of the methods described herein.

Also provided is a mixture comprising (S)—[N-3-(3'-fluoro-4'-(4"-phenyl piperazinyl))phenyl-2-oxo-5-oxazolidinyl]methyl acetamide and at least one crystalline hydrate of (S)—[N-3-(3'-fluoro-4'-(4"-phenyl piperazinyl))phenyl-2-oxo-5-oxazolidinyl]methyl acetamide, wherein the at least one crystalline hydrate is at least 90% free of crystalline hydrates of (R)—[N-3-(3'-fluoro-4'-(4"-phenyl piperazinyl))phenyl-2-oxo-5-oxazolidinyl]methyl acetamide.

Also provided is a pharmaceutical composition prepared by formulating a therapeutically effective amount of at least one crystalline hydrate described herein with one or more pharmaceutically acceptable diluents and/or excipients to provide the pharmaceutical composition.

Also provided is a method of treating a subject having a bacterial infection and in recognized need of said treatment comprising administering at least one crystalline hydrate described herein to said subject in need of said treatment.

Also provided is a method of treating a subject having a bacterial infection and in recognized need of said treatment comprising administering a pharmaceutical composition prepared by formulating a therapeutically effective amount of at least one crystalline hydrate described herein with one or more pharmaceutically acceptable diluents and/or excipients to provide the pharmaceutical composition.

BRIEF DESCRIPTION OF THE DRAWINGS

FIG. 3-1 is the close up of FIG. 3 at 3-5 ppm.

FIG. 3-2 is the close up of FIG. 3 at 6-9 ppm.

FIG. 4-1 is the close up of FIG. 4 at 100-140 ppm.

FIG. 10-1 is the close up of FIG. 10 at 3-5 ppm.

FIG. 10-2 is the close up of FIG. 10 at 6-9 ppm.

FIG. 11-1 is the close up of FIG. 11 at 100-140 ppm.

Figure 1:
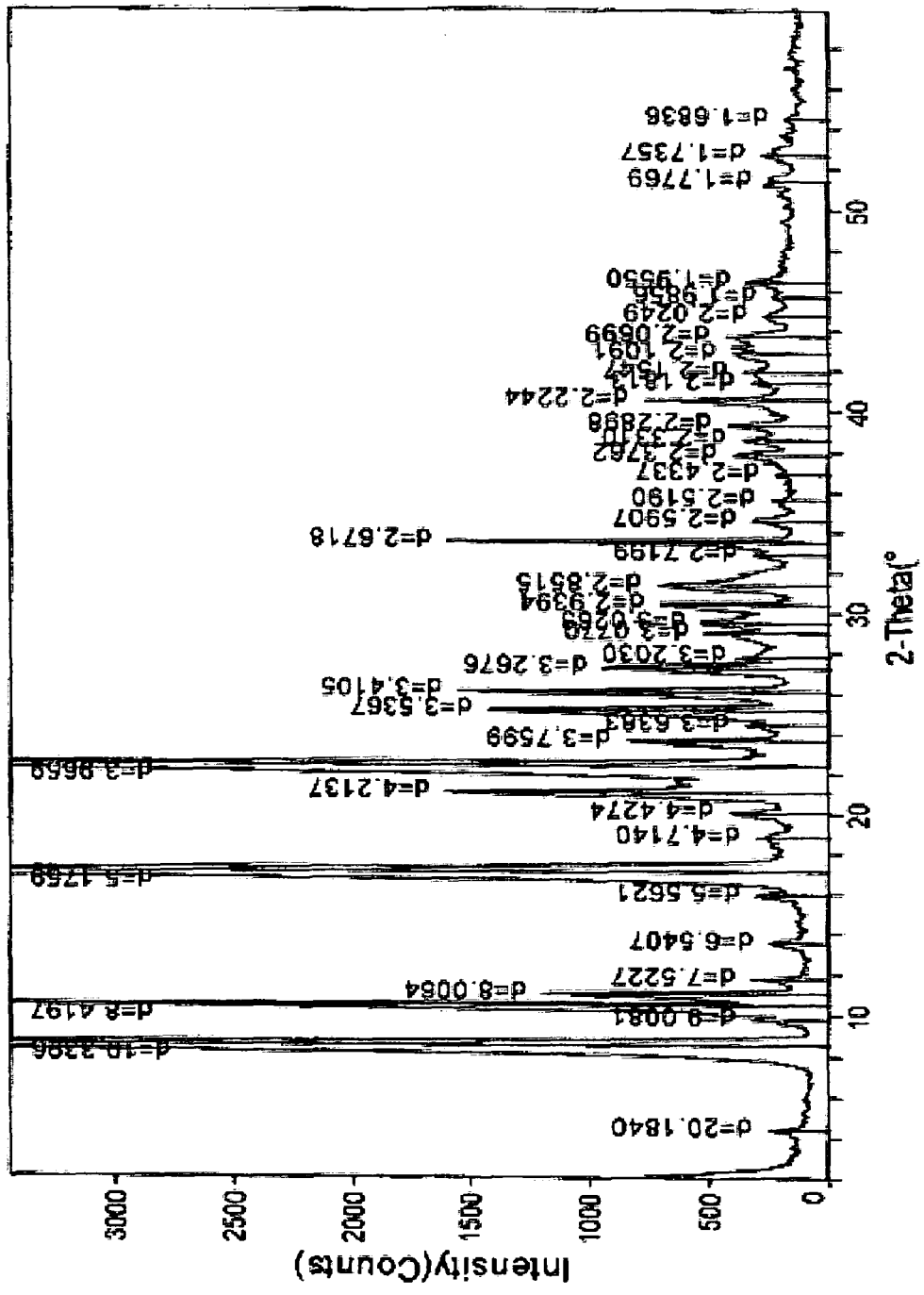
FIG. 1 is the X-ray diffractogram of (S)—[N-3-(3'-fluoro-4'-(4"-phenyl piperazinyl))phenyl-2-oxo-5-oxazolidinyl]methyl acetamide anhydride.
Figure 2:
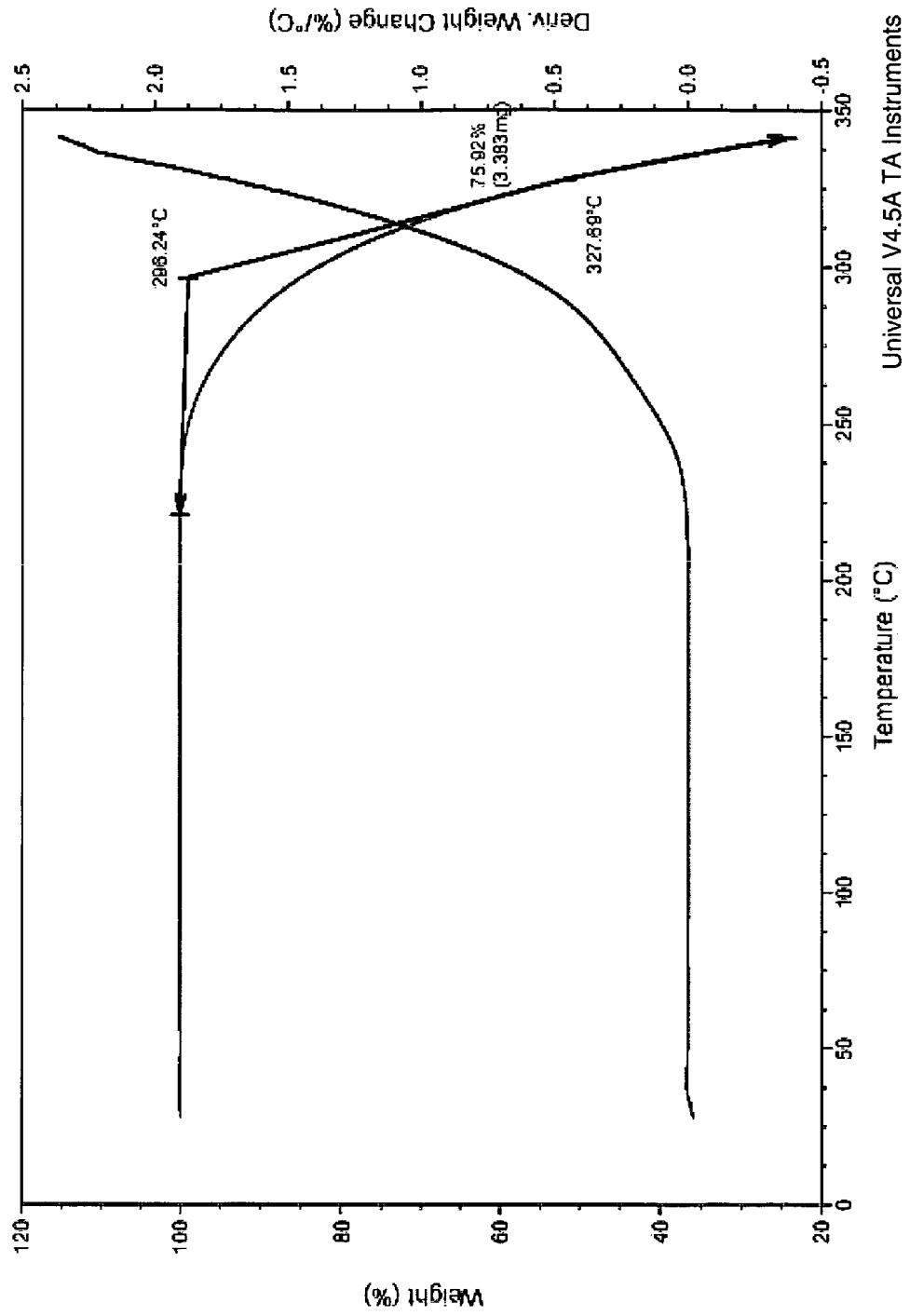
FIG. 2 is the TGA diagram of (S)—[N-3-(3'-fluoro-4'-(4"-phenyl piperazinyl))phenyl-2-oxo-5-oxazolidinyl]methyl acetamide anhydride.
Figure 3:
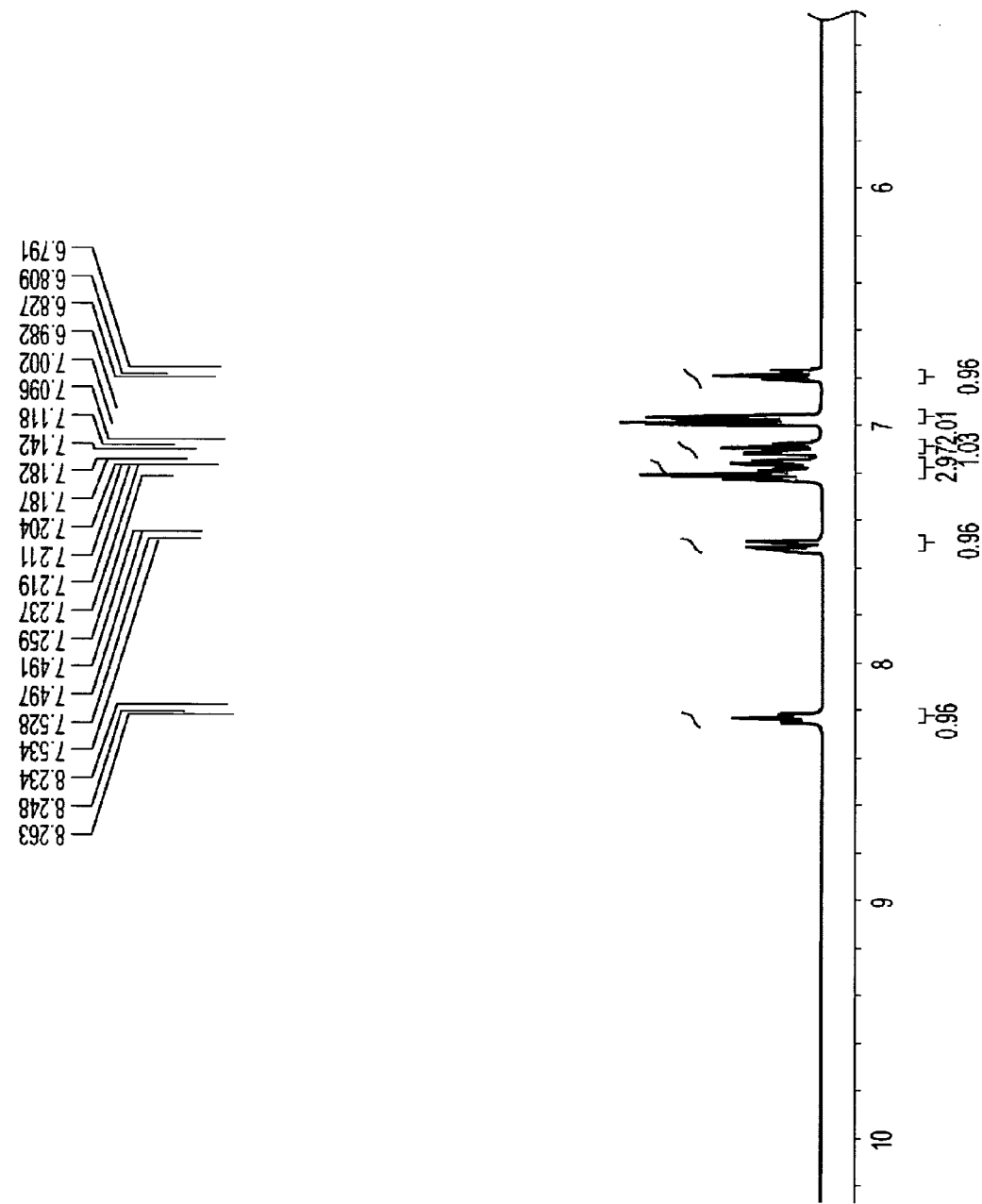
FIG. 3 is the $^1$H-NMR spectra of (S)—[N-3-(3'-fluoro-4'-(4"-phenyl piperazinyl))phenyl-2-oxo-5-oxazolidinyl]methyl acetamide anhydride.
Figure 3:
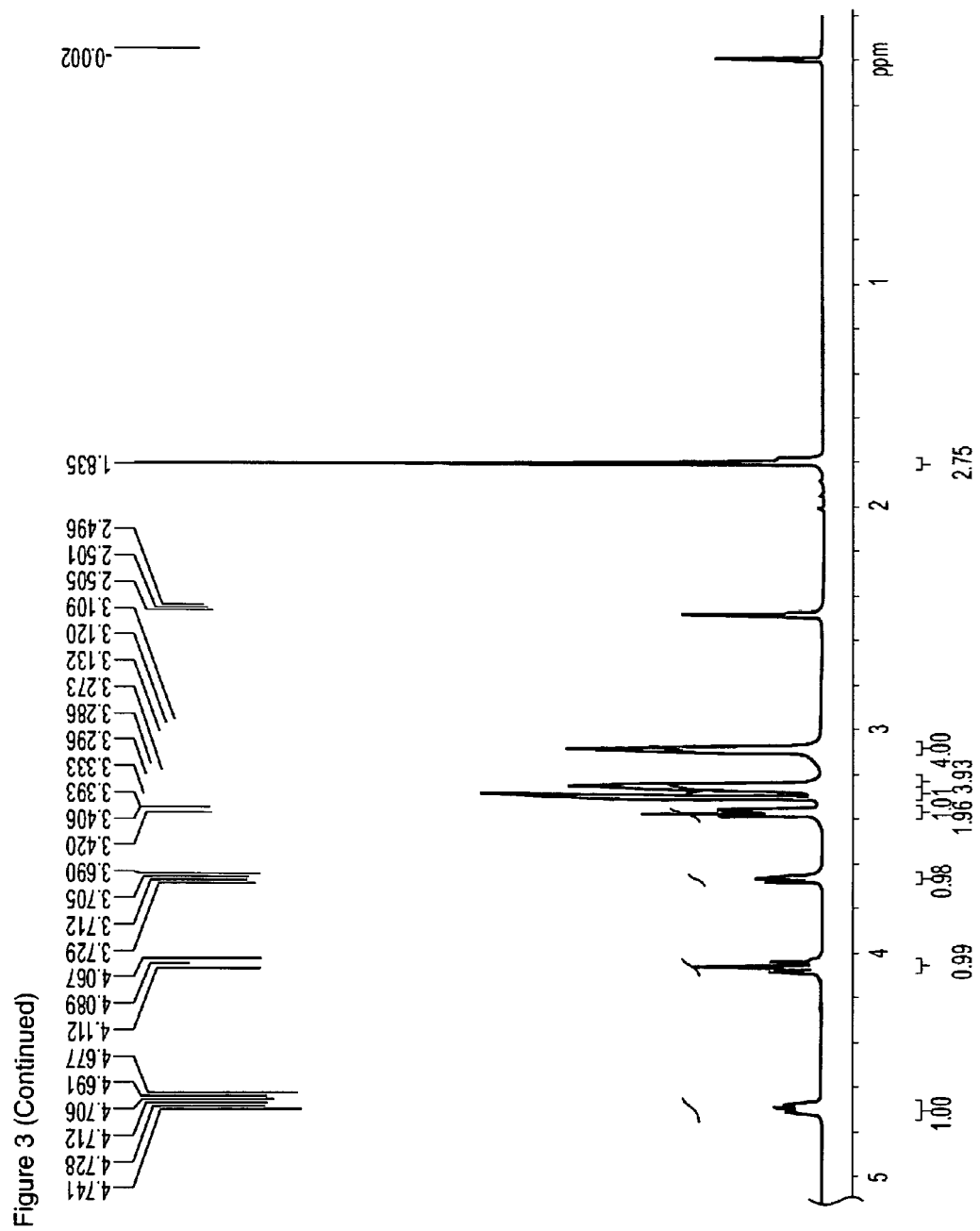
Figures 1, 3:
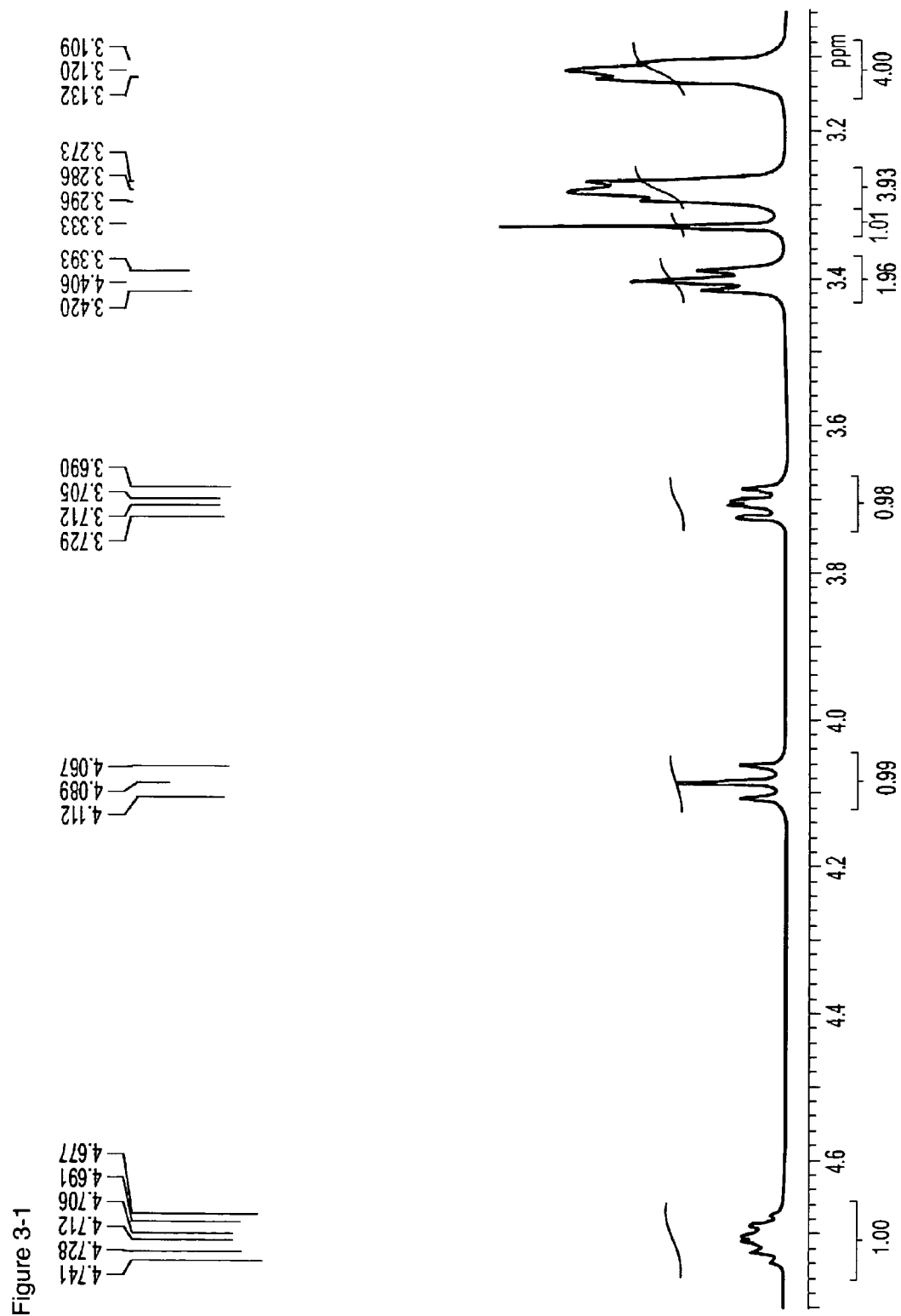
Figures 2, 3:
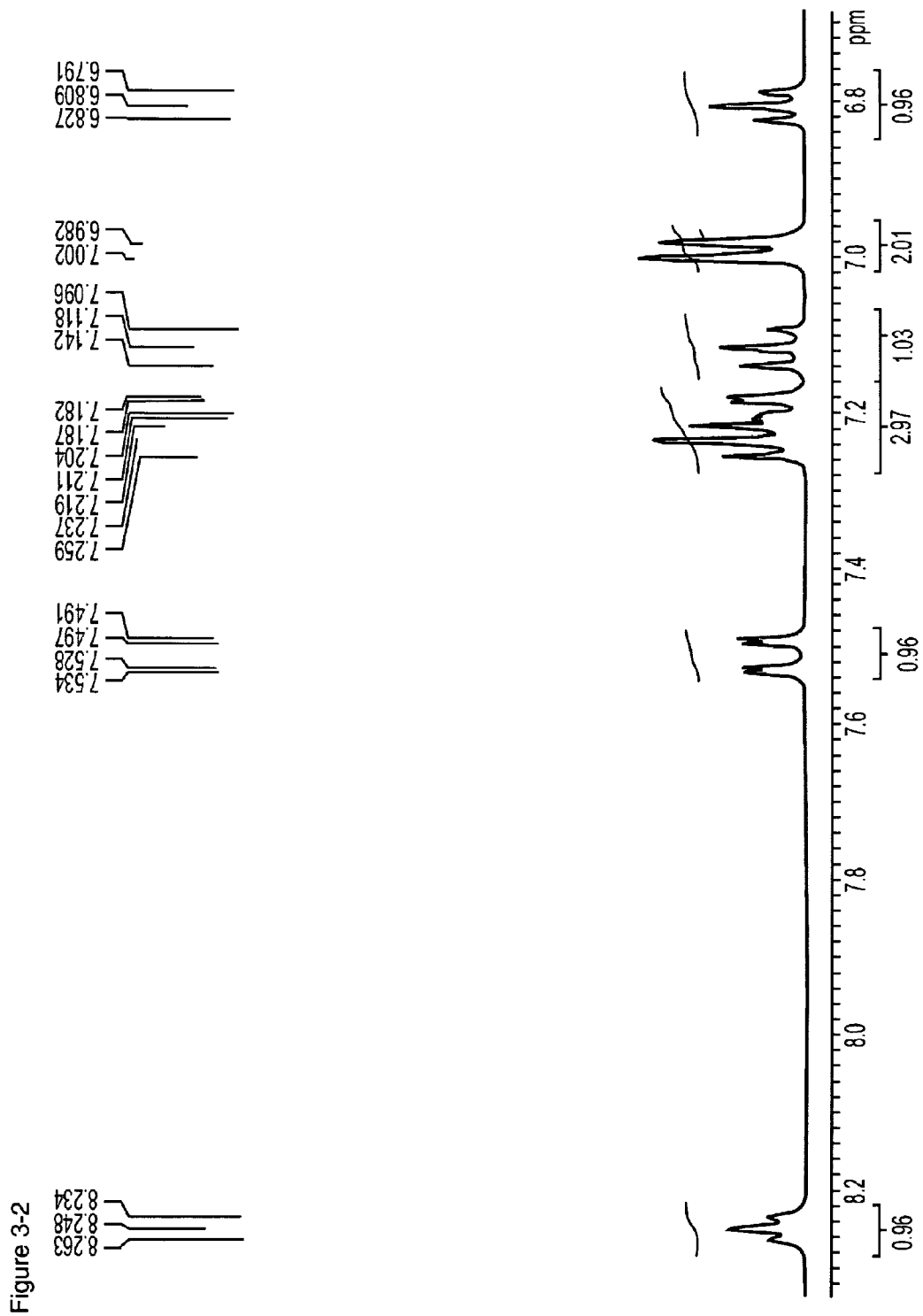
Figure 4:
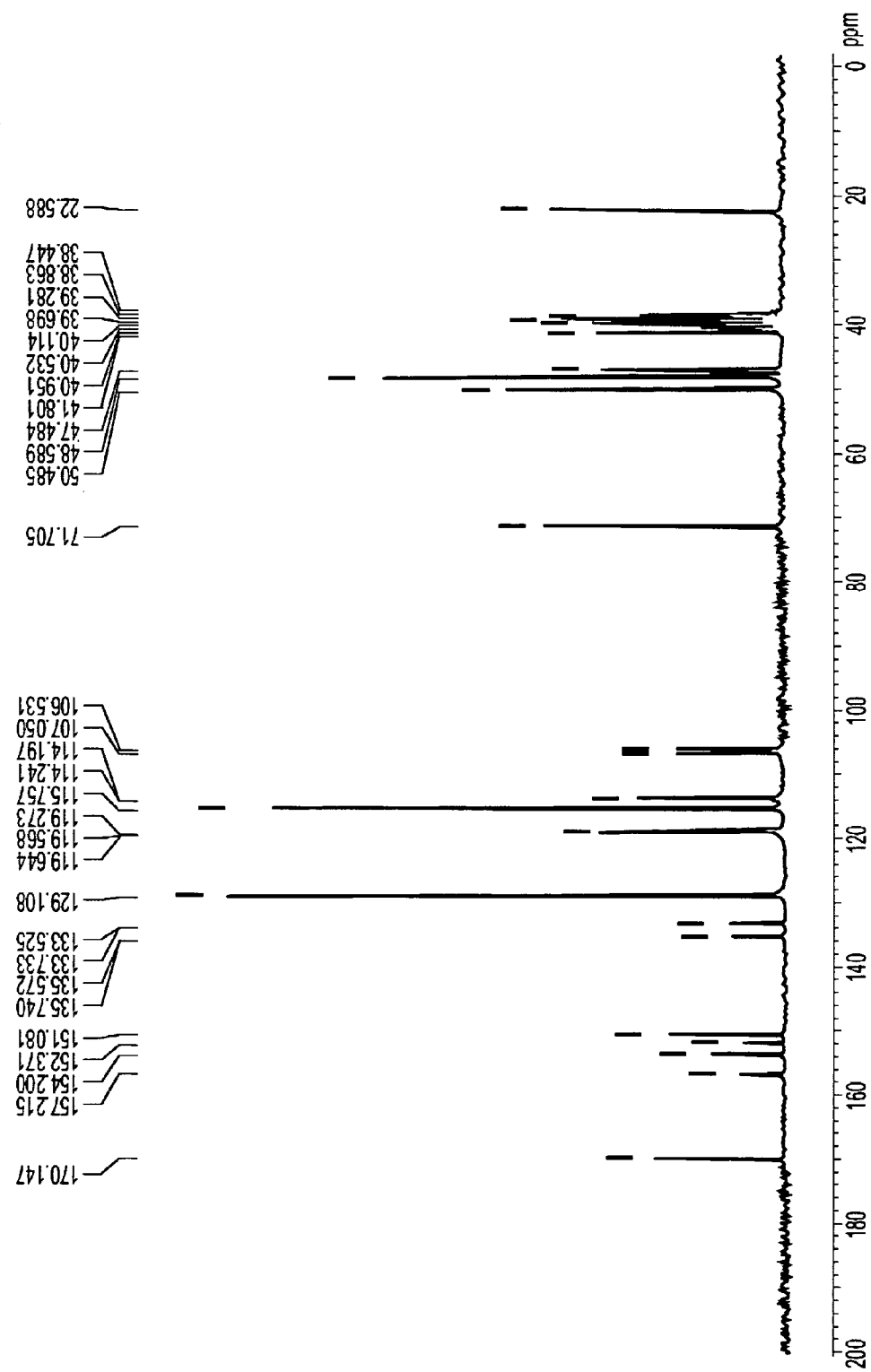
FIG. 4 is the $^{13}$C-NMR spectra of (S)—[N-3-(3'-fluoro-4'-(4"-phenyl piperazinyl))phenyl-2-oxo-5-oxazolidinyl]methyl acetamide anhydride.
Figures 1, 4:
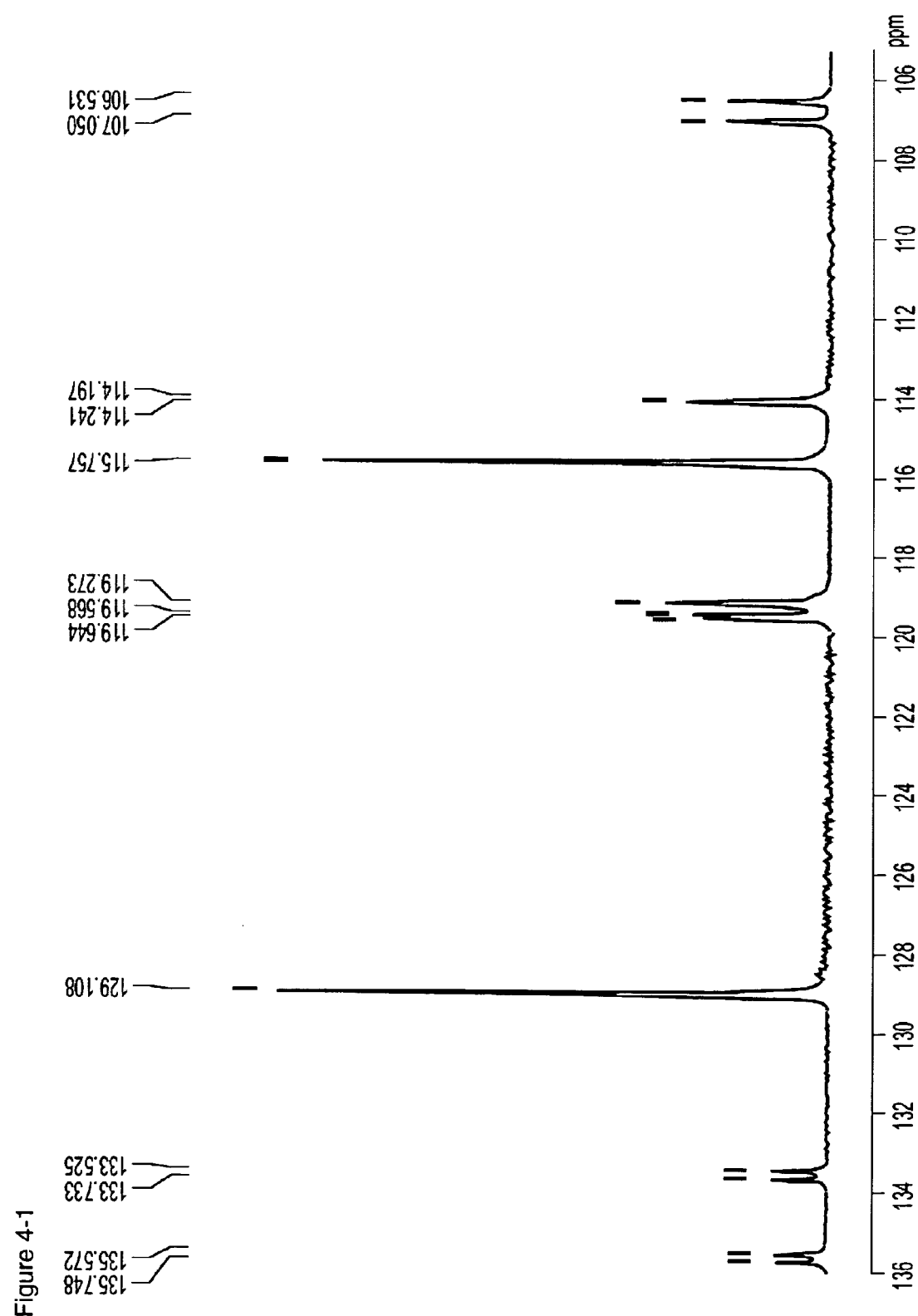
Figure 5:
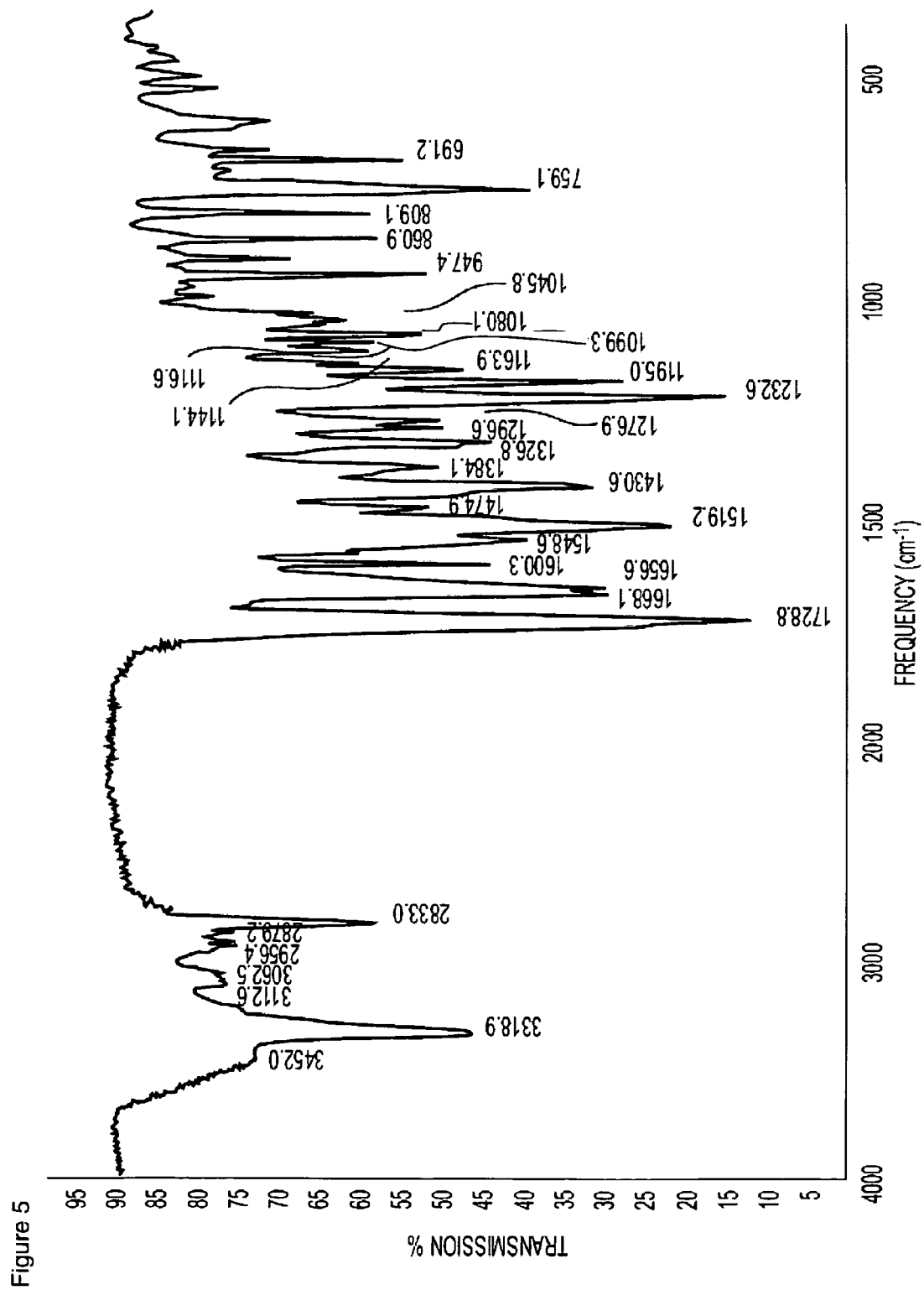
FIG. 5 is the IR spectra of (S)—[N-3-(3'-fluoro-4'-(4"-phenyl piperazinyl))phenyl-2-oxo-5-oxazolidinyl]methyl acetamide anhydride.
Figure 6:
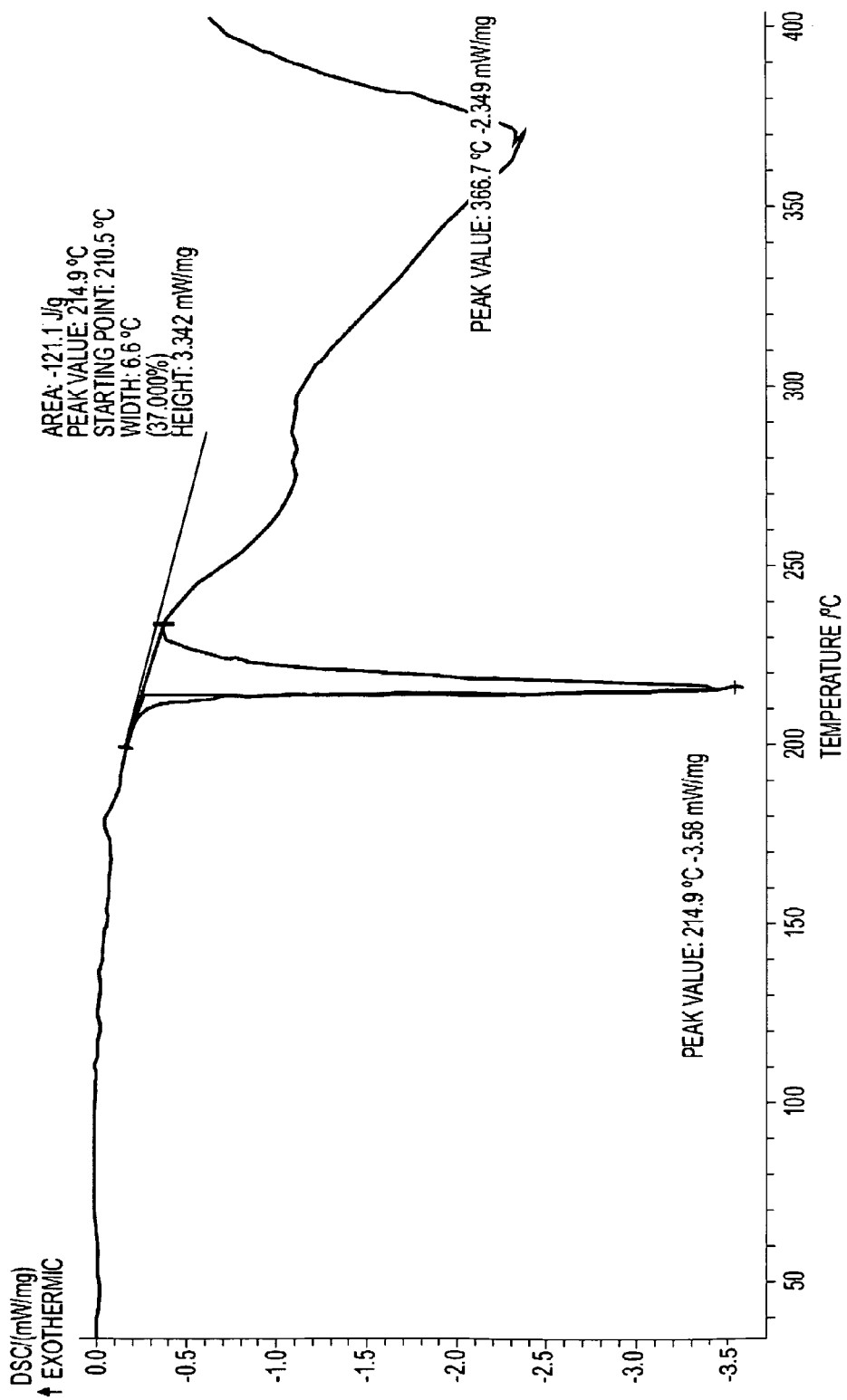
FIG. 6 is the DSC thermal analysis diagram of (S)—[N-3-(3'-fluoro-4'-(4"-phenyl piperazinyl))phenyl-2-oxo-5-oxazolidinyl]methyl acetamide anhydride.

The following abbreviations and terms have the indicated meanings throughout:

"Polymorphism" is defined as in the International Conference on Harmonization (ICH) Guideline Q6A Guideline: Specifications for New Drug Substances and Products: Chemical Substances, October 1999 and refers to the occurrence of different solid forms of the same drug substance. Polymorphs can be unsolvated or solvated, such as hydrated, crystal forms. Unsolvated crystal forms are crystals that do not have solvent incorporated within the crystal structure and include anhydrous crystal forms or anhydrates. Solvated crystal forms, or solvates, are crystalline solid adducts containing either stoichiometric or nonstoichiometric amounts of solvent molecules incorporated within the crystal structure. If the incorporated solvent is water, the solvates are also commonly known as hydrates. Amorphous solids possess disordered arrangements of molecules and do not possess a distinguishable crystal lattice.

The term "solution" means a mixture of one or more solutes in one or more solvents. Solution is intended to encompass homogeneous mixtures as well as heterogeneous mixtures, such as slurries or other mixtures having a suspension of insoluble (not dissolved) material.

By a "detectable amount" is meant a sufficient amount to give positive identification but not necessarily quantitation of the compound by any at least one suitable analytical technique, for example HPLC, XRPD, or other means.

The term "organic solvent" is broadly intended to mean any organic solvent.

The at least one crystalline hydrate disclosed herein can be used in different enriched isotopic forms, e.g., enriched in the content of $^2$H, $^3$H, $^{11}$C, $^{13}$C and/or $^{14}$C. In one embodiment, the compounds are deuterated. Such deuterated forms can be made by the procedure described in U.S. Pat. Nos. 5,846,514 and 6,334,997. As described in U.S. Pat. Nos. 5,846,514 and 6,334,997, deuteration can improve the efficacy and increase the duration of action of drugs. Deuterium substituted compounds can be synthesized using various methods such as described in: Dean, Dennis C., Editor: Recent Advances in the Synthesis and Applications of Radiolabeled Compounds for Drug Discovery and Development. [In Curr., Pharm. Des., 2000; 6(10), 110 pp.]; Kabalka, George W.; Varma, Rajender S: The Synthesis of Radiolabeled Compounds via Organometallic Intermediates, Tetrahedron, 1989, 45(21), pp. 6601-21; and Evans, E. Anthony: Synthesis of radiolabeled compounds, J. Radioanal. Chem., 1981, 64(1-2), pp. 9-32.

The term "therapeutically effective amount" of at least one crystalline hydrate described herein means an amount effective, when administered to a subject in recognized need, such as a human or non-human patient, to alleviate the symptoms or stop the progression of a bacterial infection.

The term "(S)—N-3-(3'-fluoro-4'-(4"-phenyl piperazinyl))phenyl-2-oxo-5-oxazolidinyl]methyl acetamide" or "(S)—N-[3-(3'-fluoro-4'-(4"-(phenyl)-piperazinyl)-phenyl)-2-oxo-5-oxazolidinyl]-methyl]acetamide" or "(S)—N-((3-(3-fluoro-4-(4-phenylpiperazin-1-yl)phenyl)-2-oxooxazolidin-5-yl)methyl)acetamide" refers to a chemical entity with the following structure:

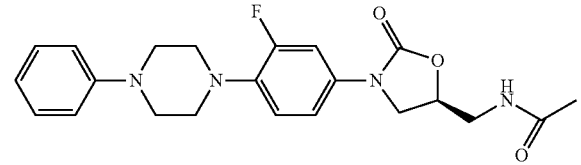 [SMILES: CC(=O)NC[C@H]1CN(c2ccc(N3CCN(c4ccccc4)CC3)c(F)c2)C(=O)O1]

Provided is at least one crystalline hydrate of (S)—N-3-(3'-fluoro-4'-(4"-phenyl piperazinyl))phenyl-2-oxo-5-oxazolidinyl]methyl acetamide.

Also provided is at least one crystalline hydrate of (S)—[N-3-(3'-fluoro-4'-(4"-phenyl piperazinyl))phenyl-2-oxo-5-oxazolidinyl]methyl acetamide with the following formula:

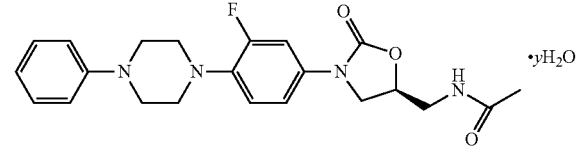

wherein y is a number ranging from 1/12 to 1, for example, y is chosen from 1/12, 2/7, 2/5, 1/2, and 3/4.

In some embodiments, the water content of the at least one crystalline hydrate described herein remains substantially unchanged when the at least one crystalline hydrate described herein is exposed to normal temperature. For example, in some embodiments, the water content of the at least one crystalline hydrate described herein, when exposed to normal temperatures, changes, by less than about 10%, further for example, by less than about 5%, such as less than about 2% in some embodiments, and in some embodiments, even by less than about 1%.

In some embodiments, the at least one crystalline hydrate is at least 99%, at least 95%, at least 90%, or at least 80% free of crystalline hydrates of (R)—[N-3-(3'-fluoro-4'-(4"-phenyl piperazinyl))phenyl-2-oxo-5-oxazolidinyl]methyl acetamide. In some other embodiments, the at least one crystalline hydrate is at least 70%, or at least 60% free of crystalline hydrates of (R)—[N-3-(3'-fluoro-4'-(4"-phenyl piperazinyl))phenyl-2-oxo-5-oxazolidinyl]methyl acetamide. In further other embodiments, the at least one crystalline hydrate is at least more than 50% free of crystalline hydrates of (R)—[N-3-(3'-fluoro-4'-(4"-phenyl piperazinyl))phenyl-2-oxo-5-oxazolidinyl]methyl acetamide.

In some embodiments, the at least one crystalline hydrate described herein of the formula above contains no more than about 50% by weight of any other polymorphic form(s), such as where y is greater than 1 or less than 1/12. In some embodiments, the at least one crystalline hydrate described herein contains no more than about 10% by weight of any other polymorphic form(s). In some embodiments, the at least one crystalline hydrate described herein contains no more than about 5% by weight of any other polymorphic form(s). In some embodiments, the at least one crystalline hydrate described herein contains even no more than about 1% by weight of any other polymorphic form(s).

In some embodiments, the at least one crystalline hydrate described herein has a chemical purity of greater than about 95%. In other embodiments, the at least one crystalline hydrate described herein has a chemical purity of greater than about 98%. In yet other embodiments, the at least one crystalline hydrate described herein has a chemical purity of greater than about 99%. Chemical purity can be ascertained by any at least one suitable analytical technique, for example, by high pressure liquid chromatography (HPLC).

In some embodiments, the at least one crystalline hydrate described herein may be identified by any one or more solid state analytical methods. For example, the at least one crystalline hydrate may be characterized according to any one or more of, e.g., X-ray diffraction, unit cell constants obtained from a single crystal of the hydrate, Fourier transform infrared spectroscopy, differential scanning calorimetry curve data, solid state nuclear magnetic resonance spectroscopy, and Raman spectroscopy.

A sample is considered to be a crystalline hydrate if it is characterized as such by any at least one of the methods described herein, regardless of any inconsistent or contradictory results obtained by any of the other methods described above. In addition, a sample is considered to be a crystalline hydrate if it is characterized as such by any at least one of the above methods under a particular set of experimental conditions, regardless of any inconsistent or contradictory results obtained by the same method under a different set of experimental conditions.

In some embodiments, the at least one crystalline hydrate may be characterized according to melting point. For example, also provided is an embodiment of at least one crystalline (S)—[N-3-(3'-fluoro-4'-(4"-phenyl piperazinyl))phenyl-2-oxo-5-oxazolidinyl]methyl acetamide hydrate having a melting point ranging from 210° C. to 215° C., as measured by a capillary tube (i.e., a melting point apparatus).

In some embodiments, the at least one crystalline hydrate may be characterized according to X-ray powder diffraction. For example, the X-ray powder diffractogram of anhydrate (S)—[N-3-(3'-fluoro-4'-(4"-phenyl piperazinyl))phenyl-2-oxo-5-oxazolidinyl]methyl acetamide is distinguishable from those of crystalline (S)—[N-3-(3'-fluoro-4'-(4"-phenyl piperazinyl))phenyl-2-oxo-5-oxazolidinyl]methyl acetamide hydrates. For instance, the X-ray powder diffractogram of anhydrate (S)—[N-3-(3'-fluoro-4'-(4"-phenyl piperazinyl))phenyl-2-oxo-5-oxazolidinyl]methyl acetamide, measured with CuKα radiation, may have peaks (2θ) chosen from those having about the following values: 4.37, 10.50, 15.92, 17.12, 22.40, and 26.11, each of the diffraction angles being ±0.02 degrees (2θ). The X-ray powder diffractogram of the at least one crystalline (S)—[N-3-(3'-fluoro-4'-(4"-phenyl piperazinyl))phenyl-2-oxo-5-oxazolidinyl]methyl acetamide hydrate, in contrast, may not have those peaks. The intensity in the X-ray powder diffractogram of different batches of the hydrates described herein may vary, because of, for example, preferred orientation or even variable hydration. Furthermore, in the X-ray powder diffractograms of the hydrates described herein, there can be differences in the measured peaks, due to the difference of the measuring instruments and testing conditions during the X-ray diffraction measurement. For instance, the experiments described herein used the X-ray diffraction DX-1000 machine made by Chengdu Center for Analysis and Testing, Chinese Academy of Sciences, and according to the instrument precision, the measurement error of 2θ value is at ±0.02 2θ. In addition, in the Examples described below, the conditions chosen for measuring the X-ray powder diffraction of the hydrates included: CuKa radiation, 1.54 monochromator, tube voltage 40 kV, and tube current 25 mA. But notwithstanding experimental and machine errrors, and principles such as preferred orientation, one skilled in the an can find sufficient information in the XRPD data provided herein to identify a specific crystalline hydrate. In other words, not all of the data from the diffractogram are necessary to identify the hydrate.

Also provided is an embodiment of at least one crystalline (S)—[N-3-(3'-fluoro-4'-(4"-phenyl piperazinyl))phenyl-2-oxo-5-oxazolidinyl]methyl acetamide hydrate with an XRPD, measured with CuKα radiation, having at least the peaks (2θ) chosen from those having about the following values: 4.04, 16.09, 18.66, and 20.16, each of the diffraction angles being ±0.02 degrees (2θ).

Also provided is a method for the preparation of at least one crystalline (S)—[N-3-(3'-fluoro-4'-(4"-phenyl piperazinyl))phenyl-2-oxo-5-oxazolidinyl]methyl acetamide hydrate comprising forming a solution of (S)—[N-3-(3'-fluoro-4'-(4"-phenyl piperazinyl))phenyl-2-oxo-5-oxazolidinyl]methyl acetamide by dissolving (S)—[N-3-(3'-fluoro-4'-(4"-phenyl piperazinyl))phenyl-2-oxo-5-oxazolidinyl]methyl acetamide with at least one suitable solvent chosen, for example, from water, nonacidic organic solvents and acidic solvents chosen from acidic organic solvents and acidic inorganic solvents;

stirring the solution at an appropriate temperature ranging, for example, from 30° C. to 90° C., such as from 35° C. to 70° C., further such as from 35° C. to 60° C. for an appropriate period of time, such as at least one hour, further such as from 1 hour to 36 hours, from example, from 1 hour to 10 hours, even further for example, from 1 hour to 5 hours; and crystallizing (S)—[N-3-(3'-fluoro-4'-(4"-phenyl piperazinyl))phenyl-2-oxo-5-oxazolidinyl]methyl acetamide hydrate from the solution.

In some embodiments, the method further comprises filtering the solution of (S)—[N-3-(3'-fluoro-4'-(4"-phenyl piperazinyl))phenyl-2-oxo-5-oxazolidinyl]methyl acetamide prior to the crystallization.

In some embodiments, the method further comprises adding activated carbon to the solution of (S)—[N-3-(3'-fluoro-4'-(4"-phenyl piperazinyl))phenyl-2-oxo-5-oxazolidinyl]methyl acetamide during the stirring and/or crystallization for sterilization or decoloration.

In some embodiments, the method further comprises vacuum drying the crystalline (S)—[N-3-(3'-fluoro-4'-(4"-phenyl piperazinyl))phenyl-2-oxo-5-oxazolidinyl]methyl acetamide hydrate.

Methods for crystallizing at least one (S)—[N-3-(3'-fluoro-4'-(4"-phenyl piperazinyl))phenyl-2-oxo-5-oxazolidinyl]methyl acetamide hydrate from the solution of (S)—[N-3-(3'-fluoro-4'-(4"-phenyl piperazinyl))phenyl-2-oxo-5-oxazolidinyl]methyl acetamide are exemplified herein.

In some embodiments, the crystallization comprises allowing the solution to stand for a sufficient period of time to allow the at least one crystalline (S)—[N-3-(3'-fluoro-4'-(4"-phenyl piperazinyl))phenyl-2-oxo-5-oxazolidinyl]methyl acetamide hydrate to form from the solution.

In some embodiments, the crystallization comprises adding at least one solvent that does not dissolve (S)—[N-3-(3'-fluoro-4'-(4"-phenyl piperazinyl))phenyl-2-oxo-5-oxazolidinyl]methyl acetamide well (herein referred to as a "poor solvent") to the solution; or pouring the solution into at least one poor solvent in order to crystallize at least one crystalline (S)—[N-3-(3'-fluoro-4'-(4"-phenyl piperazinyl))phenyl-2-oxo-5-oxazolidinyl]methyl acetamide hydrate from the solution.

In some embodiments, the crystallization comprises adding an appropriate amount of (S)—[N-3-(3'-fluoro-4'-(4"-phenyl piperazinyl))phenyl-2-oxo-5-oxazolidinyl]methyl acetamide hydrate(s) as a seed crystal into the solution to facilitate the formation of crystalline hydrate. Once the (S)—[N-3-(3'-fluoro-4'-(4"-phenyl piperazinyl))phenyl-2-oxo-5-oxazolidinyl]methyl acetamide hydrate(s) are in hand, the appropriate amount for seeding can be readily determined by one of ordinary skill in the art.

In one embodiment, the method for the preparation of at least one crystalline (S)—[N-3-(3'-fluoro-4'-(4"-phenyl piperazinyl))phenyl-2-oxo-5-oxazolidinyl]methyl acetamide hydrate comprises forming a solution of (S)—[N-3-(3'-fluoro-4'-(4"-phenyl piperazinyl))phenyl-2-oxo-5-oxazolidinyl]methyl acetamide by dissolving (S)—[N-3-(3'-fluoro-4'-(4"-phenyl piperazinyl))phenyl-2-oxo-5-oxazolidinyl]methyl acetamide with at least one solvent chosen from water, nonacidic organic solvents, and acidic solvents chosen from acidic organic solvents and acidic inorganic solvents;
stirring the solution at a temperature ranging from 35° C. to 70° C. for a period of time ranging from 1 to 5 hours;
filtering the solution; and
crystallizing (S)—[N-3-(3'-fluoro-4'-(4"-phenyl piperazinyl))phenyl-2-oxo-5-oxazolidinyl]methyl acetamide hydrate from the solultion by allowing the solution to stand for a sufficient period of time to form the crystal or by adding a suitable amount of at least one poor solvent into the solution.

In another embodiment, the method for the preparation of at least one crystalline (S)—[N-3-(3'-fluoro-4'-(4"-phenyl piperazinyl))phenyl-2-oxo-5-oxazolidinyl]methyl acetamide hydrate comprises forming a solution of (S)—[N-3-(3'-fluoro-4'-(4"-phenyl piperazinyl))phenyl-2-oxo-5-oxazolidinyl]methyl acetamide by dissolving (S)—[N-3-(3'-fluoro-4'-(4"-phenyl piperazinyl))phenyl-2-oxo-5-oxazolidinyl]methyl acetamide with at least one solvent chosen from water, nonacidic organic solvents, and acidic solvents;
stirring the solution at a temperature ranging from 35° C. to 60° C. for a period of time ranging from 1 to 5 hours;
filtering the solution; and
crystallizing (S)—[N-3-(3'-fluoro-4'-(4"-phenyl piperazinyl))phenyl-2-oxo-5-oxazolidinyl]methyl acetamide hydrate from the solultion by allowing the solution to stand for a sufficient period of time to form the crystal or by adding at least one poor solvent into the solution.

A. (S)—[N-3-(3'-fluoro-4'-(4"-phenyl piperazinyl))phenyl-2-oxo-5-oxazolidinyl]methyl acetamide 1/2 hydrate ("hemi-hydrate")

One of the crystalline hydrates disclosed herein is (S)—[N-3-(3'-fluoro-4'-(4"-phenyl piperazinyl))phenyl-2-oxo-5-oxazolidinyl]methyl acetamide 1/2 hydrate with the following formula:

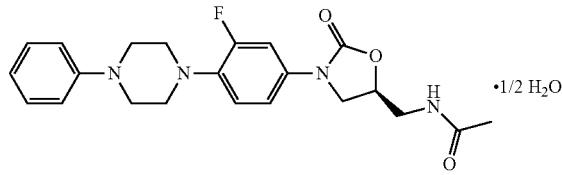 [SMILES: CC(=O)NC[C@H]1CN(c2ccc(N3CCN(c4ccccc4)CC3)c(F)c2)C(=O)O1]

In some embodiments, the melting point of (S)—[N-3-(3'-fluoro-4'-(4"-phenyl piperazinyl))phenyl-2-oxo-5-oxazolidinyl]methyl acetamide 1/2 hydrate ranges from 210° C. to 215° C., as measured by a capillary tube.

In some embodiments, the water content of (S)—[N-3-(3'-fluoro-4'-(4"-phenyl piperazinyl))phenyl-2-oxo-5-oxazolidinyl]methyl acetamide 1/2 hydrate, as measured by TGA, is about 2.10±0.15%.

Also in an embodiment, the X-ray powder diffractogram of crystalline (S)—[N-3-(3'-fluoro-4'-(4"-phenyl piperazinyl))phenyl-2-oxo-5-oxazolidinyl]methyl acetamide 1/2-hydrate, measured with CuKa radiation, has peaks (2θ) chosen from those having about the following values: 4.07, 12.00, 16.06, 18.56, and 40.88, each of the diffraction angles being ±0.02 degrees (2θ).

In some embodiments, the X-ray powder diffractogram of (S)—[N-3-(3'-fluoro-4'-(4"-phenyl piperazinyl))phenyl-2-oxo-5-oxazolidinyl]methyl acetamide 1/2-hydrate, measured with CuKa radiation, has peaks (2θ) chosen from those having about the following values: 4.04, 7.71, 8.05, 8.46, 10.98, 12.06, 14.16, 16.09, 18.66, 20.16, 21.47, 22.15, 23.32, 24.19, 25.98, 27.07, 28.48, 31.40, 32.25, 33.15, 35.36, 36.44, 37.81, 39.55, 40.94, 43.17, 43.76, 45.26, 45.86, and 47.25, each of the diffraction angles being ±0.02 degrees (2θ).

In some embodiments, the crystalline (S)—[N-3-(3'-fluoro-4'-(4"-phenyl piperazinyl))phenyl-2-oxo-5-oxazolidinyl]methyl acetamide 1/2 hydrate is at least 99%, at least 95%, at least 90%, or at least 80% free of crystalline hydrates of (R)—[N-3-(3'-fluoro-4'-(4"-phenyl piperazinyl))phenyl-2-oxo-5-oxazolidinyl]methyl acetamide. In some other embodiments, the crystalline (S)—[N-3-(3'-fluoro-4'-(4"-phenyl piperazinyl))phenyl-2-oxo-5-oxazolidinyl]methyl acetamide 1/2 hydrate is at least 70%, or at least 60% free of crystalline hydrates of (R)—[N-3-(3'-fluoro-4'-(4"-phenyl piperazinyl))phenyl-2-oxo-5-oxazolidinyl]methyl acetamide. In further other embodiments, the crystalline (S)—[N-3-(3'-fluoro-4'-(4"-phenyl piperazinyl))phenyl-2-oxo-5-oxazolidinyl]methyl acetamide 1/2 hydrate is at least more than 50% free of crystalline hydrates of (R)—[N-3-(3'-fluoro-4'-(4"-phenyl piperazinyl))phenyl-2-oxo-5-oxazolidinyl]methyl acetamide.

In some embodiments, the method for the preparation of a crystalline (S)—[N-3-(3'-fluoro-4'-(4"-phenyl piperazinyl))phenyl-2-oxo-5-oxazolidinyl]methyl acetamide 1/2 hydrate, comprises
  forming a solution of (S)—[N-3-(3'-fluoro-4'-(4"-phenyl piperazinyl))phenyl-2-oxo-5-oxazolidinyl]methyl acetamide by dissolving (S)—[N-3-(3'-fluoro-4'-(4"-phenyl piperazinyl))phenyl-2-oxo-5-oxazolidinyl]methyl acetamide with
    an acidic solvent having a pH value≤5 or
    a mixed solvent comprising at least one nonacidic organic solvent and at least one acidic solvent having a pH value≤5, wherein the at least one acidic solvent and the at least one organic solvent are mixed at an appropriate volumetric ratio, such as at a volumetric ratio ranging from 1:9 to 9:1, further such as ranging from 2:8 to 8:2 or from 3:7 to 7:3;
  stirring the solution at an appropriate temperature, such as at a temperature ranging from 30° C. to 80° C., such as from 35° C. to 70° C., further such as from 35° C. to 60° C., for an appropriate period of time, such as at least one hour, such as from one to ten hours, further such as from one to five hours, or more than ten hours; and
  crystallizing (S)—[N-3-(3'-fluoro-4'-(4"-phenyl piperazinyl))phenyl-2-oxo-5-oxazolidinyl]methyl acetamide 1/2 hydrate from the solution.

In some embodiments, the 1/2 hydrate is a white or near-white lamellar crystal.

The at least one acidic solvent having a pH value≤5 can be an organic or inorganic acidic solvent. In some embodiments, the at least one acidic solvent as disclosed herein can be chosen from hydrochloric acid, sulfuric acid, phosphoric acid, citric acid, acetic acid, permanganic acid, perchloric acid, hydrobromic acid, nitric acid, formic acid, tartaric acid, benzoic acid, phenylacetic acid, maleic acid, oxalic acid, trifluoroacetic acid, and dichloroacetic acid. For instance, the at least one acidic solvent can be chosen from hydrochloric acid, sulfuric acid, and citric acid. Other acidic solvents, of course, could be used. As a non-limiting example, 50% by weight of hydrochloric acid can be used as the acidic solvent to prepare the 1/2 hydrate.

In some embodiments, the at least one nonacidic organic solvent can be chosen from ethanol, methanol, acetonitrile, ethyl acetate, tetrahydrofuran, petroleum ether, and the mixtures thereof. Other nonacidic organic solvents, of course, could be used.

B. (S)—[N-3-(3'-fluoro-4'-(4"-phenyl piperazinyl))phenyl-2-oxo-5-oxazolidinyl]methyl acetamide 2/5 hydrate One of the crystalline hydrates disclosed herein is (S)—[N-3-(3'-fluoro-4'-(4"-phenyl piperazinyl))phenyl-2-oxo-5-oxazolidinyl]methyl acetamide 2/5 hydrate with the following formula:

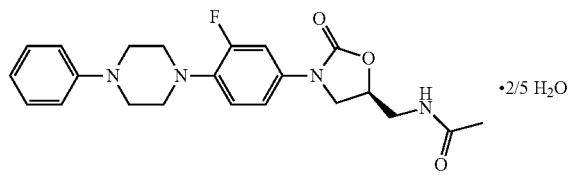 [SMILES: CC(=O)NC[C@H]1CN(c2ccc(N3CCN(c4ccccc4)CC3)c(F)c2)C(=O)O1]

In some embodiments, the melting temperature of (S)—[N-3-(3'-fluoro-4'-(4"-phenyl piperazinyl))phenyl-2-oxo-5-oxazolidinyl]methyl acetamide 2/5 hydrate ranges from 210° C. to 215° C., as measured by a capillary tube.

In some embodiments, the water content of (S)—[N-3-(3'-fluoro-4'-(4"-phenyl piperazinyl))phenyl-2-oxo-5-oxazolidinyl]methyl acetamide 2/5 hydrate, as measured by TGA, is about 1.70±0.15%.

In some embodiments, the X-ray powder diffractogram of (S)—[N-3-(3'-fluoro-4'-(4"-phenyl piperazinyl))phenyl-2-oxo-5-oxazolidinyl]methyl acetamide 2/5 hydrate, measured with CuKα radiation, has peaks (2θ) chosen from those having about the following values: 4.13, 7.07, 8.16, 9.97, 12.20, 13.50, 14.13, 16.27, 17.25, 18.03, 18.72, 20.24, 21.19, 22.16, 23.04, 25.10, 26.90, 27.89, 30.08, 33.45, 37.16, 38.94, 39.62, 40.96, 41.42, 41.84, 43.14, 43.88, 45.30, 45.87, 47.33, and 49.18, each of the diffraction angles being ±0.02 degrees (2θ).

In some embodiments, the crystalline (S)—[N-3-(3'-fluoro-4'-(4"-phenyl piperazinyl))phenyl-2-oxo-5-oxazolidinyl]methyl acetamide 2/5 hydrate is at least 99%, at least 95%, at least 90%, or at least 80% free of crystalline hydrates of (R)—[N-3-(3'-fluoro-4'-(4"-phenyl piperazinyl))phenyl-2-oxo-5-oxazolidinyl]methyl acetamide. In some other embodiments, the crystalline (S)—[N-3-(3'-fluoro-4'-(4"-phenyl piperazinyl))phenyl-2-oxo-5-oxazolidinyl]methyl acetamide 2/5 hydrate is at least 70%, or at least 60% free of crystalline hydrates of (R)—[N-3-(3'-fluoro-4'-(4"-phenyl piperazinyl))phenyl-2-oxo-5-oxazolidinyl]methyl acetamide. In further other embodiments, the crystalline (S)—[N-3-(3'-fluoro-4'-(4"-phenyl piperazinyl))phenyl-2-oxo-5-oxazolidinyl]methyl acetamide 2/5 hydrate is at least more than 50% free of crystalline hydrates of (R)—[N-3-(3'-fluoro-4'-(4"-phenyl piperazinyl))phenyl-2-oxo-5-oxazolidinyl]methyl acetamide.

In some embodiments, the method for the preparation of a crystalline (S)—[N-3-(3'-fluoro-4'-(4"-phenyl piperazinyl))phenyl-2-oxo-5-oxazolidinyl]methyl acetamide 2/5 hydrate, comprises
  forming a solution of (S)—[N-3-(3'-fluoro-4'-(4"-phenyl piperazinyl))phenyl-2-oxo-5-oxazolidinyl]methyl acetamide by dissolving (S)—[N-3-(3'-fluoro-4'-(4"-phenyl piperazinyl))phenyl-2-oxo-5-oxazolidinyl]methyl acetamide with a mixed solvent comprising at least one acidic solvent with a pH ranging from 2 to 5 and at least one nonacidic organic solvent, wherein the at least one acidic solvent and the at least one nonacidicorganic solvent are mixed at an appropriate volumetric ratio, such as at a volumetric ratio ranging from 1:9 to 9:1, such as ranging from 2:8 to 8:2 or ranging from 3:7 to 7:3, wherein the at least one acidic solvent is chosen from hypophosphorous acid, metaphosphoric acid, meta-aluminic acid, lactic acid, and succinic acid, and wherein the at least one nonacidic organic solvent is chosen from propanol, glycol, n-butanol, and N,N-dimethylformamide;
  stirring the solution at an appropriate temperature, such as a temperature ranging from 30° C. to 80° C. or from 35° C. to 70° C., further such as from 35° C. to 60° C., for an appropriate period of time, such as at least one hour, further such as more than ten hours, even further such as from one to ten hours, or even further such as from one to five hours; and crystallizing (S)—[N-3-(3'-fluoro-4'-(4"-phenyl piperazinyl))phenyl-2-oxo-5-oxazolidinyl]methyl acetamide 2/5 hydrate from the solution.

In some embodiments, the 2/5 hydrate is a white or near-white lamellar crystal.

C. (S)—[N-3-(3'-fluoro-4'-(4"-phenyl piperazinyl))phenyl-2-oxo-5-oxazolidinyl]methyl acetamide 2/7 hydrate One of the crystalline hydrates disclosed herein is (S)—[N-3-(3'-fluoro-4'-(4"-phenyl piperazinyl))phenyl-2-oxo-5-oxazolidinyl]methyl acetamide 2/7 hydrate with the following formula:

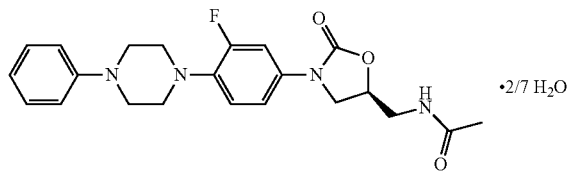 [SMILES: CC(=O)NC[C@H]1CN(c2ccc(N3CCN(c4ccccc4)CC3)c(F)c2)C(=O)O1]

In some embodiments, the melting temperature of (S)—[N-3-(3'-fluoro-4'-(4"-phenyl piperazinyl))phenyl-2-oxo-5-oxazolidinyl]methyl acetamide 2/7 hydrate ranges from 210° C. to 215° C., as measured by a capillary tube.

In some embodiments, the water content of (S)—[N-3-(3'-fluoro-4'-(4"-phenyl piperazinyl))phenyl-2-oxo-5-oxazolidinyl]methyl acetamide 2/7 hydrate, as measured by TGA, is about 1.20±0.15%.

In some embodiments, the X-ray powder diffractogram of (S)—[N-3-(3'-fluoro-4'-(4"-phenyl piperazinyl))phenyl-2-oxo-5-oxazolidinyl]methyl acetamide 2/7 hydrate, measured with CuKα radiation, has peaks (2θ) chosen from those having about the following values: 4.21, 7.06, 8.19, 10.02, 12.25, 13.53, 14.23, 16.29, 17.33, 18.09, 18.77, 20.29, 21.25, 23.06, 25.13, 27.06, 27.89, 30.12, 33.39, 37.23, 37.81, 39.02, 39.58, 41.48, 41.84, 43.22, 43.86, 45.37, 45.87, 47.40, and 49.36, each of the diffraction angles being ±0.02 degrees (2θ).

In some embodiments, the crystalline (S)—[N-3-(3'-fluoro-4'-(4"-phenyl piperazinyl))phenyl-2-oxo-5-oxazolidinyl]methyl acetamide 2/7 hydrate is at least 99%, at least 95%, at least 90%, or at least 80% free of crystalline hydrates of (R)—[N-3-(3'-fluoro-4'-(4"-phenyl piperazinyl))phenyl-2-oxo-5-oxazolidinyl]methyl acetamide. In some other embodiments, the crystalline (S)—[N-3-(3'-fluoro-4'-(4"-phenyl piperazinyl))phenyl-2-oxo-5-oxazolidinyl]methyl acetamide 2/7 hydrate is at least 70%, or at least 60% free of crystalline hydrates of (R)—[N-3-(3'-fluoro-4'-(4"-phenyl piperazinyl))phenyl-2-oxo-5-oxazolidinyl]methyl acetamide. In further other embodiments, the crystalline (S)—[N-3-(3'-fluoro-4'-(4"-phenyl piperazinyl))phenyl-2-oxo-5-oxazolidinyl]methyl acetamide 2/7 hydrate is at least more than 50% free of crystalline hydrates of (R)—[N-3-(3'-fluoro-4'-(4"-phenyl piperazinyl))phenyl-2-oxo-5-oxazolidinyl]methyl acetamide.

In some embodiments, the method for the preparation of a crystalline (S)—[N-3-(3'-fluoro-4'-(4"-phenyl piperazinyl))phenyl-2-oxo-5-oxazolidinyl]methyl acetamide 2/7 hydrate, comprises:

forming a solution of (S)—[N-3-(3'-fluoro-4'-(4"-phenyl piperazinyl))phenyl-2-oxo-5-oxazolidinyl]methyl acetamide by dissolving (S)—[N-3-(3'-fluoro-4'-(4"-phenyl piperazinyl))phenyl-2-oxo-5-oxazolidinyl]methyl acetamide with a mixed solvent comprising water and at least one nonacidic organic solvent chosen from methyl acetate, ethyl acetate, propyl acetate, phenyl acetate, heptyl acetate, decyl acetate, isobutyl acetate, and glycol diacetate, and wherein the water and the at least one nonacidic organic solvent are mixed at an appropriate volumetric ratio, such as at a volumetric ratio ranging from 1:9 to 9:1, for example, from 2:8 to 8:2, or as a further example from 3:7 to 7:3;

stirring the solution at an appropriate temperature, such as at a temperature ranging from 30° C. to 80° C., such as from 35° C. to 70° C., further such as from 35° C. to 60° C., for an appropriate period of time, such as at least one hour, such as more than ten hours, further such as from one to ten hours, or even further such as from one to five hours; and crystallizing (S)—[N-3-(3'-fluoro-4'-(4"-phenyl piperazinyl))phenyl-2-oxo-5-oxazolidinyl]methyl acetamide 2/7 hydrate from the solution.

In some embodiments, the 2/7 hydrate is a white or near-white lamellar crystal.

D. (S)—[N-3-(3'-fluoro-4'-(4"-phenyl piperazinyl))phenyl-2-oxo-5-oxazolidinyl]methyl acetamide 1/12 hydrate One of the crystalline hydrates disclosed herein is (S)—[N-3-(3'-fluoro-4'-(4"-phenyl piperazinyl))phenyl-2-oxo-5-oxazolidinyl]methyl acetamide 1/12 hydrate with the following formula:

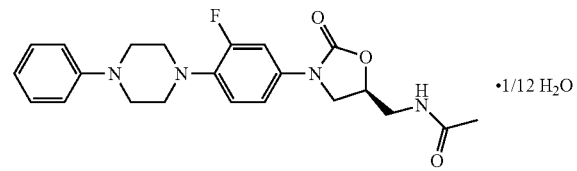 [SMILES: CC(=O)NC[C@H]1CN(c2ccc(N3CCN(c4ccccc4)CC3)c(F)c2)C(=O)O1]

In some embodiments, the melting temperature of (S)—[N-3-(3'-fluoro-4'-(4"-phenyl piperazinyl))phenyl-2-oxo-5-oxazolidinyl]methyl acetamide 1/12 hydrate ranges from 210° C. to 215° C., as measured by a capillary tube.

In some embodiments, the water content of (S)—[N-3-(3'-fluoro-4'-(4"-phenyl piperazinyl))phenyl-2-oxo-5-oxazolidinyl]methyl acetamide 1/12 hydrate, as measured by TGA, is about 0.40±0.15%.

In some embodiments, the X-ray powder diffractogram of (S)—[N-3-(3'-fluoro-4'-(4"-phenyl piperazinyl))phenyl-2-oxo-5-oxazolidinyl]methyl acetamide 1/12 hydrate, measured with CuKα radiation, has peaks (2θ) chosen from those having about the following values: 4.16, 4.44, 7.09, 8.76, 10.02, 12.15, 13.07, 13.57, 16.21, 17.77, 18.14, 18.74, 19.53, 20.23, 21.18, 21.85, 23.06, 23.77, 25.33, 26.89, 28.54, 30.21, 31.41, 33.19, 33.94, 36.89, 37.82, 39.56, 41.35, 43.33, 44.42, 45.32, 46.02, and 47.32, each of the diffraction angles being ±0.02 degrees (2θ).

In some embodiments, the crystalline (S)—[N-3-(3'-fluoro-4'-(4"-phenyl piperazinyl))phenyl-2-oxo-5-oxazolidinyl]methyl acetamide 1/12 hydrate is at least 99%, at least 95%, at least 90%, or at least 80% free of crystalline hydrates of (R)—[N-3-(3'-fluoro-4'-(4"-phenyl piperazinyl))phenyl- 2-oxo-5-oxazolidinyl]methyl acetamide. In some other embodiments, the crystalline (S)—[N-3-(3'-fluoro-4'-(4"-phenyl piperazinyl))phenyl-2-oxo-5-oxazolidinyl]methyl acetamide 1/12 hydrate is at least 70%, or at least 60% free of crystalline hydrates of (R)—[N-3-(3'-fluoro-4'-(4"-phenyl piperazinyl))phenyl-2-oxo-5-oxazolidinyl]methyl acetamide. In further other embodiments, the crystalline (S)—[N-3-(3'-fluoro-4'-(4"-phenyl piperazinyl))phenyl-2-oxo-5-oxazolidinyl]methyl acetamide 1/12 hydrate is at least more than 50% free of crystalline hydrates of (R)—[N-3-(3'-fluoro-4'-(4"-phenyl piperazinyl))phenyl-2-oxo-5-oxazolidinyl]methyl acetamide.

In some embodiments, the method for the preparation of a crystalline (S)—[N-3-(3'-fluoro-4'-(4"-phenyl piperazinyl))phenyl-2-oxo-5-oxazolidinyl]methyl acetamide 1/12 hydrate, comprises forming a solution of (S)—[N-3-(3'-fluoro-4'-(4"-phenyl piperazinyl))phenyl-2-oxo-5-oxazolidinyl]methyl acetamide by dissolving (S)—[N-3-(3'-fluoro-4'-(4"-phenyl piperazinyl))phenyl-2-oxo-5-oxazolidinyl]methyl acetamide with a mixed solvent comprising water and at least one nonacidic organic solvent, wherein the at least one nonacidic organic solvent is chosen from methanol, ethanol, acetonitrile, 1,2-propylene glycol, isopropanol, n-propanol, s-butanol, isobutanol, and ethylene glycol, and wherein the water and the at least one nonacidic organic solvent are mixed at an appropriate volumetric ratio such as ranging from 1:9 to 9:1, for example, from 2:8 to 8:2, or from 3:7 to 7:3;

stirring the solution at an appropriate temperature, such as at a temperature ranging from 30° C. to 80° C., such as from 35° C. to 70° C., for an appropriate period of time, such as at least one hour, further such as more than ten hours, even further from one to ten hours, or even further from one to five hours; and crystallizing (S)—[N-3-(3'-fluoro-4'-(4"-phenyl piperazinyl))phenyl-2-oxo-5-oxazolidinyl]methyl acetamide 1/12 hydrate from the solution.

In some embodiments, the 1/12 hydrate is a white or near-white lamellar crystal.

E. (S)—[N-3-(3'-fluoro-4'-(4"-phenyl piperazinyl))phenyl-2-oxo-5-oxazolidinyl]methyl acetamide 3/4 hydrate One of the crystalline hydrates disclosed herein is (S)—[N-3-(3'-fluoro-4'-(4"-phenyl piperazinyl))phenyl-2-oxo-5-oxazolidinyl]methyl acetamide 3/4 hydrate with the following formula:

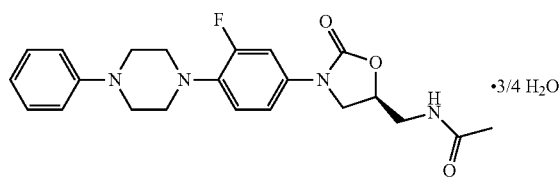 [SMILES: CC(=O)NC[C@H]1CN(c2ccc(N3CCN(c4ccccc4)CC3)c(F)c2)C(=O)O1]

In some embodiments, the melting temperature of (S)—[N-3-(3'-fluoro-4'-(4"-phenyl piperazinyl))phenyl-2-oxo-5-oxazolidinyl]methyl acetamide 3/4 hydrate ranges from 210° C. to 215° C., as measured by a capillary tube.

In some embodiments, the water content of (S)—[N-3-(3'-fluoro-4'-(4"-phenyl piperazinyl))phenyl-2-oxo-5-oxazolidinyl]methyl acetamide 3/4 hydrate, as measured by TGA, is about 3.30±0.15%.

In some embodiments, the X-ray powder diffractogram of (S)—[N-3-(3'-fluoro-4'-(4"-phenyl piperazinyl))phenyl-2-oxo-5-oxazolidinyl]methyl acetamide 3/4 hydrate, measured with CuKa radiation, has peaks (2θ) chosen from those having about the following values: 4.04, 8.55, 9.81, 11.04, 14.10, 16.09, 18.66, 20.12, 22.08, 23.64, 25.98, 27.00, 29.00, 30.26, 31.40, 33.25, 34.59, 35.36, 37.83, 39.55, 40.88, 41.89, 43.11, 44.72, 47.87, and 48.07, each of the diffraction angles being ±0.02 degrees (2θ).

In some embodiments, the crystalline (S)—[N-3-(3'-fluoro-4'-(4"-phenyl piperazinyl))phenyl-2-oxo-5-oxazolidinyl]methyl acetamide 3/4 hydrate is at least 99%, at least 95%, at least 90%, or at least 80% free of crystalline hydrates of (R)—[N-3-(3'-fluoro-4'-(4"-phenyl piperazinyl))phenyl-2-oxo-5-oxazolidinyl]methyl acetamide. In some other embodiments, the crystalline (S)—[N-3-(3'-fluoro-4'-(4"-phenyl piperazinyl))phenyl-2-oxo-5-oxazolidinyl]methyl acetamide 3/4 hydrate is at least 70%, or at least 60% free of crystalline hydrates of (R)—[N-3-(3'-fluoro-4'-(4"-phenyl piperazinyl))phenyl-2-oxo-5-oxazolidinyl]methyl acetamide. In further other embodiments, the crystalline (S)—[N-3-(3'-fluoro-4'-(4"-phenyl piperazinyl))phenyl-2-oxo-5-oxazolidinyl]methyl acetamide 3/4 hydrate is at least more than 50% free of crystalline hydrates of (R)—[N-3-(3'-fluoro-4'-(4"-phenyl piperazinyl))phenyl-2-oxo-5-oxazolidinyl]methyl acetamide.

In some embodiments, the method for the preparation of a crystalline (S)—[N-3-(3'-fluoro-4'-(4"-phenyl piperazinyl))phenyl-2-oxo-5-oxazolidinyl]methyl acetamide 3/4 hydrate comprises forming a solution of (S)—[N-3-(3'-fluoro-4'-(4"-phenyl piperazinyl))phenyl-2-oxo-5-oxazolidinyl]methyl acetamide by mixing (S)—[N-3-(3'-fluoro-4'-(4"-phenyl piperazinyl))phenyl-2-oxo-5-oxazolidinyl]methyl acetamide with water or with a mixed solvent comprising water and at least one nonacidic organic solvent, wherein the at least one nonacidic organic solvent is chosen from dimethyl sulfoxide and Tween-80, and wherein the water and the at least one nonacidic organic solvent are mixed at an appropriate volumetric ratio, such as at a ratio ranging from 1:9 to 9:1, further such as ranging from 2:8 to 8:2 or from 3:7 to 7:3;

stirring the solution at an appropriate temperature ranging from 30° C. to 90° C., such as from 45° C. to 75° C., for an appropriate period of time, such as at least one hour, further such as from one to thirty-five hours, or even further from twenty to thirty hours, or even further more than thirty-five hours; and crystallizing (S)—[N-3-(3'-fluoro-4'-(4"-phenyl piperazinyl))phenyl-2-oxo-5-oxazolidinyl]methyl acetamide 3/4 hydrate from the solution.

Also provided is a product of any of the methods of preparation described herein.

In some embodiments, a mixture of the at least one crystalline hydrate disclosed herein and anhydrate disclosed herein is obtained. In some other embodiments, a mixture of the at least one crystalline hydrate disclosed herein and anhydrate disclosed herein is obtained, and wherein the at least one crystalline hydrate is at least 99%, at least 95%, at least 90%, at least 80%, at least 70%, at least 60%, or more than 50% free of crystalline hydrates of (R)—[N-3-(3'-fluoro-4'-(4"-phenyl piperazinyl))phenyl-2-oxo-5-oxazolidinyl]methyl acetamide.

In some embodiments, the at least one crystalline hydrate described herein may be useful for the treatment of bacterial infections. In some embodiments, the bacterial infection is a gram positive bacterial infection. Those gram-positive bacteria include, but are not limited to, methicillin-susceptible and methicillin-resistant staphylococci (including *Staphylococcus aureus, S. epidermidis, S. haemolyticus, S. hominis, S. saprophyticus*, and coagulase-negative staphylococci), glycopeptide intermediary-susceptible *S. aureus* (GISA), vancomycin-resistant *Staphylococcus aureus* (VRSA), penicillin-susceptible and penicillin-resistant streptococci (including *Streptococcus pneumoniae, S. pyogenes, S. agalactiae, S. avium, S. bovis, S. lactis, S. sangius* and Streptococci Group C, Streptococci Group G and viridans streptococci), enterococci (including vancomycin-susceptible and vancomycin-resistant strains such as *Enterococcus faecalis* and *E. faecium*), *Clostridium difficile, C. clostridiiforme, C. innocuum, C. perfringens, C. ramosum, Listeria monocytogenes, Corynebacterium jeikeium, Bifidobacterium* spp., *Eubacterium aerofaciens, E. lentum, Lactobacillus acidophilus, L. casei, L. plantarum, Lactococcus* spp., *Leuconostoc* spp., *Pediococcus, Peptostreptococcus anaerobius, P. asaccarolyticus, P. magnus, P. micros, P. prevotii, P. productus, Propionibacterium acnes, Actinomyces* spp., and *Moraxella* spp. (including *M. catarrhalis*). In some embodiments, the bacterial infection is chosen from methicillin-resistant Staphylococci, vancomycin-resistant Staphylococci, vancomycin-resistant enterococci, penicillin-resistant pneumococci, and anaerobes. In some embodiments, the bacterial infection is chosen from *Staphylococcus aureus, Staphylococcu epidermidis, Enterococcus faecalis*, and *Enterococcus faecium*.

In some embodiments, the at least one crystalline hydrate described herein may be useful for the treatment of mixed infections that comprise different types of gram-positive bacteria, or which comprise both gram-positive and gram-negative bacteria.

In some embodiments, the method of treating a subject having a bacterial infection and in recognized need of treatment therefor comprising administering to said subject in recognized need of treatment an effective amount of at least one crystalline hydrate of (S)—[N-3-(3'-fluoro-4'-(4"-phenyl piperazinyl))phenyl-2-oxo-5-oxazolidinyl]methyl acetamide, wherein the at least one crystalline hydrate is at least 99%, at least 90%, at least 80%, at least 70%, at least 60%, or more than 50% free of crystalline hydrates of (R)—[N-3-(3'-fluoro-4'-(4"-phenyl piperazinyl))phenyl-2-oxo-5-oxazolidinyl]methyl acetamide, to treat said bacterial infection.

In some embodiments, the method of treating a subject having a bacterial infection and in recognized need of treatment therefor comprising administering to said subject in recognized need of treatment an effective amount of a pharmaceutical composition comprising:

at least one crystalline hydrate of (S)—[N-3-(3'-fluoro-4'-(4"-phenyl piperazinyl))phenyl-2-oxo-5-oxazolidinyl]methyl acetamide, wherein the at least one crystalline hydrate is at least 99%, at least 90%, at least 80%, at least 70%, at least 60%, or more than 50% free of crystalline hydrates of (R)—[N-3-(3'-fluoro-4'-(4"-phenyl piperazinyl))phenyl-2-oxo-5-oxazolidinyl]methyl acetamide; and at least one pharmaceutically acceptable diluents and/or carrier to provide said treatment.

The amount of the at least one crystalline hydrate described herein effective for achieving the desired biological effect may depend on a number of factors, for example, the intended use, the mode of administration, and the clinical condition of the patient. The daily dose may, for example, range from 0.01 mg to 200 mg (such as from 0.05 mg to 100 mg) per day. Single-dose formulations which can be administered orally include, for example, tablets or capsules.

For the therapy of the above-mentioned conditions, at least one crystalline hydrate may be used as the compound itself, but typically the at least one crystalline hydrate would be in the form of a pharmaceutical composition with an acceptable carrier. Representative carriers should be compatible with the other ingredients of the composition and not harmful for the patient's health. The carrier may be a solid or a liquid or both and may be formulated with a crystalline hydrate described herein as a single dose, for example as a tablet, which may be prepared from 0.05% to 95% by weight of the crystalline hydrate described herein. At least one active ingredient may likewise be present, including those chosen from other crystalline hydrates described herein. The pharmaceutical compositions described herein can be produced by known pharmaceutical methods, such as those involving mixing the ingredients with pharmacologically acceptable carriers and/or excipients.

In some embodiments, representative excipients would include but are not limited to: microcrystalline cellulose, lactose, sodium citrate, calcium carbonate, dicalcium phosphate, glycine, disintegrants such as starch, sodium cross-linked carboxymethyl cellulose, composite silicates, and polyethylene glycol with hight moleculr weight, granulation binders (such as polyvinylpyrrolidone, sucrose, gelatin, and Gum Arabic), and lubricants (such as magnesium stearate, glycerin, and talc).

In some embodiments, the at least one crystalline hydrate described herein may be combined with sweetners, delicate flavor agents, coloring matters, dyes, or emulsifiers, and mixtures thereof.

In some embodiments, the at least one crystalline hydrate described herein may not be converted upon formulation with the one or more pharmaceutically acceptable diluents. In other embodiments, the at least one crystalline hydrate described herein may be converted, in whole or in part, to one or more other forms, including a non-solid form, upon formulation with the one or more pharmaceutically acceptable diluents. Exemplary diluents would include but are not limited to, water, ethanol, propylene glycol, glycerine, and mixtures thereof. In some embodiments, the at least one crystalline hydrate described herein can be dissolved when formulated into a pharmaceutical composition. Accordingly, in such "dissolved" cases, the at least one crystalline hydrate no longer exists in crystalline form in the pharmaceutical composition.

In some embodiments, the at least one crystalline hydrate described herein may be formulated to a form suitable for slow relase, controlled release, extended release, pulsed release, and sustained relase of the hydrate described herein. For example, the at least one crystalline hydrate can be formulated as a sustained-release dosage form so that the hydrate is released into the gastrointestinal tract over a sustained period of time after the dosage is given to the patient.

Pharmaceutical compositions described herein can be those suitable for oral and peroral (for example sublingual) administration, although the suitable mode of administration may depend in each individual case on the nature and severity of the condition to be treated and on the nature of the crystalline hydrate(s) described herein used in each case to prepare the pharmaceutical composition. Coated formulations and coated slow-release formulations also are provided. Acid- and gastric juice-resistant formulations are possible. Suitable coatings resistant to gastric juice comprise cellulose acetate phthalate, polyvinyl acetate phthalate, hydroxypropylmethylcellulose phthalate, anionic polymers of methacrylic acid, and methyl methacrylate.

Suitable pharmaceutical compositions for oral administration prepared from the at least one crystalline hydrate described herein may be in the form of separate units such as, for example, capsules, cachets, and tablets, including suckable tablets, each of which can be prepared with a defined amount of the crystalline hydrate(s) described herein; as well as in the forms chosen from powders, granules, solutions, suspensions in an aqueous or nonaqueous liquid, and oil-in-water and water-in-oil emulsions. Those compositions may, as already mentioned, be prepared by any suitable pharmaceutical formulation method, such as those including a step wherein the crystalline hydrate described herein and a carrier (which may consist of one or more additional ingredients) are brought into contact. The compositions can generally be produced by uniform and homogeneous mixing of the crystalline hydrate described herein with a liquid and/or finely divided solid carrier, after which the product can be shaped. Thus, for example, a tablet can be produced by compressing or molding a powder or granules of the crystalline hydrate described herein, where appropriate with one or more additional ingredients. Compressed tablets can be produced by tableting the crystalline hydrate described herein in free-flowing form such as, for example, a powder or granules, where appropriate mixed with a binder, glidant, inert diluent and/or one (or more) surface-active/dispersing agent(s) in a suitable machine. Molded tablets can be produced by molding the crystalline hydrate described herein in powder form and then moistening with an inert liquid diluent, in a suitable machine. Compositions can also be prepared by wet granulation. Thus, for example, a composition can be prepared by wet granulation by mixing the crystalline hydrate described herein, one or more optional additional ingredients, a suitable solvent, and a binder to prepare a wet granulate, drying the wet granulate, and milling the dried granulate. The method may further comprise adding at least one lubricant to the dried milled granulate and compressing the dried milled granulate to form tablets. The optional additional ingredients may include, for example, at least one diluent and/or at least one disintegration agent. The suitable solvent can be water. In some embodiments, the diluent is chosen from calcium carbonate, calcium phosphate (dibasic and/or tribasic), calcium sulfate, powdered cellulose, dextrates, dextrin, fructose, kaolin, lactitol, anhydrous lactose, lactose monohydrate, maltose, mannitol, microcrystalline cellulose, sorbitol, sucrose, and starch. In some embodiments, the diluent can be present in an amount from about 35% to about 90% by weight of the tablet. In some embodiments, the binder can be chosen from acacia, alginic acid, carbomer, sodium carboxymethylcellulose, dextrin, ethylcellulose, gelatin, glucose, guar gum, hydroxypropyl cellulose, maltose, methylcellulose, polyethylene oxide, and povidone. In some exemplary embodiments, the binder is present in an amount of about 0.5% to about 5% by weight of the tablet. In other exemplary embodiments, the above-mentioned preparations contain about 0.05-5 g of the crystalline hydrate described herein per mililieter or per gram of the preparations.

In some embodiments, the at least one crystalline hydrate described herein can be prepared in a form chosen from lotions, solution agents, creams, ointments, and transdermal delivery devices. As a non-limiting example, the crystalline hydrate described herein can be in an ointment comprising one or more ingredients chosen from: mineral oil, liquid petrolatum, white petrolatum, polyethylene glycol, polyoxyethylene polyoxypropylene compound, emulsifying wax, and water. Further as a non-limiting example, the at least one crystalline hydrate described herein can be prepared as a lotion or cream comprising one or more ingredients chosen from: mineral oil, sorbitan monostearate, polyethylene glycol, liquid paraffin, Tween 60, cetyl esters wax, cetanol, 2-octyl dodecanol, benzyl alcohol, and water.

Pharmaceutical compositions which are suitable for peroral (sublingual) administration can comprise suckable tablets which can be prepared from the crystalline hydrate described herein with a flavoring agent, normally chosen from sucrose, gum arabic, tragacanth, and pastilles.

The at least one crystalline hydrate described herein can also be administered in combination with one or more other active ingredients. When administered as a combination, the active ingredients can be formulated as separate compositions that are administered at the same time or sequentially at different times, or the active ingredients can be administered in a single dosage form, i.e., single composition, provided that the active ingredients are not incompatible with other active ingredients or the formulation, or otherwise undesirably combined in a single composition.

In some embodiments, the at least one crystalline hydrate described herein can be administered with one or more other antimicrobial agents, such as antibacterial agents (antibiotics) and antifungal agents.

The phrase "co-therapy" (or "combination-therapy") or "in combination with", as used herein, defines the use of the at least one crystalline hydrate described herein as described herein and one or more other active ingredients, such as, for example:

administration of each active ingredient in a sequential manner in a regimen to provide beneficial effects of the drug combination; and/or co-administration of the aforementioned components in a substantially simultaneous manner (e.g., as in a single dosage form, such as a capsule, having a fixed ratio of the active ingredients or in multiple, separate capsules for each active ingredient, etc.).

Thus, methods described herein are not limited in the sequence of administration; the at least one crystalline hydrate described herein may be administered either prior to, at the same time with or after administration of the one or more other active ingredients.

The invention is further illustrated by the following non-limiting examples.

Experiments

EXAMPLE 1

Preparation of (S)—[N-3-(3'-fluoro-4'-(4"-phenyl piperazinyl))phenyl-2-oxo-5-oxazolidinyl]methyl acetamide (crude)

The (S)—[N-3-(3'-fluoro-4'-(4"-phenyl piperazinyl))phenyl-2-oxo-5-oxazolidinyl]methyl acetamide (crude) can be synthesized by methods generally disclosed in CN1355165A.

(1) Preparation of 3-fluoro-4-(4'-phenyl piperazinyl)nitrobenzene 50 ml of ethyl acetate, 13.5 ml of 4-phenyl piperazine, and 15.30 ml of diisopropyl ethyl amine were added into a 250 ml triple-neck flask. After magnetic stirring at room temperature, 9.0 ml of 3,4-difluoro-nitrobenzene was added. The reaction was carried out for 105 hours, followed by extraction with 150 ml of ethyl acetate for three times (150 ml×3). The extract was washed three times with saturated NaCl solution (150 ml×3), dried with anhydrous magnesium sulfate ($MgSO_4$), and evaporated to dryness. An orange yellow solid was obtained which was recrystallized with a mixture of acetone and water in volumetric ratio of 9:1 to produce orange yellow crystals (23.66 g) with a yield of 96.33%.

(2) Preparation of 3-fluoro-4-(4'-phenyl piperazinyl)aniline 6.69 g (119 mmol) of reduced iron powder, 23.57 ml of water, and 1.11 ml of glacial acetic acid were added into a 500 ml triple-neck flask and were refluxed for 80 minutes. 150 ml of an anhydrous ethanol containing the crystalline product obtained from the operation (1) (12.0 g, 39.82 mmol) was then slowly added dropwise to the mixture. After the addition was finished, the reaction was carried out for 10 minutes, and the resulting mixture was vacuum filtered, evaporated to remove ethanol, and then dissolved with ethyl acetate. The filter cake was washed with ethyl acetate three times. The organic phases were combined together, washed three times with water and one time with with saturated NaCl solution, dried with anhydrous magnesium sulfate ($MgSO_4$), and evaporated to dryness. A lightly white solid was obtained and used directly in the next reaction.

(3) Preparation of N-benzyloxycarbonyl-3-fluoro-4-(4'-phenyl piperazinyl)aniline 100 ml of dichloromethane and 13.0 g of the crude product obtained from the operation (2) were added into a 250 ml four-neck flask, and 7.91 ml of diisopropyl ethyl amine was added to the mixture at 0° C. The resulting mixture was stirred mechanically, and 5.34 ml benzyloxycarbonyl chloride was added dropwise. The resulting solution was stirred at room temperature for 16 hours, extracted three times with 100 ml of dichloromethane (100 ml×3), washed three times with saturated NaCl solution (100 ml×3), dried with anhydrous magnesium sulfate, and evaporated to dryness. A lightly white solid was obtained and further recrystallized with a mixture of acetone and water in a volumetric ratio of 7:3. 11.46 g of white crystals were obtained, and the yield was 76.66%.

(4) Preparation of (R)—[N-3-(3'-fluoro-4'-(4"-phenyl piperazinyl))phenyl-2-oxo-5-oxazolidinyl]methanol 3.4 g of the reaction product obtained from the operation (3) and 50 ml of anhydrous tetrahydrofuran were added into a 100 ml triple-neck flask (dried at 120° C. for more than 2 hours). Under a $N_2$ atmosphere, 6.60 ml of 1.6 M butyl lithium solution was added dropwise to the mixture at −78° C. The mixture was then stirred at −78° C. for 80 minutes. The mixture gradually turned into a yellow-green solution. 1.21 ml of (R)-glycidyl butyrate and 5 ml of anhydrous THF were then added dropwise into the mixture at −78° C., and the solution soon became clear. The reaction was carried out for 1 hour. The acetone bath was removed, and the temperature of the reaction mixture increased to room temperature. The reaction mixture was stirred for 16 hours, and a small amount of precipitates appeared. White solids were obtained. After running through silica gel column chromatography and recrystallization with a mixture of ethyl acetate and petroleum ether in a volumetric ratio of 1:3, 2.34 g of white crystals were obtained. The yield was 77.21%.

(5) Preparation of (R)—[N-3-(3'-fluoro-4'-(4"-phenyl piperazinyl))phenyl-2-oxo-5-oxazolidinyl]methanol methane sulfonate 25 ml of anhydrous dichloromethane, 1.74 g of the reaction product obtained in operation (4), and 1.32 mol of triethylamine were added into a 100 ml triple-neck flask at 0° C. 0.52 ml of methanesulfonyl chloride was added dropwise to the mixture, and the reaction was carried out for 65 minutes. A large amount of white precipitates appeared. The mixture was then extracted three times with 50 ml of dichloromethane (50 ml×3), washed three times with saturated NaCl solution (50 ml×3), dried with anhydrous magnesium sulfate, and evaporated to dryness. White solids were obtained, which were then recrystallized with a mixture of acetonitrile and water in a volumetric ratio of 1:1. 1.6065 g of white crystals were obtained. The yield was 75.92%.

(6) Preparation of (R)—[N-3-(3'-fluoro-4'-(4"-phenyl piperazinyl))phenyl-2-oxo-5-oxazolidinyl]methyl phthalimide 0.686 g of the reaction product obtained from operation (5), 0.347 g of potassium phthalimide, and 0.432 g of anhydrous potassium carbonate were added into a 100 ml triple-neck flask. The mixture was allowed to react for 3 hours. After the reaction, the resulting mixture was extracted three times with 50 ml of ethyl acetate (50 ml×3), washed three times with saturated NaCl solution (50 ml×3), dried with anhydrous magnesium sulfate, and evaporated to dryness. White solids were obtained, and used directly in the next step without further purification.

(7) Preparation of (S)—[N-3-(3'-fluoro-4'-(4"-phenyl piperazinyl))phenyl-2-oxo-5-oxazolidinyl]methyl acetamide The resuting product obtained from operation (6), 100 ml of anhydrous ethanol and 3.38 ml of 25 wt % methylamine aqueous solution (15.63 mmol) were added into a 250 ml triple-neck flask. The resulting mixture was refluxed for 1 hour, and then evaporated to dryness. The product was extracted with 50 ml of 0.1 M HCl and then twice with ethyl acetate (30 ml×2). The aqueous phase was transferred to a 100 ml triple-neck flask, and its pH was adjusted to slightly alkaline (pH=8-9) with an appropriate amount of NaOH. 0.46 ml of acetic anhydride (4.49 mmol) was added to the mixture, and the reaction was allowed to run for 10 minutes. After the reaction, the resulting mixture was extracted three times with 100 ml of ethyl acetate (100 ml×3), washed three times with saturated NaCl solution (100 ml×3), dried with anhydrous magnesium sulfate, evaporated to dryness, purified by column chromatography, and recrystallized with a mixture of ethyl acetate and petroleum ether in a volumetric ratio of 3:1. 183.5 mg of white solids were obtained, which were identified as (S)—[N-3-(3'-fluoro-4'-(4"-phenyl piperazinyl))phenyl-2-oxo-5-oxazolidinyl]methyl acetamide (crude) as follows. The yield was 29.49%.

Results of the elemental analysis: N %: 13.61, C %: 64.07, H %: 6.02. Theoretical value: N %: 13.58, C %: 64.06, H %: 6.11. The content measured by HPLC: 98.6%.

The X-Ray Powder Diffraction ("XRPD"), TGA, $^1H$ NMR, $^{13}C$ NMR, IR, and DSC thermal analysis spectra of the resulting (S)—[N-3-(3'-fluoro-4'-(4"-phenylpiperazinyl))phenyl-2-oxo-5-oxazolelidinyl]methyl acetamide are shown in FIGS. 1-6.

The X-ray powder diffractorgram shows the absorption peaks in the following diffraction angles (2θ)=4.37, 10.50, 11.75, 15.92, 17.12, 21.07, 22.40, 24.45, 26.11, 27.27, 29.49, 30.38, 32.90, 33.51, 39.32, 40.52, 42.84, 46.41, 51.38, with ±0.02 2θ for each peak.

$^1H$ NMR (400 Hz, DMSO-$d_6$) δ: 8.24 (t, 1H), 7.51 (dd, 1H), 7.26~7.18 (m, 3H), 7.12 (t, 1H), 6.95 (d, 2H), 6.81 (t,

1H), 4.74~4.68 (m, 1H), 4.09 (t, 1H), 3.70 (q, 1H), 3.41 (t, 2H), 3.29~3.27 (m, 4H), 3.13~3.10 (m, 4H), 1.83 (s, 3H).

$^{13}$C NMR (400 Hz, DMSO-d$_6$) δ: 170.1, 157.2, 154.2, 152.4, 151.0, 135.7, 133.5, 128.1, 118.6, 118.3, 115.8, 114.2, 107.1, 106.5, 71.7, 50.5, 48.6, 47.5, 22.5.

EXAMPLE 2

Preparation of (S)—[N-3-(3'-fluoro-4'-(4"-phenyl piperazinyl))phenyl-2-oxo-5-oxazolidinyl]methyl acetamide 1/2 hydrate 1 g of (S)—[N-3-(3'-fluoro-4'-(4"-phenyl piperazinyl))phenyl-2-oxo-5-oxazolidinyl]methyl acetamide crude prepared according to Example 1 was dissolved in 2 ml of 6 wt % hydrochloric acid. A small amount of activated carbon was added, and the reaction mixture was stirred at 50° C. for 2 hours, and filtered. After filtration, the liquid was left standing at room temperature, and crystals formed, which were collected, and further vacuum dried at 40° C. for 5 hours. HPLC content: 99.0%. Melting point: 210-215° C., measured by a capillary tube.

The XRPD, TGA, $^1$H NMR, $^{13}$C NMR, IR and DSC thermal analysis spectra of the obtained (S)—[N-3-(3'-fluoro-4'-(4"-phenylpiperazinyl))phenyl-2-oxo-5-oxazolelidinyl]methyl acetamide hydrate are shown in FIGS. 7-13.

Parameters used for obtaining X-ray powder diffraction were: CuKa radiation, 1.54 monochromator, tube voltage 40 KV, tube current 25 mA. The X-ray powder diffraction diagram shows the absorption peaks in the diffraction angles (2θ)=4.07, 7.70, 8.05, 8.42, 10.86, 12.00, 13.38, 14.10, 16.06, 18.56, 20.09, 21.40, 22.08, 23.30, 24.12, 25.10, 25.89, 27.00, 28.37, 28.93, 30.22, 31.28, 32.45, 33.25, 35.35, 36.27, 37.66, 39.45, 40.88, 43.11, 43.69, 45.19, 45.80, 47.24, with ±0.02 2θ for each peak.

The TGA diagram of the resulting crystalline of (S)—[N-3-(3-fluoro-4'-(4"-phenylpiperazinyl))phenyl-2-oxo-5-oxazolelidinyl]methyl acetamide hydrate shows the hydrate contained 2.02% of water (the margin of error for the TGA is ±0.15%). The theoretical value for the 1/2 hydrate is 2.099%.

$^1$H NMR (400 Hz, DMSO-d$_6$) δ: 8.25 (t, 1H), 7.51 (dd, 1H), 7.26~7.18 (m, 3H), 7.12 (t, 1H), 6.99 (d, 2H), 6.81 (t, 1H), 4.74~4.70 (m, 1H), 4.10 (t, 1H), 3.71 (q, 1H), 3.41 (t, 2H), 3.30~3.27 (m, 4H), 3.13~3.11 (m, 4H), 1.84 (s, 3H).

$^{13}$C NMR (400 Hz, DMSO-d$_6$) δ: 170.2, 157.2, 154.2, 152.4, 151.1, 135.7, 133.5, 128.1, 118.6, 118.3, 115.8, 114.2, 107.1, 106.5, 71.7, 50.5, 48.6, 47.5, 22.6. The peak of [M-1/2H$_2$O+H] in the mass spectra is 413.1; the theoretical value is 413.2.

EXAMPLE 3

Preparation of the hemi-hydrate of (S)—[N-3-(3'-fluoro-4'-(4"-phenyl piperazinyl))phenyl-2-oxo-5-oxazolidinyl]methyl acetamide 1 g of (S)—[N-3-(3'-fluoro-4'-(4"-phenyl piperazinyl))phenyl-2-oxo-5-oxazolidinyl]methyl acetamide crude prepared according to Example 1 was dissolved in 2 ml of a mixed solvent (6 wt % hydrochloric acid:ethanol=3:2 (volumetric ratio)). A small amount of activated carbon was added, and the reaction mixture was stirred for 2 hours, filtered. After the filtration, the liquid was left standing at room temperature and crystals formed. The crystals obtained were vacuum dried at 40° C. for 5 hours. The content measured by HPLC: 99.1%.

Figure 14:
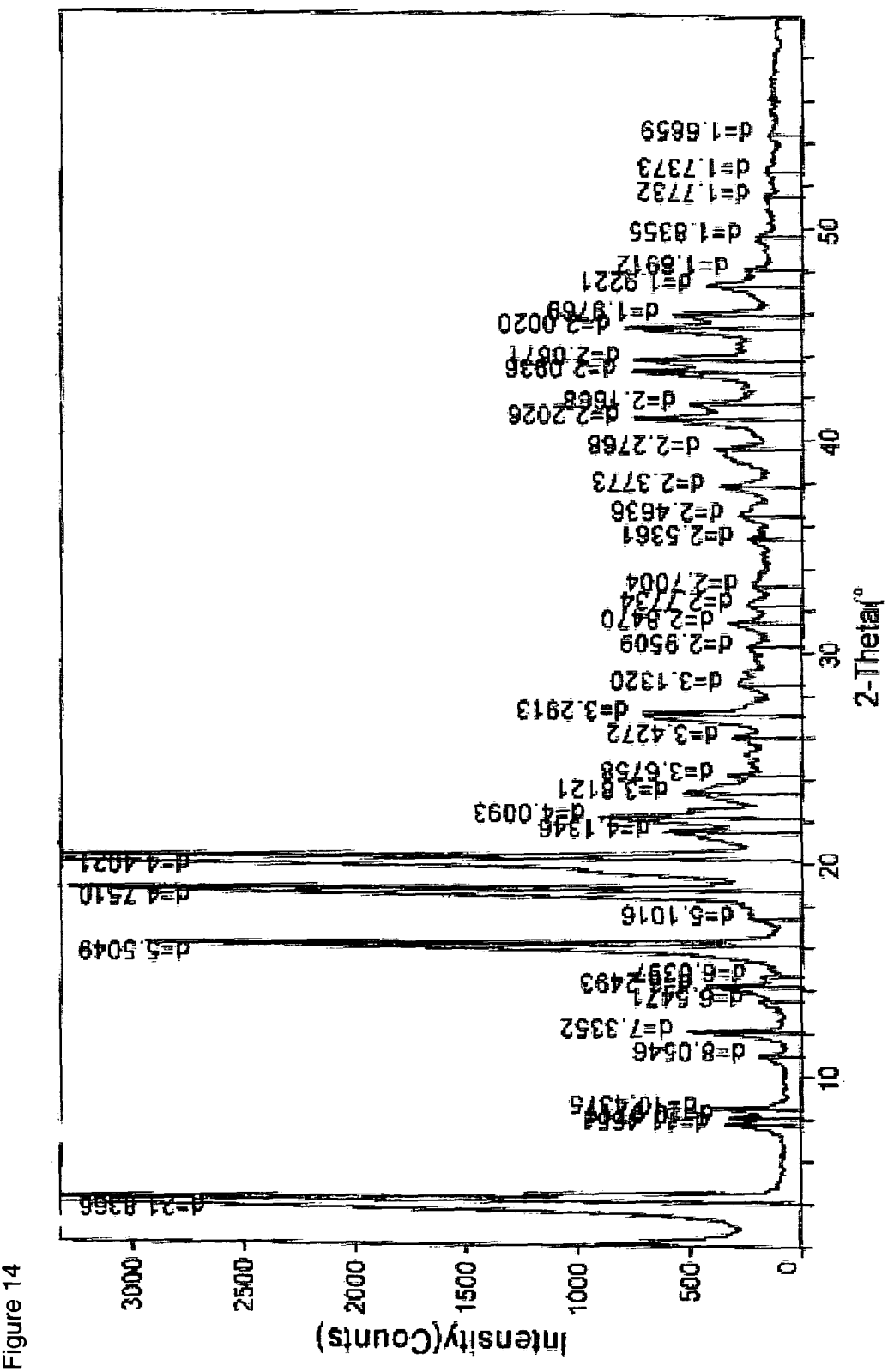
FIG. 14 is the X-ray diffractogram of (S)—[N-3-(3'-fluoro-4'-(4"-phenyl piperazinyl))phenyl-2-oxo-5-oxazolidinyl]methyl acetamide 1/2 hydrate prepared in Example 3.

The conditions for X-ray powder diffraction: CuKa radiation, 1.54 monochromator, tube voltage 40 KV, tube current 25 mA. The X-ray powder diffractogram of the resulting crystal is shown in FIG. 14. In terms of the resulting crystal, the X-ray powder diffraction diagram shows the absorption peaks in the diffraction angles (2θ)=4.04, 7.71, 8.05, 8.46, 10.98, 12.06, 13.51, 14.16, 14.66, 16.09, 17.37, 18.66, 20.16, 21.47, 22.15, 23.32, 24.19, 25.98, 27.07, 28.48, 30.26, 31.40, 32.25, 33.15, 35.36, 36.44, 37.81, 39.55, 40.94, 41.65, 43.17, 43.76, 45.26, 45.86, 47.25, with ±0.02 2θ for each peak.

Figure 7:
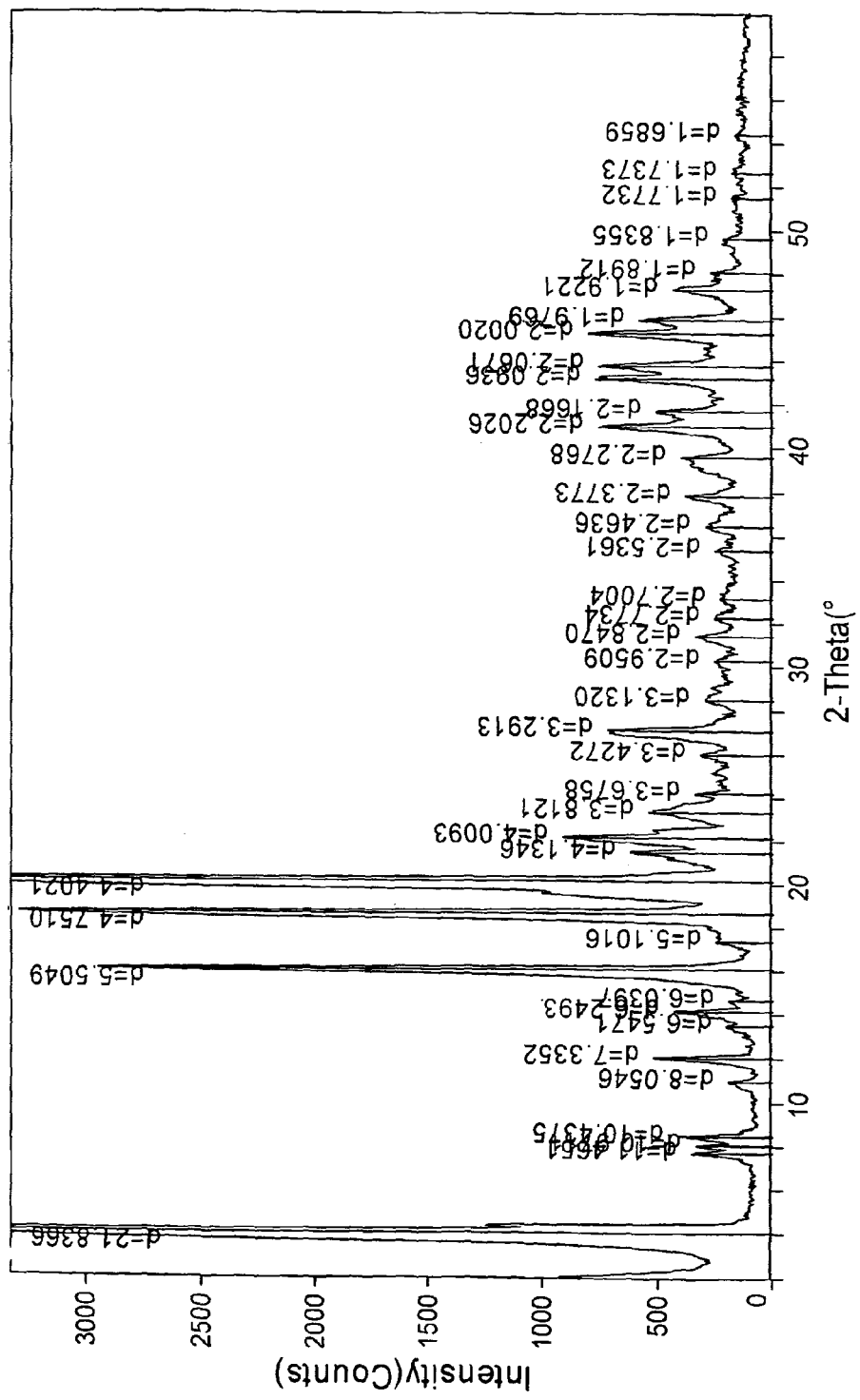
FIG. 7 is the X-ray diffractogram of crystalline (S)—[N-3-(3'-fluoro-4'-(4"-phenyl piperazinyl))phenyl-2-oxo-5-oxazolidinyl]methyl acetamide 1/2 hydrate prepared in Example 2.
Figure 8:
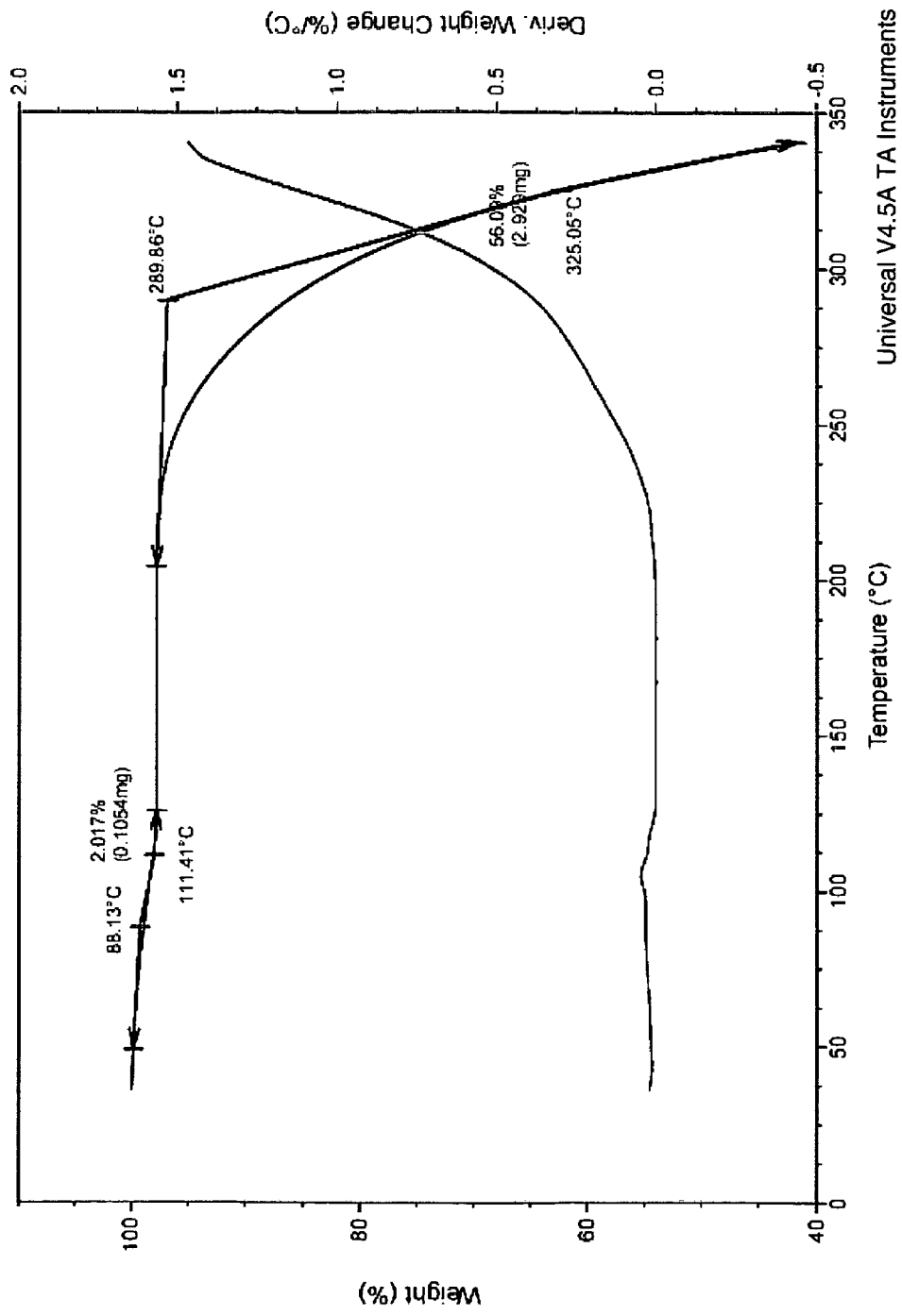
FIG. 8 is the TGA diagram of crystalline (S)—[N-3-(3'-fluoro-4'-(4"-phenyl piperazinyl))phenyl-2-oxo-5-oxazolidinyl]methyl acetamide 1/2 hydrate prepared in Example 2.
Figure 9:
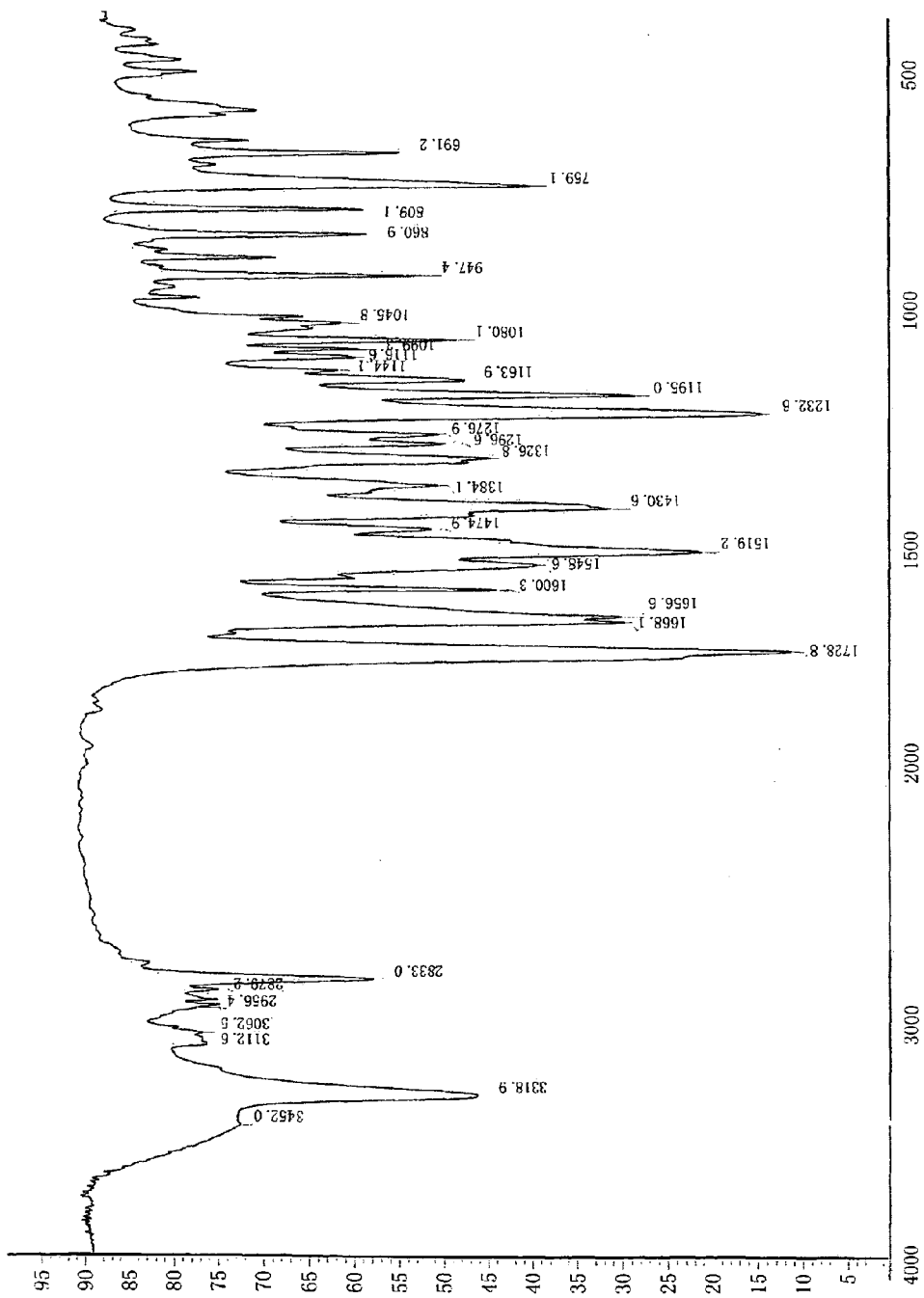
FIG. 9 is the IR spectra of the crystalline (S)—[N-3-(3'-fluoro-4'-(4"-phenyl piperazinyl))phenyl-2-oxo-5-oxazolidinyl]methyl acetamide 1/2 hydrate prepared in Example 2.
Figure 10:
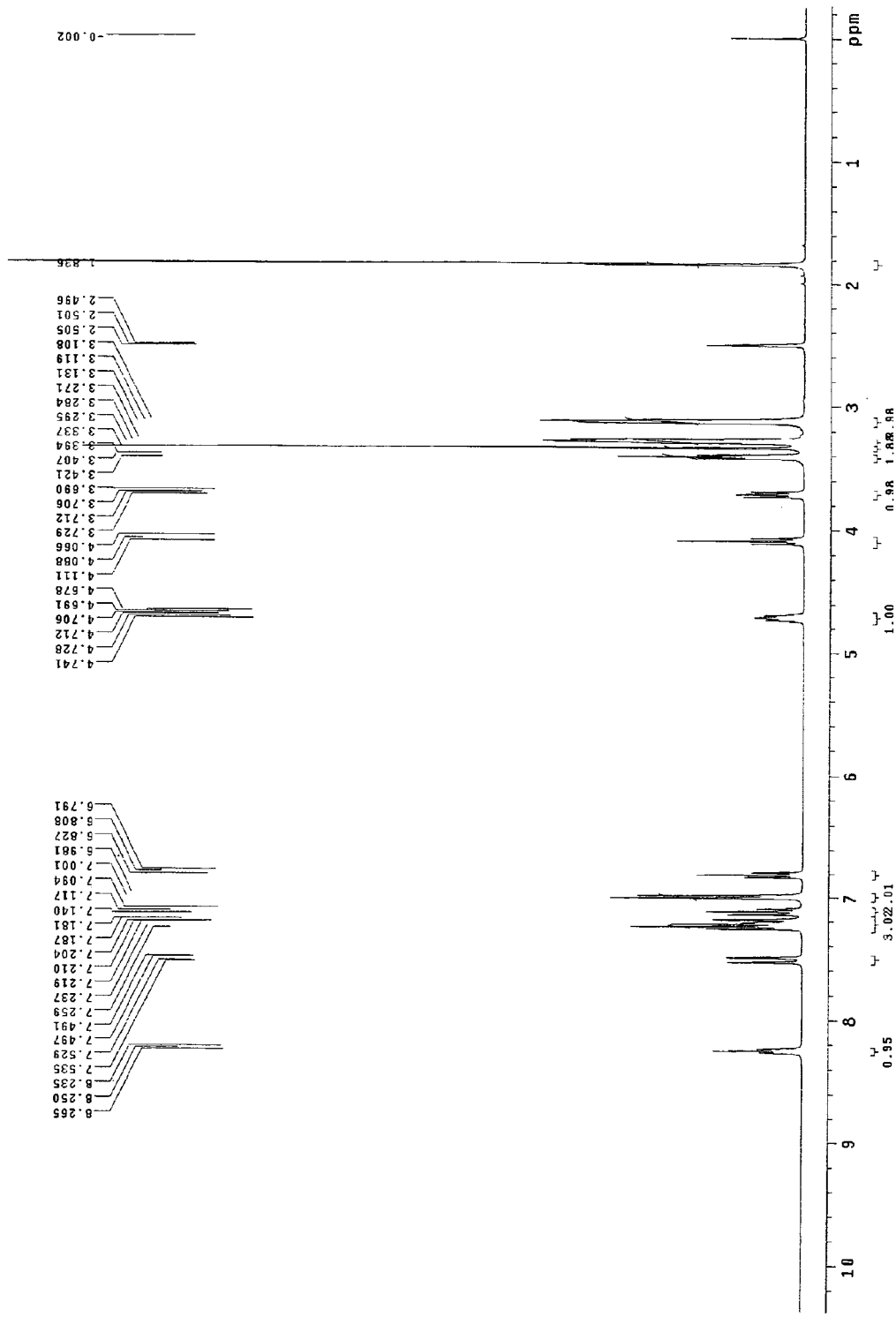
FIG. 10 is the $^1$H-NMR spectra of (S)—[N-3-(3'-fluoro-4'-(4"-phenyl piperazinyl))phenyl-2-oxo-5-oxazolidinyl]methyl acetamide 1/2 hydrate prepared in Example 2.
Figures 1, 10:
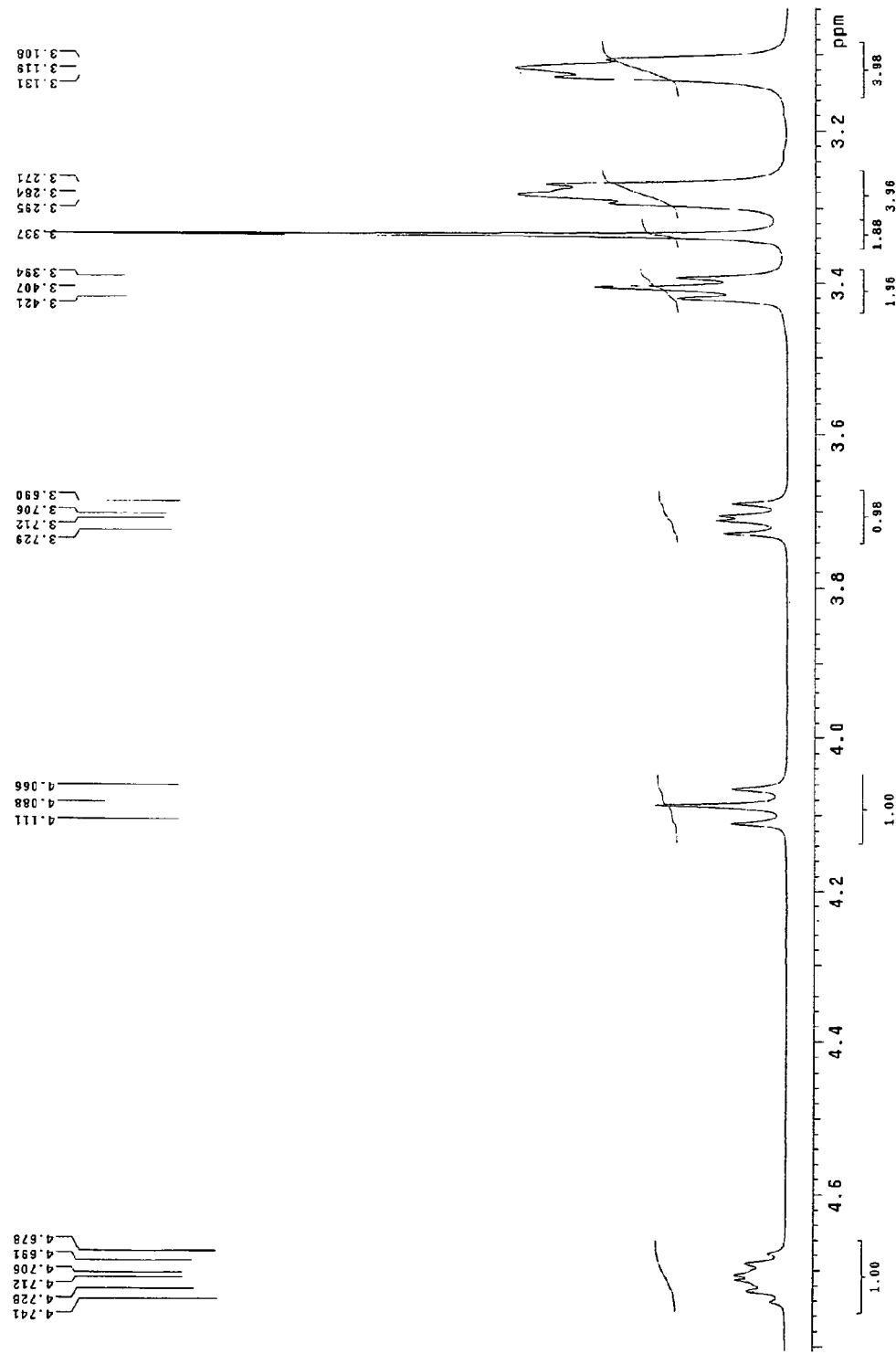
Figures 2, 10:
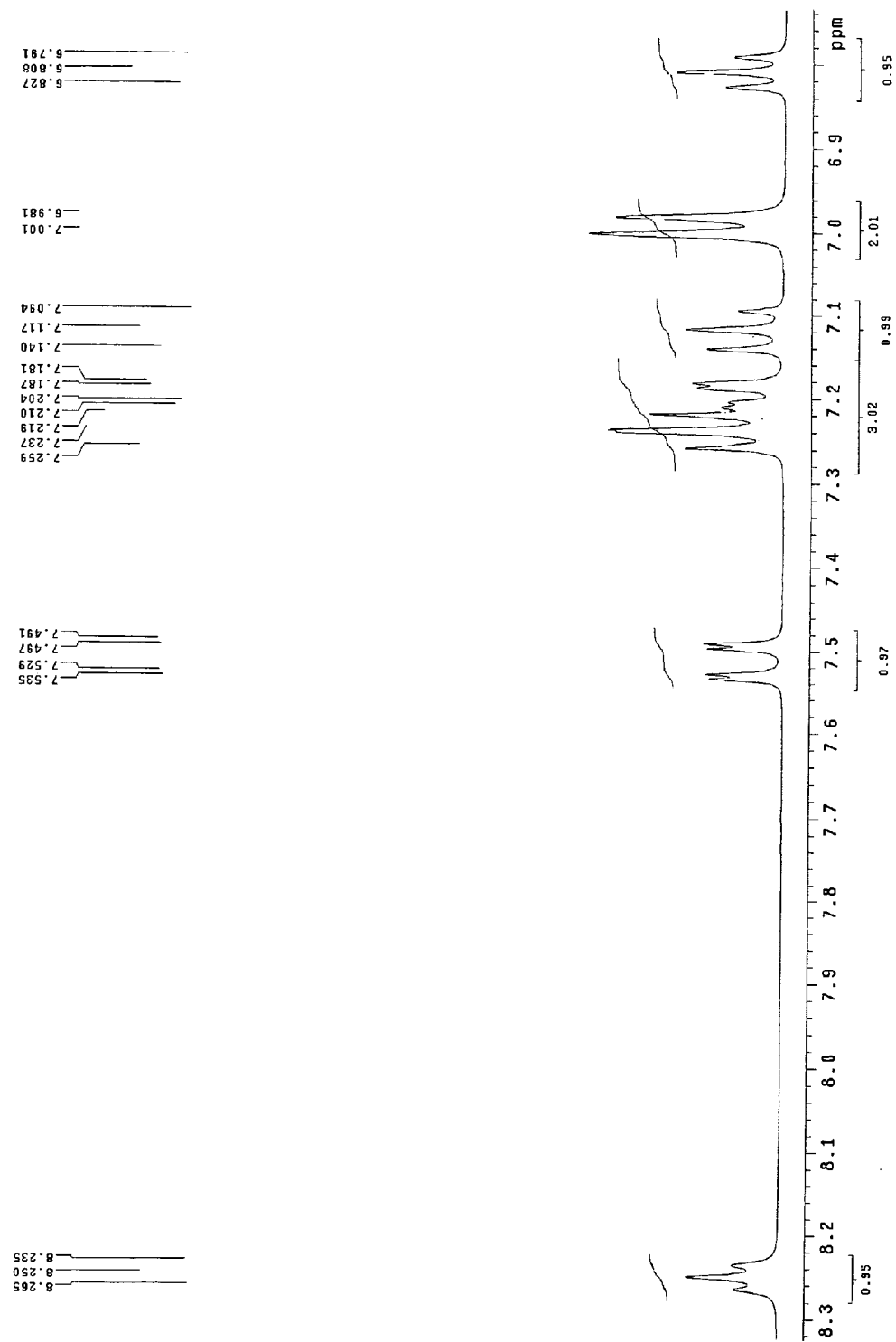
Figure 11:
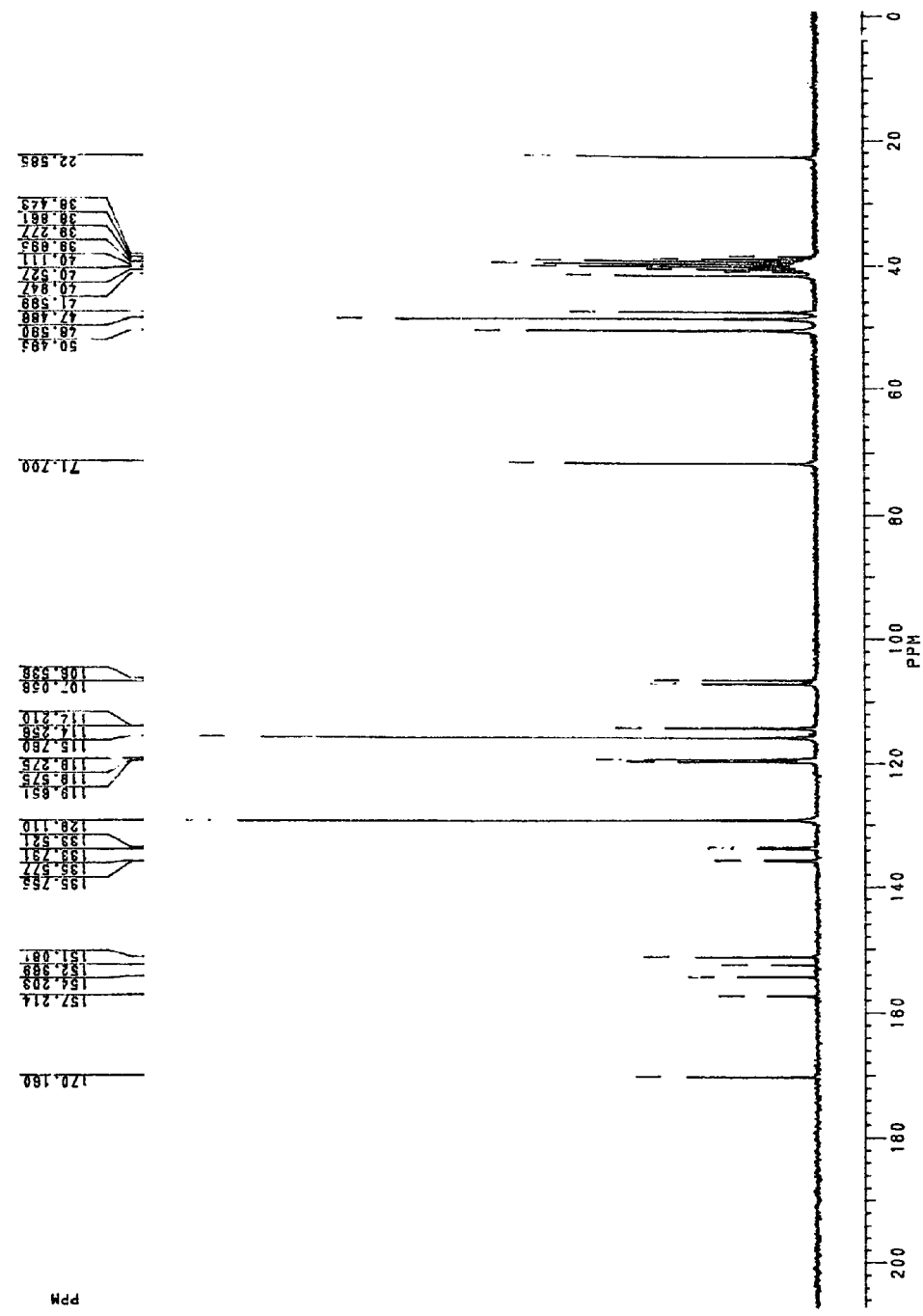
FIG. 11 is the $^{13}$C-NMR spectra of (S)—[N-3-(3'-fluoro-4'-(4"-phenyl piperazinyl))phenyl-2-oxo-5-oxazolidinyl]methyl acetamide hydrate prepared in Example 2.
Figures 1, 11:
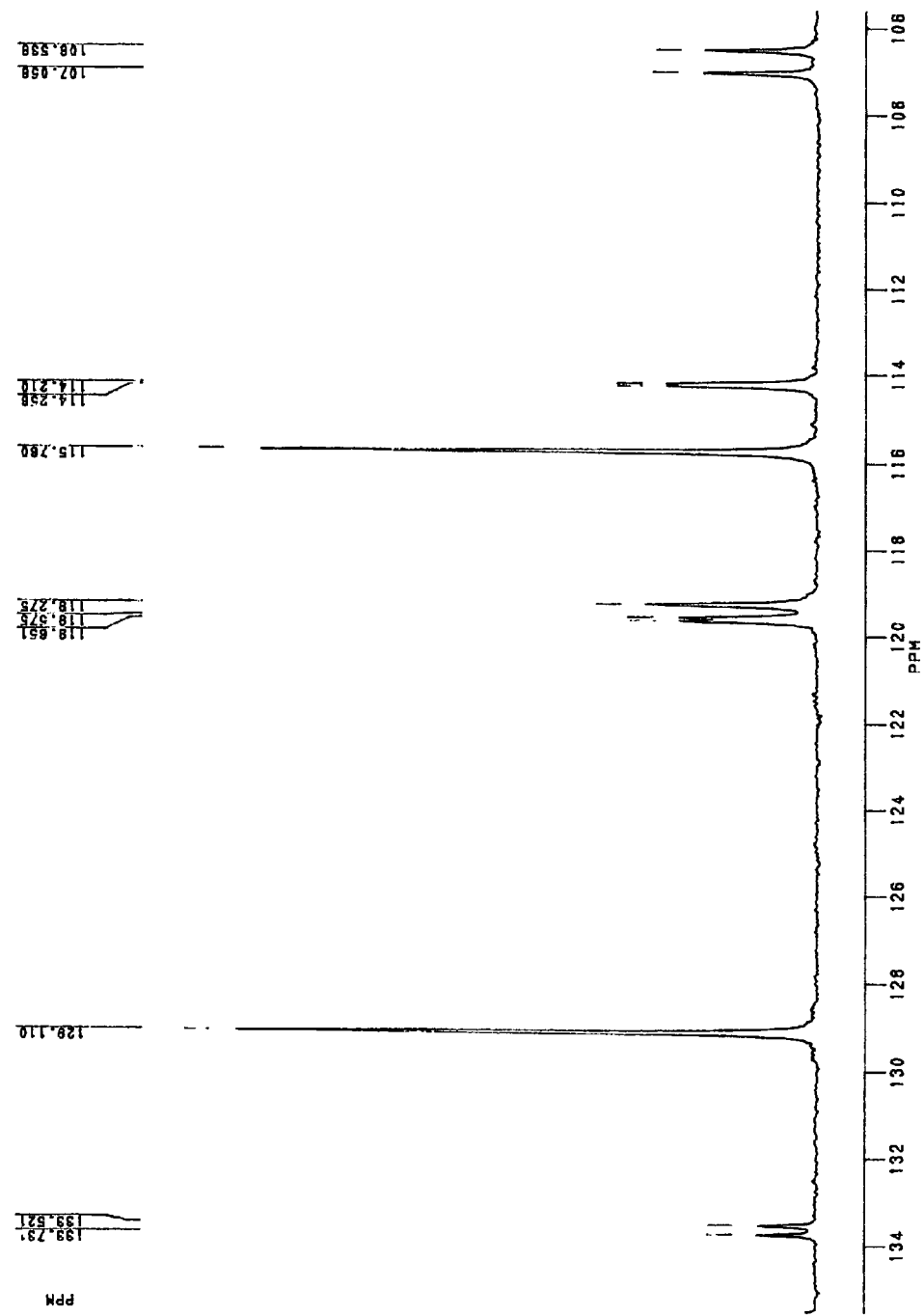
Figure 12:
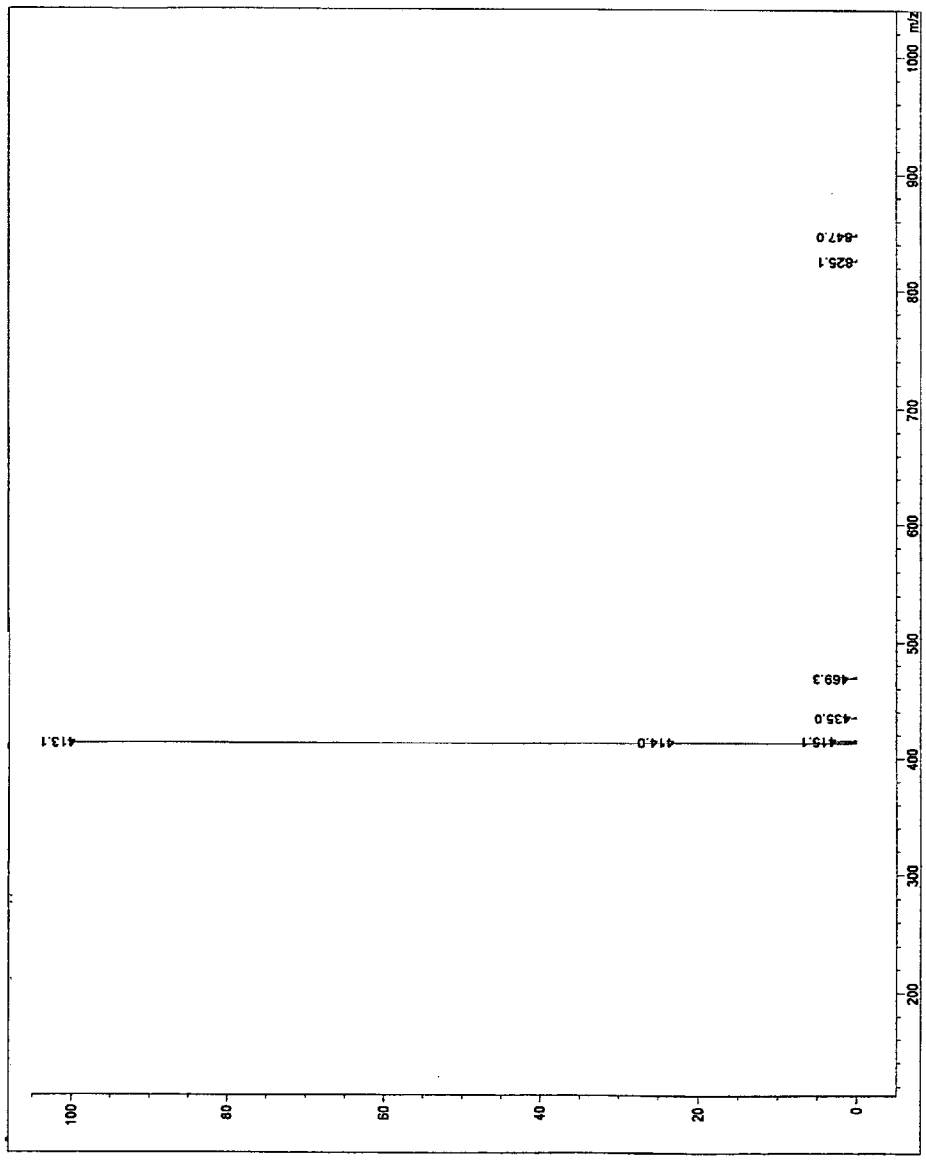
FIG. 12 is the mass spectrum of (S)—[N-3-(3'-fluoro-4'-(4"-phenyl piperazinyl))phenyl-2-oxo-5-oxazolidinyl]methyl acetamide 1/2 hydrate prepared in Example 2.
Figure 13:
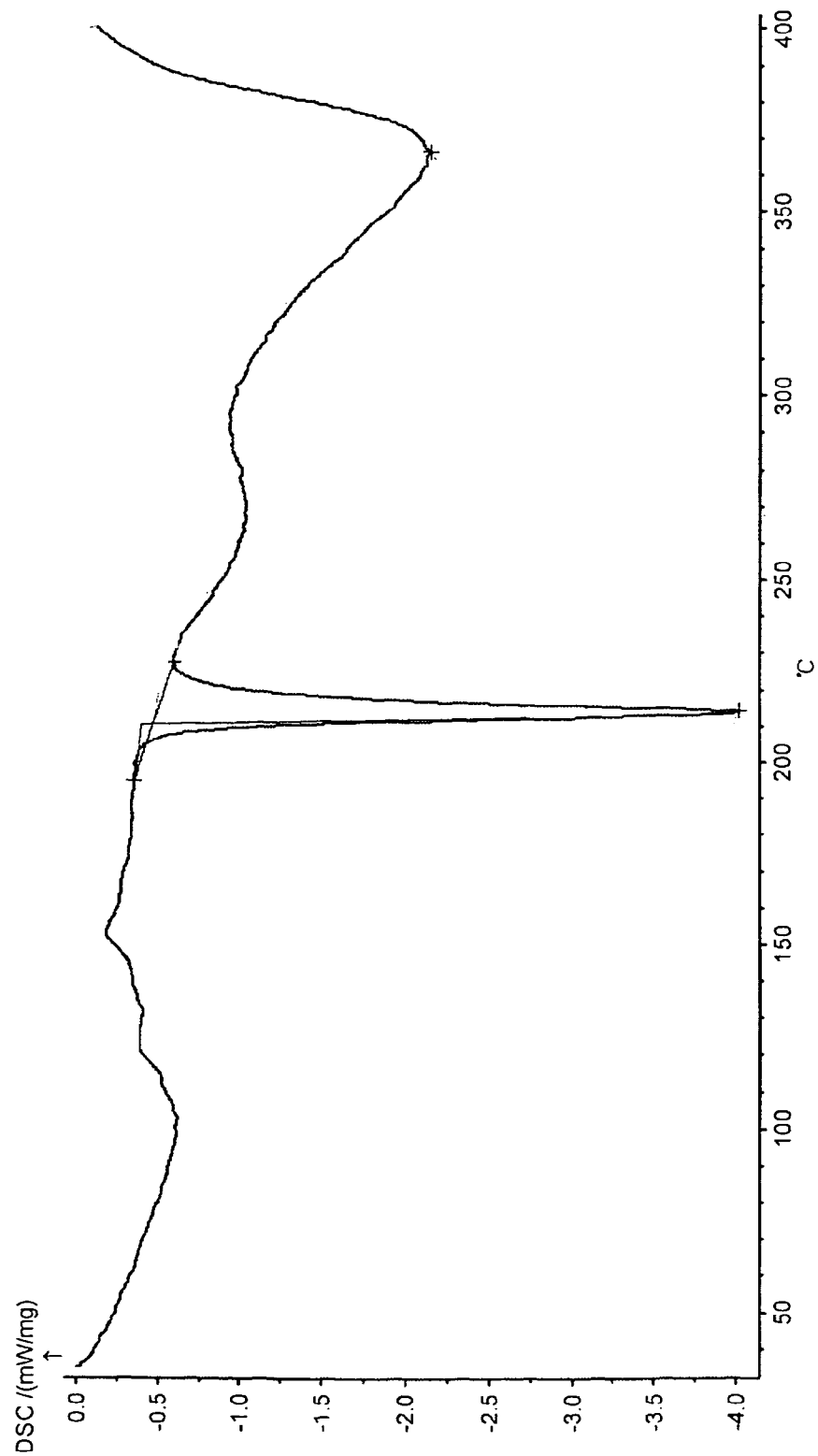
FIG. 13 is the DSC spectra of (S)—[N-3-(3'-fluoro-4'-(4"-phenyl piperazinyl))phenyl-2-oxo-5-oxazolidinyl]methyl acetamide 1/2 hydrate prepared in Example 2.

By comparing the X-ray powder ("XRPD") diffractograms from Examples 1-3, one skilled in the analysis of XRPD would find that significant differences exist between the XRPD diagram of Example 1 (anhydrous, FIG. 1) and those of Examples 2 and 3 (1/2 hydrate, FIGS. 7 and 14). Also, the XRPD diagrams show that the hydrates produced in Examples 2 and 3 are the same, indicating that either acidic solvent alone or a mixed solvent comprising an acidic solvent and an organic solvent can be used to prepare the 1/2 hydrate.

The following examples show different processes for the preparation of the 1/2 hydrate of (S)—[N-3-(3'-fluoro-4'-(4"-phenyl piperazinyl))phenyl-2-oxo-5-oxazolidinyl]methyl acetamide.

EXAMPLES 4-105

Preparation of (S)—[N-3-(3'-fluoro-4'-(4"-phenyl piperazinyl))phenyl-2-oxo-5-oxazolidinyl]methyl acetamide 1/2 hydrate (C$_{22}$H$_{25}$N$_4$O$_3$.1/2H$_2$O)

(S)—[N-3-(3'-fluoro-4'-(4"-phenyl piperazinyl))phenyl-2-oxo-5-oxazolidinyl]methyl acetamide 1/2 hydrates were prepared according to the conditions listed in Table 1. The TGA and the melting temperature of the compounds prepared in Examples 4-105 were sufficiently similar to the TGA and the melting point of the 1/2 hydrates prepared in Examples 2 and 3 to be consistent with the conclusion that all were the 1/2 hydrate.

TABLE 1

| | | | Preparation of ½ hydrate (Examples 2-105) | | | | | | | |
|---|---|---|---|---|---|---|---|---|---|---|
| | Amount of the crude | | | Solvent | | Stirring conditions | | | | |
| Ex. | material (g) | pH$^a$ | Solvent | Volume ratio | Amount (ml) | T (° C.) | Time (hr) | Other | purity % | yield % |
| 2 | 1 | / | 6% hydrochloric acid aqueous solution | / | 2 | 50 | 2 | activated carbon added | 99.0 | 43 |
| 3 | 1 | / | 6% hydrochloric acid aqueous solution:ethanol | 3:2 | 2 | 50 | 2 | activated carbon added | 99.1 | 50 |

TABLE 1-continued

Preparation of ½ hydrate (Examples 2-105)

| Ex. | Amount of the crude material (g) | pH$^a$ | Solvent | Solvent Volume ratio | Solvent Amount (ml) | Stirring conditions T (° C.) | Stirring conditions Time (hr) | Other | purity % | yield % |
|---|---|---|---|---|---|---|---|---|---|---|
| 4 | 10 | 1 | hydrochloric acid aqueous solution:ethanol | 6:4 | 80 | 45 | 5 | activated carbon added | 99.4 | 55 |
| 5 | 10 | 1 | hydrochloric acid aqueous solution:ethanol | 5:5 | 80 | 35 | 5 | | 99.6 | 60 |
| 6 | 10 | 2 | hydrochloric acid aqueous solution:ethanol | 6:4 | 60 | 30 | 7 | activated carbon added | 99.3 | 50 |
| 7 | 10 | 2 | hydrochloric acid aqueous solution:ethanol | 2:8 | 60 | 50 | 5 | allowed to stand to crystallize | 99.5 | 65 |
| 8 | 10 | 3 | hydrochloric acid aqueous solution:ethanol | 3:7 | 50 | 60 | 4 | poured into water to crystallize | 99.3 | 56 |
| 9 | 10 | 3 | hydrochloric acid aqueous solution:ethanol | 2:8 | 50 | 70 | 3 | activated carbon added | 99.2 | 65 |
| 10 | 10 | 4 | hydrochloric acid aqueous solution:ethanol | 7:3 | 100 | 80 | 2 | | 99.0 | 45 |
| 11 | 10 | 4 | hydrochloric acid aqueous solution:ethanol | 4:6 | 100 | 70 | 3 | activated carbon added | 99.2 | 52 |
| 12 | 10 | 5 | hydrochloric acid aqueous solution:ethanol | 8:2 | 120 | 60 | 3 | | 99.5 | 55 |
| 13 | 10 | 5 | hydrochloric acid aqueous solution:ethanol | 5:5 | 120 | 45 | 5 | | 99.6 | 48 |
| 14 | 10 | 1 | sulfuric acid aqueous solution:ethanol | 6:4 | 70 | 45 | 5 | activated carbon added | 99.3 | 61 |
| 15 | 10 | 2 | sulfuric acid aqueous solution:ethanol | 2:8 | 70 | 50 | 5 | allowed to stand to crystallize | 99.0 | 70 |
| 16 | 10 | 4 | sulfuric acid aqueous solution:ethanol | 7:3 | 100 | 80 | 2 | | 99.5 | 55 |
| 17 | 10 | 5 | sulfuric acid aqueous solution:ethanol | 8:2 | 120 | 60 | 3 | | 99.0 | 45 |
| 18 | 10 | 1 | phosphoric acid aqueous solution:methanol | 6:4 | 70 | 45 | 5 | activated carbon added | 99.3 | 60 |
| 19 | 10 | 1 | phosphoric acid aqueous solution:ethanol | 5:5 | 80 | 35 | 5 | | 99.4 | 60 |
| 20 | 10 | 2 | phosphoric acid aqueous solution:acetonitrile | 6:4 | 80 | 30 | 7 | activated carbon added | 99.2 | 40 |
| 21 | 10 | 2 | phosphoric acid aqueous solution:acetonitrile | 2:8 | 70 | 50 | 5 | allowed to stand to crystallize | 99.2 | 70 |
| 22 | 10 | 3 | perchloric acid aqueous solution:ethanol | 3:7 | 90 | 60 | 4 | | 99.0 | 70 |
| 23 | 10 | 3 | perchloric acid aqueous solution:ethyl acetate | 2:8 | 100 | 70 | 3 | activated carbon added | 99.3 | 58 |
| 24 | 10 | 4 | perchloric acid aqueous solution:petroleum ether | 7:3 | 100 | 80 | 2 | | 99.6 | 60 |
| 25 | 10 | 4 | permanganic acid aqueous solution:ethanol | 4:6 | 100 | 70 | 3 | activated carbon added | 98.9 | 80 |
| 26 | 10 | 1 | hydrobromic acid aqueous solution:methanol | 6:4 | 70 | 45 | 5 | activated carbon added | 99.5 | 70 |

TABLE 1-continued

Preparation of ½ hydrate (Examples 2-105)

| Ex. | Amount of the crude material (g) | pH$^a$ | Solvent | Volume ratio | Amount (ml) | T (° C.) | Time (hr) | Other | purity % | yield % |
|---|---|---|---|---|---|---|---|---|---|---|
| 27 | 10 | 1 | hydrobromic acid aqueous solution:ethanol | 5:5 | 80 | 35 | 5 | | 99.3 | 45 |
| 28 | 10 | 2 | hydrobromic acid aqueous solution:acetonitrile | 6:4 | 80 | 30 | 7 | activated carbon added | 99.2 | 50 |
| 29 | 10 | 3 | nitric acid aqueous solution:ethanol | 3:7 | 90 | 60 | 4 | poured into water to crystallize | 99.6 | 55 |
| 30 | 10 | 3 | nitric acid aqueous solution:ethyl acetate | 2:8 | 100 | 70 | 3 | activated carbon added | 99.5 | 65 |
| 31 | 10 | 4 | formic acid aqueous solution:ethanol | 4:6 | 100 | 70 | 3 | activated carbon added | 99.6 | 60 |
| 32 | 10 | 5 | acetic acid aqueous solution:ethyl acetate | 8:2 | 120 | 60 | 3 | | 99.4 | 53 |
| 33 | 10 | 5 | acetic acid aqueous solution:methanol | 5:5 | 120 | 45 | 5 | | 99.5 | 62 |
| 34 | 10 | 3 | oxalic acid aqueous solution:methanol | 6:4 | 70 | 45 | 5 | activated carbon added | 99.0 | 53 |
| 35 | 10 | 4 | oxalic acid aqueous solution:ethanol | 5:5 | 80 | 35 | 5 | | 99.6 | 54 |
| 36 | 10 | 3 | maleic acid aqueous solution:acetonitrile | 2:8 | 70 | 50 | 5 | allowed to stand to crystallize | 99.4 | 63 |
| 37 | 10 | 3 | maleic acid aqueous solution:ethanol | 3:7 | 90 | 60 | 4 | poured into water to crystallize | 99.2 | 60 |
| 38 | 10 | 4 | maleic acid aqueous solution:ethyl acetate | 2:8 | 100 | 70 | 3 | activated carbon added | 99.5 | 45 |
| 39 | 10 | 4 | trifluoroacetic acid aqueous solution:ethanol | 4:6 | 100 | 70 | 3 | activated carbon added | 99.5 | 55 |
| 40 | 10 | 5 | trifluoroacetic acid aqueous solution:ethyl acetate | 8:2 | 120 | 60 | 3 | | 99.4 | 61 |
| 41 | 10 | 3 | dichloroacetic acid aqueous solution:methanol | 6:4 | 70 | 45 | 5 | | 99.7 | 60 |
| 42 | 10 | 4 | dichloroacetic acid aqueous solution:ethanol | 5:5 | 80 | 35 | 5 | | 99.4 | 53 |
| 43 | 10 | 3 | dichloroacetic acid aqueous solution:acetonitrile | 2:8 | 70 | 50 | 5 | allowed to stand to crystallize | 99.6 | 58 |
| 44 | 10 | 3 | dichloroacetic acid aqueous solution:ethanol | 3:7 | 90 | 60 | 4 | poured into water to crystallize | 99.0 | 60 |
| 45 | 10 | 4 | dichloroacetic acid aqueous solution:tetrahydrofuran | 2:8 | 100 | 70 | 3 | activated carbon added | 99.0 | 59 |
| 46 | 10 | 4 | trifluoroacetic acid aqueous solution:tetrahydrofuran | 7:3 | 100 | 80 | 2 | | 99.3 | 68 |
| 47 | 10 | 4 | trifluoroacetic acid aqueous solution:tetrahydrofuran | 4:6 | 100 | 70 | 3 | activated carbon added | 99.2 | 65 |
| 48 | 10 | 5 | citric acid aqueous solution:ethyl acetate | 8:2 | 120 | 60 | 3 | | 99.1 | 45 |

TABLE 1-continued

Preparation of ½ hydrate (Examples 2-105)

| Ex. | Amount of the crude material (g) | pH[a] | Solvent | Volume ratio | Amount (ml) | T (°C.) | Time (hr) | Other | purity % | yield % |
|---|---|---|---|---|---|---|---|---|---|---|
| 49 | 10 | 5 | citric acid aqueous solution:methanol | 5:5 | 120 | 45 | 5 | | 99.4 | 60 |
| 50 | 10 | 4 | hydrochloric acid aqueous solution:ethanol:methanol | 6:2:2 | 100 | 40 | 5 | | 99.5 | 55 |
| 51 | 10 | 5 | hydrochloric acid aqueous solution:ethanol:methanol | 6:3:1 | 100 | 70 | 2 | activated carbon added | 99.6 | 54 |
| 52 | 10 | 2 | sulfuric acid aqueous solution:ethanol:methanol | 6:3:1 | 100 | 30 | 5 | activated carbon added | 99.6 | 47 |
| 53 | 10 | 1 | hydrochloric acid aqueous solution | | 60 | 45 | 5 | activated carbon added | 98.9 | 60 |
| 54 | 10 | 1 | hydrochloric acid aqueous solution | | 80 | 35 | 5 | | 99.3 | 55 |
| 55 | 10 | 2 | hydrochloric acid aqueous solution | | 90 | 30 | 7 | activated carbon added | 99.0 | 69 |
| 56 | 10 | 2 | hydrochloric acid aqueous solution | | 80 | 50 | 5 | allowed to stand to crystallize | 99.5 | 60 |
| 57 | 10 | 3 | hydrochloric acid aqueous solution | | 60 | 60 | 4 | poured into water to crystallize | 99.5 | 61 |
| 58 | 10 | 3 | hydrochloric acid aqueous solution | | 60 | 70 | 3 | activated carbon added | 99.1 | 66 |
| 59 | 10 | 4 | hydrochloric acid aqueous solution | | 100 | 80 | 2 | | 99.6 | 41 |
| 60 | 10 | 4 | hydrochloric acid aqueous solution | | 100 | 70 | 3 | activated carbon added | 99.5 | 50 |
| 61 | 10 | 5 | hydrochloric acid aqueous solution | | 120 | 60 | 3 | | 99.3 | 65 |
| 62 | 10 | 5 | hydrochloric acid aqueous solution | | 120 | 45 | 5 | | 99.2 | 68 |
| 63 | 10 | 1 | sulfuric acid aqueous solution | | 80 | 45 | 5 | activated carbon added | 99.3 | 51 |
| 64 | 10 | 1 | sulfuric acid aqueous solution | | 90 | 35 | 5 | | 99.2 | 64 |
| 65 | 10 | 2 | sulfuric acid aqueous solution | | 90 | 30 | 7 | activated carbon added | 99.5 | 61 |
| 66 | 10 | 2 | sulfuric acid aqueous solution | | 80 | 50 | 5 | placed and crystallized | 99.6 | 54 |
| 67 | 10 | 3 | sulfuric acid aqueous solution | | 100 | 60 | 4 | poured into water to crystallize | 99.5 | 41 |
| 68 | 10 | 3 | sulfuric acid aqueous solution | | 110 | 70 | 3 | activated carbon added | 99.1 | 41 |
| 69 | 10 | 4 | sulfuric acid aqueous solution | | 110 | 80 | 2 | | 98.9 | 69 |
| 70 | 10 | 5 | sulfuric acid aqueous solution | | 120 | 60 | 3 | | 99.0 | 70 |
| 71 | 10 | 5 | sulfuric acid aqueous solution | | 120 | 45 | 5 | | 99.5 | 61 |
| 72 | 10 | 1 | phosphoric acid aqueous solution | | 80 | 45 | 5 | | 99.2 | 66 |
| 73 | 10 | 1 | phosphoric acid aqueous solution | | 80 | 35 | 5 | | 99.5 | 61 |
| 74 | 10 | 2 | phosphoric acid aqueous solution | | 80 | 50 | 5 | | 99.6 | 51 |
| 75 | 10 | 3 | perchloric acid aqueous solution | | 100 | 60 | 4 | poured into water to crystallize | 99.2 | 55 |
| 76 | 10 | 3 | perchloric acid aqueous solution | | 100 | 70 | 3 | | 99.0 | 41 |
| 77 | 10 | 4 | permanganic acid aqueous solution | | 110 | 70 | 3 | activated carbon added | 99.1 | 44 |

TABLE 1-continued

Preparation of ½ hydrate (Examples 2-105)

| Ex. | Amount of the crude material (g) | pH$^a$ | Solvent | Volume ratio | Amount (ml) | T (°C.) | Time (hr) | Other | purity % | yield % |
|---|---|---|---|---|---|---|---|---|---|---|
| 78 | 10 | 5 | permanganic acid aqueous solution | | 120 | 45 | 5 | | 99.6 | 52 |
| 79 | 10 | 1 | hydrobromic acid aqueous solution | | 80 | 45 | 5 | activated carbon added | 99.1 | 56 |
| 80 | 10 | 1 | hydrobromic acid aqueous solution | | 90 | 35 | 5 | | 99.5 | 45 |
| 81 | 10 | 2 | hydrobromic acid aqueous solution | | 90 | 30 | 7 | activated carbon added | 99.2 | 65 |
| 82 | 10 | 2 | nitric acid aqueous solution | | 70 | 50 | 5 | allowed to stand to crystallize | 99.0 | 70 |
| 83 | 10 | 3 | nitric acid aqueous solution | | 110 | 70 | 3 | activated carbon added | 99.2 | 67 |
| 84 | 10 | 4 | formic acid aqueous solution | | 100 | 80 | 2 | | 99.5 | 61 |
| 85 | 10 | 4 | formic acid aqueous solution | | 100 | 70 | 3 | activated carbon added | 99.3 | 68 |
| 86 | 10 | 5 | acetic acid aqueous solution | | 120 | 60 | 3 | | 98.8 | 61 |
| 87 | 10 | 5 | acetic acid aqueous solution | | 120 | 45 | 5 | | 99.5 | 61 |
| 88 | 10 | 3 | oxalic acid aqueous solution | | 80 | 45 | 5 | activated carbon added | 99.3 | 56 |
| 89 | 10 | 5 | oxalic acid aqueous solution | | 80 | 30 | 7 | activated carbon added | 99.0 | 65 |
| 90 | 10 | 3 | maleic acid aqueous solution | | 80 | 50 | 5 | allowed to stand to crystallize | 99.5 | 55 |
| 91 | 10 | 3 | maleic acid aqueous solution | | 100 | 60 | 4 | | 99.5 | 61 |
| 92 | 10 | 4 | trifluoroacetic acid aqueous solution | | 100 | 80 | 2 | | 99.6 | 50 |
| 93 | 10 | 4 | trifluoroacetic acid aqueous solution | | 110 | 70 | 3 | activated carbon added | 99.2 | 69 |
| 94 | 10 | 5 | trifluoroacetic acid aqueous solution | | 120 | 60 | 3 | | 99.5 | 51 |
| 95 | 10 | 5 | trifluoroacetic acid aqueous solution | | 120 | 45 | 5 | | 99.6 | 48 |
| 96 | 10 | 3 | dichloroacetate aqueous solution | | 80 | 45 | 5 | | 99.2 | 66 |
| 97 | 10 | 5 | dichloroacetate aqueous solution | | 90 | 30 | 7 | activated carbon added | 99.3 | 68 |
| 98 | 10 | 3 | dichloroacetate aqueous solution | | 80 | 50 | 5 | | 99.5 | 61 |
| 99 | 10 | 3 | chloroacetic acid aqueous solution | | 100 | 60 | 4 | | 99.1 | 52 |
| 100 | 10 | 5 | citric acid aqueous solution | | 120 | 60 | 3 | | 99.6 | 60 |
| 101 | 10 | 5 | citric acid aqueous solution | | 120 | 45 | 5 | | 99.5 | 61 |
| 102 | 10 | 2:2 | hydrochloric acid aqueous solution:sulfuric acid aqueous solution:ethyl acetate:petroleum ether | 2:1:5:2 | 100 | 70 | 2 | | 99.3 | 55 |
| 103 | 10 | 2 | citric acid aqueous solution:ethyl acetate:ethanol | 3:1:6 | 100 | 60 | 4 | | 99.0 | 59 |

TABLE 1-continued

Preparation of ½ hydrate (Examples 2-105)

| Ex. | Amount of the crude material (g) | pH[a] | Solvent | Volume ratio | Amount (ml) | T (°C.) | Time (hr) | Other | purity % | yield % |
|---|---|---|---|---|---|---|---|---|---|---|
| 104 | 10 | 2 | citric acid aqueous solution:ethyl acetate:ethanol:acetonitrile | 6:2:1:1 | 80 | 70 | 5 | | 99.6 | 45 |
| 105 | 1 | / | 50% hydrochloric acid aqueous solution | | 1 | 45 | 1 | activated carbon added | 98.8 | 40 |

[a] The pH value is the pH value of the acidic solution used for the preparation of the solvent.

EXAMPLES 106-161

Preparation of (S)—[N-3-(3'-fluoro-4'-(4"-phenyl piperazinyl))phenyl-2-oxo-5-oxazolidinyl]methyl acetamide 2/7 hydrate ($C_{22}H_{25}N_4O_3 \cdot 2/7 H_2O$)

As shown in Table 2, a solution of (S)—[N-3-(3'-fluoro-4'-(4"-phenyl piperazinyl))phenyl-2-oxo-5-oxazolidinyl]methyl acetamide was prepared by mixing 10 g of (S)—[N-3-(3'-fluoro-4'-(4"-phenyl piperazinyl))phenyl-2-oxo-5-oxazolidinyl]methyl acetamide prepared according to Example 1 with 200 ml of a mixed solvent containing water and an organic solvent. The solution was then stirred, filtered, and crystallized according to the conditions listed in Table 2.

Figure 15:
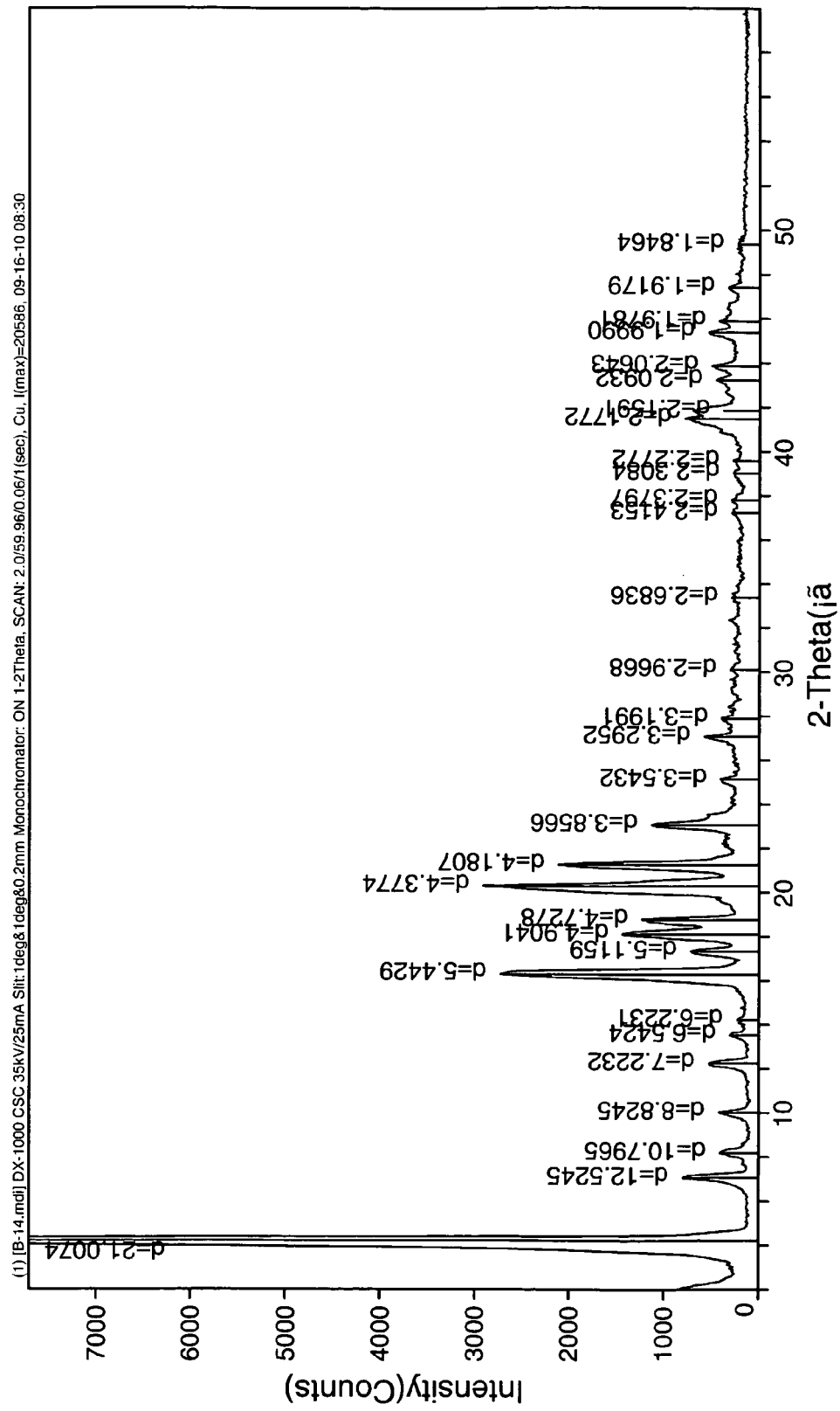
FIG. 15 is the X-ray diffractogram of the (S)—[N-3-(3'-fluoro-4'-(4"-phenyl piperazinyl))phenyl-2-oxo-5-oxazolidinyl]methyl acetamide 2/7 hydrate prepared in Example 106.
Figure 16:
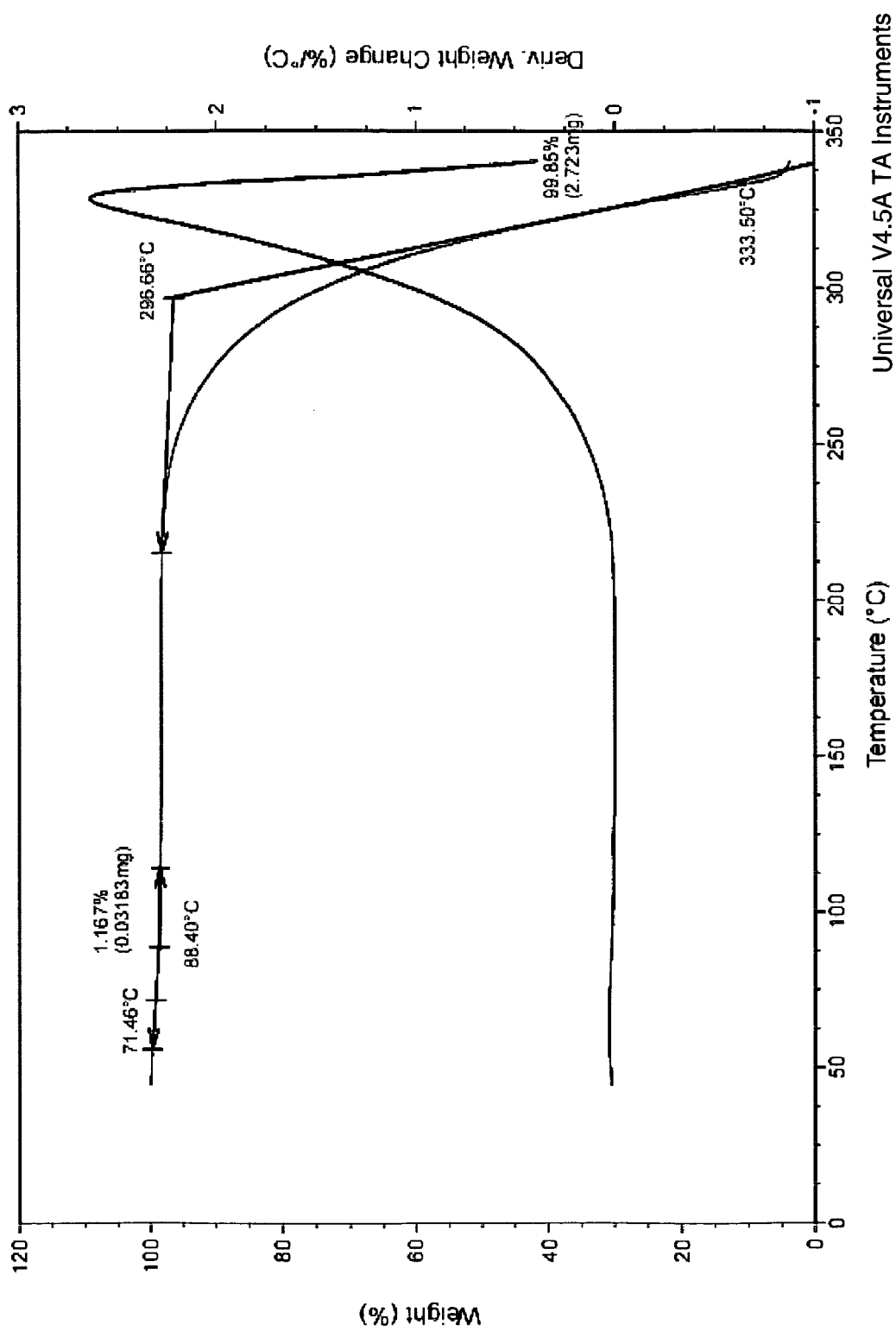
FIG. 16 is the TGA diagram of (S)—[N-3-(3'-fluoro-4'-(4"-phenyl piperazinyl))phenyl-2-oxo-5-oxazolidinyl]methyl acetamide 2/7 hydrate prepared in Example 106.

The crystalline compound obtained in Example 106 had a melting temperature of 210-215° C. measured by a capillary tube, and its XRPD and TGA analysis are shown in FIGS. 15 and 16. TGA data shows that the water content of crystalline compound in Example 106 was 1.20±0.15%, indicating that the crystalline compound was a 2/7 hydrate of (S)—[N-3-(3'-fluoro-4'-(4"-phenyl piperazinyl))phenyl-2-oxo-5-oxazolidinyl]methyl acetamide. The TGA and the melting temperature of the crystalline compounds prepared in Examples 107-161 were sufficiently similar to the TGA and the melting point of the 2/7 hydrate prepared in Example 106 to be consistent with the conclusion that all were the 2/7 hydrate prepared in Example 106.

TABLE 2

Preparation of the 2/7 hydrate (Examples 106~161)

| Ex. | Amount of the crude material (g) | Mixture of organic solvent and water | Volume ratio | Amount (ml) | T (° C.) | Time (hr) | Purity % | Yield % |
|---|---|---|---|---|---|---|---|---|
| 106 | 10 | water:ethyl acetate | 2:8 | 200 | 30 | 8 | 98.8 | 51 |
| 107 | 10 | water:ethyl acetate | 8:2 | 200 | 45 | 7 | 99.0 | 48 |
| 108 | 10 | water:ethyl acetate | 3:7 | 200 | 50 | 7 | 98.7 | 53 |
| 109 | 10 | water:ethyl acetate | 7:3 | 200 | 60 | 5 | 98.8 | 50 |
| 110 | 10 | water:ethyl acetate | 4:6 | 200 | 70 | 4 | 98.9 | 47 |
| 111 | 10 | water:ethyl acetate | 6:4 | 200 | 80 | 3 | 98.9 | 49 |
| 112 | 10 | water:ethyl acetate | 5:5 | 200 | 55 | 6 | 99.2 | 48 |
| 113 | 10 | water:methyl acetate | 2:8 | 200 | 30 | 8 | 99.2 | 49 |
| 114 | 10 | water:methyl acetate | 8:2 | 200 | 45 | 7 | 99.1 | 52 |
| 115 | 10 | water:methyl acetate | 3:7 | 200 | 50 | 7 | 99.0 | 55 |
| 116 | 10 | water:methyl acetate | 7:3 | 200 | 60 | 5 | 99.0 | 54 |
| 117 | 10 | water:methyl acetate | 4:6 | 200 | 70 | 4 | 99.2 | 51 |
| 118 | 10 | water:methyl acetate | 6:4 | 200 | 80 | 3 | 99.1 | 53 |
| 119 | 10 | water:methyl acetate | 5:5 | 200 | 55 | 6 | 98.9 | 48 |
| 120 | 10 | water:propyl acetate | 2:8 | 200 | 30 | 8 | 98.8 | 49 |
| 121 | 10 | water:propyl acetate | 8:2 | 200 | 45 | 7 | 98.8 | 47 |
| 122 | 10 | water:propyl acetate | 3:7 | 200 | 50 | 7 | 98.9 | 50 |
| 123 | 10 | water:propyl acetate | 7:3 | 200 | 60 | 5 | 98.9 | 51 |

TABLE 2-continued

Preparation of the 2/7 hydrate (Examples 106~161)

| Ex. | Amount of the crude material (g) | Solvent Mixture of organic solvent and water | Volume ratio | Amount (ml) | Stirring conditions T (° C.) | Time (hr) | Purity % | Yield % |
|---|---|---|---|---|---|---|---|---|
| 124 | 10 | water:propyl acetate | 4:6 | 200 | 70 | 4 | 99.3 | 52 |
| 125 | 10 | water:propyl acetate | 6:4 | 200 | 80 | 3 | 99.2 | 54 |
| 126 | 10 | water:propyl acetate | 5:5 | 200 | 55 | 6 | 99.0 | 49 |
| 127 | 10 | water:iso-butyl acetate | 2:8 | 200 | 30 | 8 | 99.0 | 49 |
| 128 | 10 | water:iso-butyl acetate | 8:2 | 200 | 45 | 7 | 99.1 | 49 |
| 129 | 10 | water:iso-butyl acetate | 3:7 | 200 | 50 | 7 | 98.9 | 48 |
| 130 | 10 | water:iso-butyl acetate | 7:3 | 200 | 60 | 5 | 99.0 | 50 |
| 131 | 10 | water:iso-butyl acetate | 4:6 | 200 | 70 | 4 | 98.7 | 55 |
| 132 | 10 | water:iso-butyl acetate | 6:4 | 200 | 80 | 3 | 98.7 | 58 |
| 133 | 10 | water:iso-butyl acetate | 5:5 | 200 | 55 | 6 | 98.6 | 44 |
| 134 | 10 | water:heptyl acetate | 2:8 | 200 | 30 | 8 | 98.8 | 48 |
| 135 | 10 | water:heptyl acetate | 8:2 | 200 | 45 | 7 | 98.9 | 49 |
| 136 | 10 | water:heptyl acetate | 3:7 | 200 | 50 | 7 | 99.2 | 48 |
| 137 | 10 | water:heptyl acetate | 7:3 | 200 | 60 | 5 | 99.3 | 45 |
| 138 | 10 | water:heptyl acetate | 4:6 | 200 | 70 | 4 | 98.5 | 50 |
| 139 | 10 | water:heptyl acetate | 6:4 | 200 | 80 | 3 | 98.38 | 50 |
| 140 | 10 | water:heptyl acetate | 5:5 | 200 | 55 | 6 | 98.9 | 51 |
| 141 | 10 | water:decyl acetate | 2:8 | 200 | 30 | 8 | 99.0 | 55 |
| 142 | 10 | water:decyl acetate | 8:2 | 200 | 45 | 7 | 99.0 | 44 |
| 143 | 10 | water:decyl acetate | 3:7 | 200 | 50 | 7 | 99.0 | 45 |
| 144 | 10 | water:decyl acetate | 7:3 | 200 | 60 | 5 | 99.1 | 47 |
| 145 | 10 | water:decyl acetate | 4:6 | 200 | 70 | 4 | 99.4 | 47 |
| 146 | 10 | water:decyl acetate | 6:4 | 200 | 80 | 3 | 99.1 | 50 |
| 147 | 10 | water:decyl acetate | 5:5 | 200 | 55 | 6 | 98.9 | 50 |
| 148 | 10 | water:glycol diacetate | 2:8 | 200 | 30 | 8 | 98.9 | 53 |
| 149 | 10 | water:glycol diacetate | 8:2 | 200 | 45 | 7 | 98.8 | 56 |
| 150 | 10 | water:glycol diacetate | 3:7 | 200 | 50 | 7 | 99.2 | 48 |
| 151 | 10 | water:glycol diacetate | 7:3 | 200 | 60 | 5 | 99.1 | 49 |
| 152 | 10 | water:glycol diacetate | 4:6 | 200 | 70 | 4 | 99.1 | 49 |
| 153 | 10 | water:glycol diacetate | 6:4 | 200 | 80 | 3 | 99.1 | 49 |
| 154 | 10 | water:glycol diacetate | 5:5 | 200 | 55 | 6 | 98.8 | 52 |
| 155 | 10 | water:phenyl acetate | 2:8 | 200 | 30 | 8 | 98.9 | 52 |
| 156 | 10 | water:phenyl acetate | 8:2 | 200 | 45 | 7 | 98.7 | 51 |
| 157 | 10 | water:phenyl acetate | 3:7 | 200 | 50 | 7 | 98.9 | 49 |
| 158 | 10 | water:phenyl acetate | 7:3 | 200 | 60 | 5 | 98.8 | 47 |
| 159 | 10 | water:phenyl acetate | 4:6 | 200 | 70 | 4 | 99.1 | 56 |
| 160 | 10 | water:phenyl acetate | 6:4 | 200 | 80 | 3 | 99.1 | 53 |
| 161 | 10 | water:phenyl acetate | 5:5 | 200 | 55 | 6 | 99.0 | 58 |

EXAMPLES 162-252

Preparation of (S)—[N-3-(3'-fluoro-4'-(4"-phenyl piperazinyl))phenyl-2-oxo-5-oxazolidinyl]methyl acetamide 2/5 hydrate ($C_{22}H_{25}N_4O_3 \cdot 2/5H_2O$)

Figure 17:
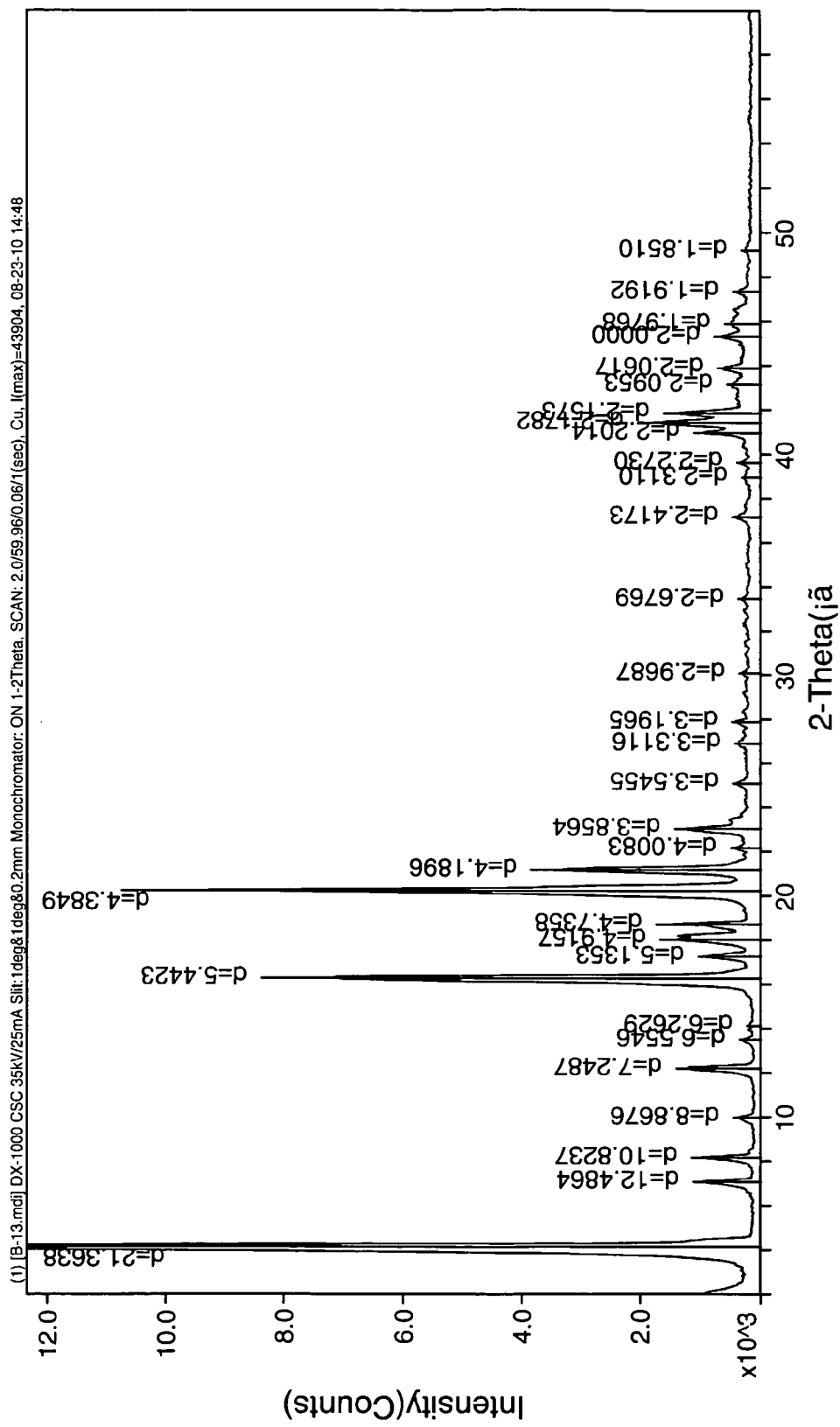
FIG. 17 is the X-ray diffractogram of (S)—[N-3-(3'-fluoro-4'-(4"-phenyl piperazinyl))phenyl-2-oxo-5-oxazolidinyl]methyl acetamide 2/5 hydrate prepared in Example 162.
Figure 18:
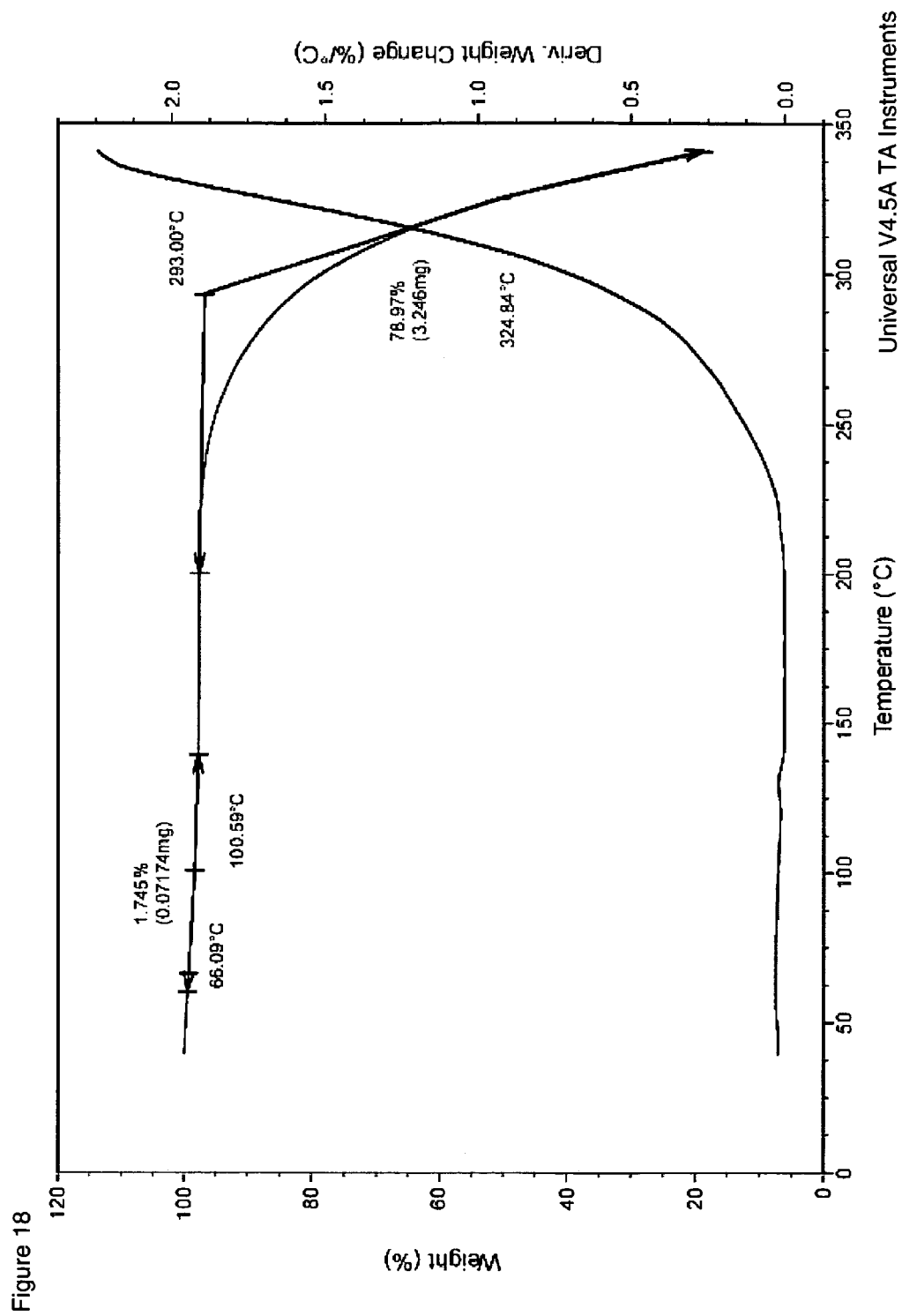
FIG. 18 is the TGA diagram of (S)—[N-3-(3'-fluoro-4'-(4"-phenyl piperazinyl))phenyl-2-oxo-5-oxazolidinyl]methyl acetamide 2/5 hydrate prepared in Example 162.

As shown in Table 3, a solultion of (S)—[N-3-(3'-fluoro-4'-(4"-phenyl piperazinyl))phenyl-2-oxo-5-oxazolidinyl]methyl acetamide was prepared by mixing 10 g of (S)—[N-3-(3'-fluoro-4'-(4"-phenyl piperazinyl))phenyl-2-oxo-5-oxazolidinyl]methyl acetamide crude prepared according to Example 1 with 200 ml of a mixed solvent containing an acidic solvent and an organic solvent. The solution was then stirred, filtered, and crystallized according to the conditions listed in Table 3. The crystalline compound obtained in Example 162 had a melting temperature of 210-215° C. measured by a capillary tube, and its XRPD and TGA analysis are shown in FIGS. 17 and 18. TGA data shows that the water content of the crystalline compound in Example 162 was 1.70±0.15%, indicating that the crystalline compound was a 2/5 hydrate of (S)—[N-3-(3'-fluoro-4'-(4"-phenyl piperazinyl))phenyl-2-oxo-5-oxazolidinyl]methyl acetamide. The TGA and the melting temperature of the crystalline compounds prepared in Examples 163-252 were sufficiently similar to the TGA and the melting point of the 2/5 hydrate prepared in Example 162 to be consistent with the conclusion that all were the 2/5 hydrate prepared in Example 162.

TABLE 3

| | | | Solvent | | | Stirring conditions | | | |
|---|---|---|---|---|---|---|---|---|---|
| Ex | Amount of the crude material (g) | pH[a] | Mixture of acidic solvent and organic solvent | Volumetric ratio | Amount (ml) | T(° C.) | time (hr) | Purity % | Yield % |
| 162 | 10 | 2 | hypophosphorous acid aqueous solution:propanol | 2:8 | 200 | 30 | 8 | 99.0 | 51 |
| 163 | 10 | 2 | hypophosphorous acid aqueous solution:propanol | 8:2 | 200 | 45 | 7 | 99.1 | 56 |
| 164 | 10 | 2 | hypophosphorous acid aqueous solution:propanol | 3:7 | 200 | 50 | 7 | 98.9 | 55 |
| 165 | 10 | 2 | hypophosphorous acid aqueous solution:propanol | 7:3 | 200 | 60 | 5 | 98.7 | 45 |
| 166 | 10 | 2 | hypophosphorous acid aqueous solution:propanol | 4:6 | 200 | 70 | 4 | 99.1 | 46 |
| 167 | 10 | 2 | hypophosphorous acid aqueous solution:propanol | 6:4 | 200 | 80 | 3 | 99.0 | 51 |
| 168 | 10 | 2 | hypophosphorous acid aqueous solution:propanol | 5:5 | 200 | 55 | 6 | 98.9 | 50 |
| 169 | 10 | 3 | hypophosphorous acid aqueous solution:propanol | 2:8 | 200 | 30 | 8 | 98.8 | 58 |
| 170 | 10 | 3 | hypophosphorous acid aqueous solution:propanol | 8:2 | 200 | 45 | 7 | 98.8 | 47 |
| 171 | 10 | 3 | hypophosphorous acid aqueous solution:propanol | 3:7 | 200 | 50 | 7 | 98.9 | 49 |
| 172 | 10 | 3 | hypophosphorous acid aqueous solution:propanol | 7:3 | 200 | 60 | 5 | 99.2 | 48 |
| 173 | 10 | 3 | hypophosphorous acid aqueous solution:propanol | 4:6 | 200 | 70 | 4 | 99.3 | 46 |
| 174 | 10 | 3 | hypophosphorous acid aqueous solution:propanol | 6:4 | 200 | 80 | 3 | 99.2 | 54 |
| 175 | 10 | 3 | hypophosphorous acid aqueous solution:propanol | 5:5 | 200 | 55 | 6 | 99.0 | 54 |
| 176 | 10 | 4 | hypophosphorous acid aqueous solution:propanol | 2:8 | 200 | 30 | 8 | 99.1 | 51 |
| 177 | 10 | 4 | hypophosphorous acid aqueous solution:propanol | 8:2 | 200 | 45 | 7 | 98.9 | 56 |
| 178 | 10 | 4 | hypophosphorous acid aqueous solution:propanol | 3:7 | 200 | 50 | 7 | 98.7 | 55 |
| 179 | 10 | 4 | hypophosphorous acid aqueous solution:propanol | 7:3 | 200 | 60 | 5 | 98.8 | 52 |
| 180 | 10 | 4 | hypophosphorous acid aqueous solution:propanol | 4:6 | 200 | 70 | 4 | 98.8 | 58 |
| 181 | 10 | 4 | hypophosphorous acid aqueous solution:propanol | 6:4 | 200 | 80 | 3 | 98.9 | 48 |
| 182 | 10 | 4 | hypophosphorous acid aqueous solution:propanol | 5:5 | 200 | 55 | 6 | 98.9 | 47 |
| 183 | 10 | 5 | hypophosphorous acid aqueous solution:propanol | 2:8 | 200 | 30 | 8 | 99.0 | 47 |

TABLE 3-continued

Preparation of the 2/5 hydrate (Examples 162~252)

| Ex | Amount of the crude material (g) | pH[a] | Mixture of acidic solvent and organic solvent | Volumetric ratio | Amount (ml) | T(°C.) | time (hr) | Purity % | Yield % |
|---|---|---|---|---|---|---|---|---|---|
| 184 | 10 | 5 | hypophosphorous acid aqueous solution:propanol | 8:2 | 200 | 45 | 7 | 99.0 | 48 |
| 185 | 10 | 5 | hypophosphorous acid aqueous solution:propanol | 3:7 | 200 | 50 | 7 | 99.2 | 49 |
| 186 | 10 | 5 | hypophosphorous acid aqueous solution:propanol | 7:3 | 200 | 60 | 5 | 99.2 | 46 |
| 187 | 10 | 5 | hypophosphorous acid aqueous solution:propanol | 4:6 | 200 | 70 | 4 | 99.2 | 55 |
| 188 | 10 | 5 | hypophosphorous acid aqueous solution:propanol | 6:4 | 200 | 80 | 3 | 99.1 | 44 |
| 189 | 10 | 5 | hypophosphorous acid aqueous solution:propanol | 5:5 | 200 | 55 | 6 | 98.9 | 51 |
| 190 | 10 | 2 | metaphosphoric acid aqueous solution:glycol | 2:8 | 200 | 30 | 8 | 98.9 | 50 |
| 191 | 10 | 2 | metaphosphoric acid aqueous solution:glycol | 8:2 | 200 | 45 | 7 | 98.8 | 50 |
| 192 | 10 | 2 | metaphosphoric acid aqueous solution:glycol | 3:7 | 200 | 50 | 7 | 99.0 | 50 |
| 193 | 10 | 2 | metaphosphoric acid aqueous solution:glycol | 7:3 | 200 | 60 | 5 | 99.0 | 48 |
| 194 | 10 | 2 | metaphosphoric acid aqueous solution:glycol | 4:6 | 200 | 70 | 4 | 98.9 | 49 |
| 195 | 10 | 2 | metaphosphoric acid aqueous solution:glycol | 6:4 | 200 | 80 | 3 | 98.9 | 52 |
| 196 | 10 | 2 | metaphosphoric acid aqueous solution:glycol | 5:5 | 200 | 55 | 6 | 99.2 | 52 |
| 197 | 10 | 3 | metaphosphoric acid aqueous solution:glycol | 2:8 | 200 | 30 | 8 | 99.2 | 51 |
| 198 | 10 | 3 | metaphosphoric acid aqueous solution:glycol | 8:2 | 200 | 45 | 7 | 99.1 | 52 |
| 199 | 10 | 3 | metaphosphoric acid aqueous solution:glycol | 3:7 | 200 | 50 | 7 | 98.9 | 52 |
| 200 | 10 | 3 | metaphosphoric acid aqueous solution:glycol | 7:3 | 200 | 60 | 5 | 98.9 | 50 |
| 201 | 10 | 3 | metaphosphoric acid aqueous solution:glycol | 4:6 | 200 | 70 | 4 | 98.9 | 50 |
| 202 | 10 | 3 | metaphosphoric acid aqueous solution:glycol | 6:4 | 200 | 80 | 3 | 99.0 | 49 |
| 203 | 10 | 3 | metaphosphoric acid aqueous solution:glycol | 5:5 | 200 | 55 | 6 | 99.0 | 48 |
| 204 | 10 | 4 | metaphosphoric acid aqueous solution:glycol | 2:8 | 200 | 30 | 8 | 99.2 | 49 |
| 205 | 10 | 4 | metaphosphoric acid aqueous solution:glycol | 8:2 | 200 | 45 | 7 | 99.1 | 48 |

TABLE 3-continued

Preparation of the 2/5 hydrate (Examples 162~252)

| Ex | Amount of the crude material (g) | pH[a] | Solvent Mixture of acidic solvent and organic solvent | Volumetric ratio | Amount (ml) | Stirring conditions T(°C.) | time (hr) | Purity % | Yield % |
|---|---|---|---|---|---|---|---|---|---|
| 206 | 10 | 4 | metaphosphoric acid aqueous solution:glycol | 3:7 | 200 | 50 | 7 | 99.1 | 45 |
| 207 | 10 | 4 | metaphosphoric acid aqueous solution:glycol | 7:3 | 200 | 60 | 5 | 98.9 | 55 |
| 208 | 10 | 4 | metaphosphoric acid aqueous solution:glycol | 4:6 | 200 | 70 | 4 | 98.9 | 55 |
| 209 | 10 | 4 | metaphosphoric acid aqueous solution:glycol | 6:4 | 200 | 80 | 3 | 99.2 | 55 |
| 210 | 10 | 4 | metaphosphoric acid aqueous solution:glycol | 5:5 | 200 | 55 | 6 | 99.3 | 51 |
| 211 | 10 | 5 | metaphosphoric acid aqueous solution:glycol | 2:8 | 200 | 30 | 8 | 99.0 | 45 |
| 212 | 10 | 5 | metaphosphoric acid aqueous solution:glycol | 8:2 | 200 | 45 | 7 | 99.0 | 46 |
| 213 | 10 | 5 | metaphosphoric acid aqueous solution:glycol | 3:7 | 200 | 50 | 7 | 98.9 | 46 |
| 214 | 10 | 5 | metaphosphoric acid aqueous solution:glycol | 7:3 | 200 | 60 | 5 | 98.9 | 47 |
| 215 | 10 | 5 | metaphosphoric acid aqueous solution:glycol | 4:6 | 200 | 70 | 4 | 98.7 | 41 |
| 216 | 10 | 5 | metaphosphoric acid aqueous solution:glycol | 6:4 | 200 | 80 | 3 | 98.8 | 48 |
| 217 | 10 | 5 | metaphosphoric acid aqueous solution:glycol | 5:5 | 200 | 55 | 6 | 98.9 | 47 |
| 218 | 10 | 4 | aluminic acid aqueous solution:butanol | 2:8 | 200 | 30 | 8 | 98.9 | 47 |
| 219 | 10 | 4 | aluminic acid aqueous solution:butanol | 8:2 | 200 | 45 | 7 | 99.2 | 48 |
| 220 | 10 | 4 | aluminic acid aqueous solution:butanol | 3:7 | 200 | 50 | 7 | 99.0 | 59 |
| 221 | 10 | 4 | aluminic acid aqueous solution:butanol | 7:3 | 200 | 60 | 5 | 98.9 | 50 |
| 222 | 10 | 4 | aluminic acid aqueous solution:butanol | 4:6 | 200 | 70 | 4 | 98.7 | 51 |
| 223 | 10 | 4 | aluminic acid aqueous solution:butanol | 6:4 | 200 | 80 | 3 | 98.7 | 42 |
| 224 | 10 | 4 | aluminic acid aqueous solution:butanol | 5:5 | 200 | 55 | 6 | 98.8 | 40 |
| 225 | 10 | 5 | aluminic acid aqueous solution:butanol | 2:8 | 200 | 30 | 8 | 99.0 | 47 |
| 226 | 10 | 5 | aluminic acid aqueous solution:butanol | 8:2 | 200 | 45 | 7 | 99.0 | 46 |
| 227 | 10 | 5 | aluminic acid aqueous solution:butanol | 3:7 | 200 | 50 | 7 | 99.1 | 58 |
| 228 | 10 | 5 | aluminic acid aqueous solution:butanol | 7:3 | 200 | 60 | 5 | 99.1 | 55 |
| 229 | 10 | 5 | aluminic acid aqueous solution:butanol | 4:6 | 200 | 70 | 4 | 98.9 | 54 |
| 230 | 10 | 5 | aluminic acid aqueous solution:butanol | 6:4 | 200 | 80 | 3 | 98.9 | 54 |
| 231 | 10 | 5 | aluminic acid aqueous solution:butanol | 5:5 | 200 | 55 | 6 | 99.3 | 51 |
| 232 | 10 | 5 | aluminic acid aqueous solution:N,N-dimethylformamide | 2:8 | 200 | 30 | 8 | 99.1 | 53 |

TABLE 3-continued

| | | | Preparation of the 2/5 hydrate (Examples 162~252) | | | | | | |
|---|---|---|---|---|---|---|---|---|---|
| | Amount of the crude | | Solvent | | | Stirring conditions | | | |
| Ex | material (g) | pH[a] | Mixture of acidic solvent and organic solvent | Volumetric ratio | Amount (ml) | T(°C.) | time (hr) | Purity % | Yield % |
| 233 | 10 | 5 | aluminic acid aqueous solution:N,N-dimethylformamide | 8:2 | 200 | 45 | 7 | 99.0 | 53 |
| 234 | 10 | 5 | aluminic acid aqueous solution:N,N-dimethylformamide | 3:7 | 200 | 50 | 7 | 99.0 | 58 |
| 235 | 10 | 5 | aluminic acid aqueous solution:N,N-dimethylformamide | 7:3 | 200 | 60 | 5 | 99.0 | 52 |
| 236 | 10 | 5 | aluminic acid aqueous solution:N,N-dimethylformamide | 4:6 | 200 | 70 | 4 | 99.0 | 50 |
| 237 | 10 | 5 | aluminic acid aqueous solution:N,N-dimethylformamide | 6:4 | 200 | 80 | 3 | 98.9 | 48 |
| 238 | 10 | 5 | aluminic acid aqueous solution:N,N-dimethylformamide | 5:5 | 200 | 55 | 6 | 98.7 | 48 |
| 239 | 10 | 5 | lactic acid aqueous solution:N,N-dimethylformamide | 2:8 | 200 | 30 | 8 | 98.8 | 49 |
| 240 | 10 | 5 | lactic acid aqueous solution:N,N-dimethylformamide | 8:2 | 200 | 45 | 7 | 98.8 | 57 |
| 241 | 10 | 5 | lactic acid aqueous solution:N,N-dimethylformamide | 3:7 | 200 | 50 | 7 | 98.7 | 50 |
| 242 | 10 | 5 | lactic acid aqueous solution:N,N-dimethylformamide | 7:3 | 200 | 60 | 5 | 99.0 | 51 |
| 243 | 10 | 5 | lactic acid aqueous solution:N,N-dimethylformamide | 4:6 | 200 | 70 | 4 | 99.1 | 51 |
| 244 | 10 | 5 | lactic acid aqueous solution:N,N-dimethylformamide | 6:4 | 200 | 80 | 3 | 99.2 | 50 |
| 245 | 10 | 5 | lactic acid aqueous solution:N,N-dimethylformamide | 5:5 | 200 | 55 | 6 | 99.1 | 50 |
| 246 | 10 | 5 | succinic acid aqueous solution:N,N-dimethylformamide | 2:8 | 200 | 30 | 8 | 99.0 | 55 |
| 247 | 10 | 5 | succinic acid aqueous solution:N,N-dimethylformamide | 8:2 | 200 | 45 | 7 | 98.8 | 46 |
| 248 | 10 | 5 | succinic acid aqueous solution:N,N-dimethylformamide | 3:7 | 200 | 50 | 7 | 98.8 | 48 |
| 249 | 10 | 5 | succinic acid aqueous solution:N,N-dimethylformamide | 7:3 | 200 | 60 | 5 | 98.9 | 59 |
| 250 | 10 | 5 | succinic acid aqueous solution:N,N-dimethylformamide | 4:6 | 200 | 70 | 4 | 98.8 | 50 |

TABLE 3-continued

Preparation of the 2/5 hydrate (Examples 162~252)

| Ex | Amount of the crude material (g) | pH[a] | Solvent Mixture of acidic solvent and organic solvent | Volumetric ratio | Amount (ml) | Stirring conditions T(° C.) | time (hr) | Purity % | Yield % |
|---|---|---|---|---|---|---|---|---|---|
| 251 | 10 | 5 | succinic acid aqueous solution:N,N-dimethylformamide | 6:4 | 200 | 80 | 3 | 98.8 | 57 |
| 252 | 10 | 5 | succinic acid aqueous solution:N,N-dimethylformamide | 5:5 | 200 | 55 | 6 | 98.1 | 40 |

[a] The pH value is the pH value of the acidic solution used.

EXAMPLES 253-336

Preparation of (S)—[N-3-(3'-fluoro-4'-(4"-phenyl piperazinyl))phenyl-2-oxo-5-oxazolidinyl]methyl acetamide 1/12 hydrate ($C_{22}H_{25}N_4O_3 \cdot 1/12H_2O$)

As shown in Table 4, a solultion of (S)—[N-3-(3'-fluoro-4'-(4"-phenyl piperazinyl))phenyl-2-oxo-5-oxazolidinyl]methyl acetamide was prepared by mixing 10 g of (S)—[N-3-(3'-fluoro-4'-(4"-phenyl piperazinyl))phenyl-2-oxo-5-oxazolidinyl]methyl acetamide crude prepared according to Example 1 with 200 ml of a mixed solvent containing water and an organic solvent. The solution was then stirred, filtered, and crystallized according to the conditions listed in Table 4.

Figure 19:
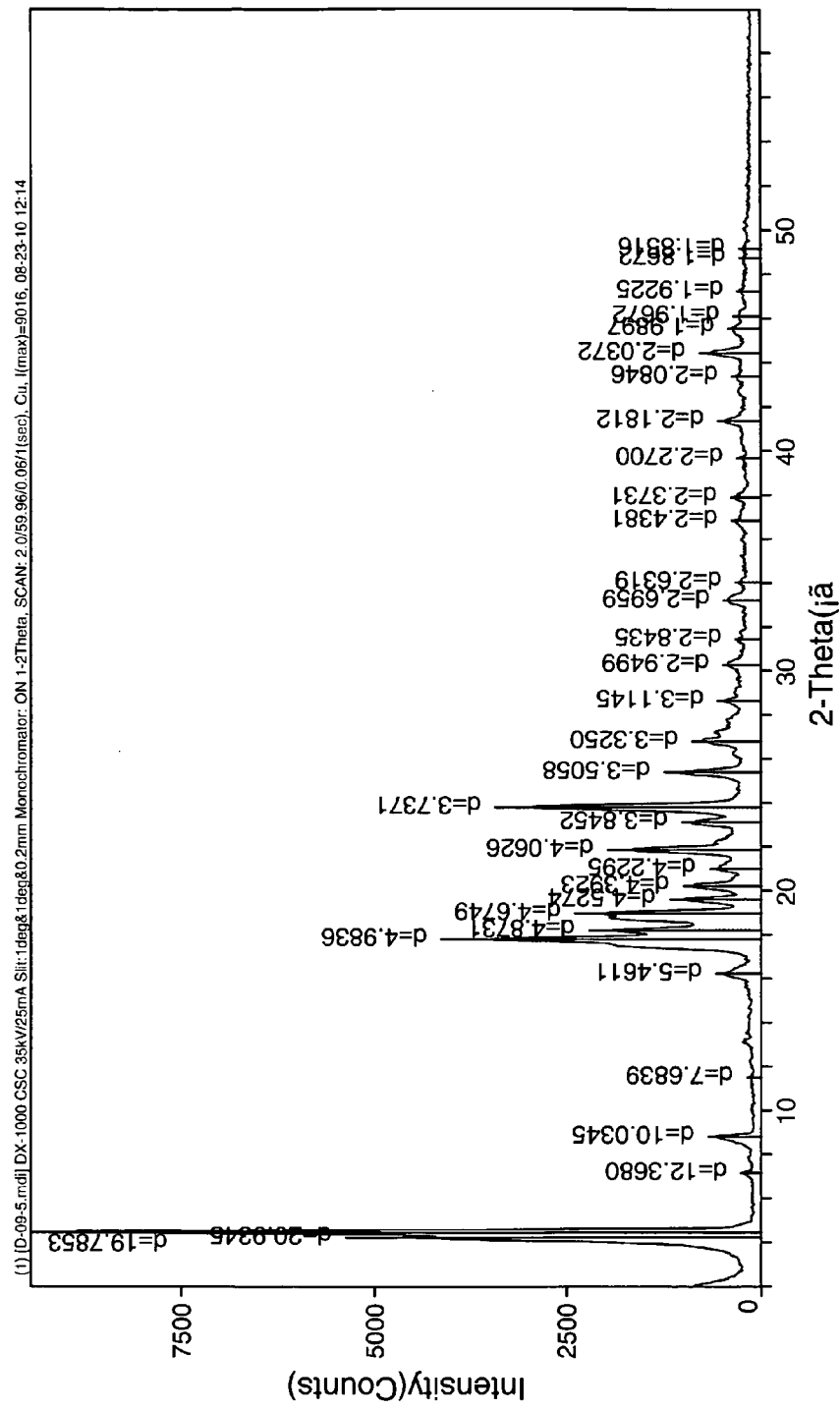
FIG. 19 is the X-ray diffractogram of the (S)—[N-3-(3'-fluoro-4'-(4"-phenyl piperazinyl))phenyl-2-oxo-5-oxazolidinyl]methyl acetamide 1/12 hydrate prepared in Example 253.
Figure 20:
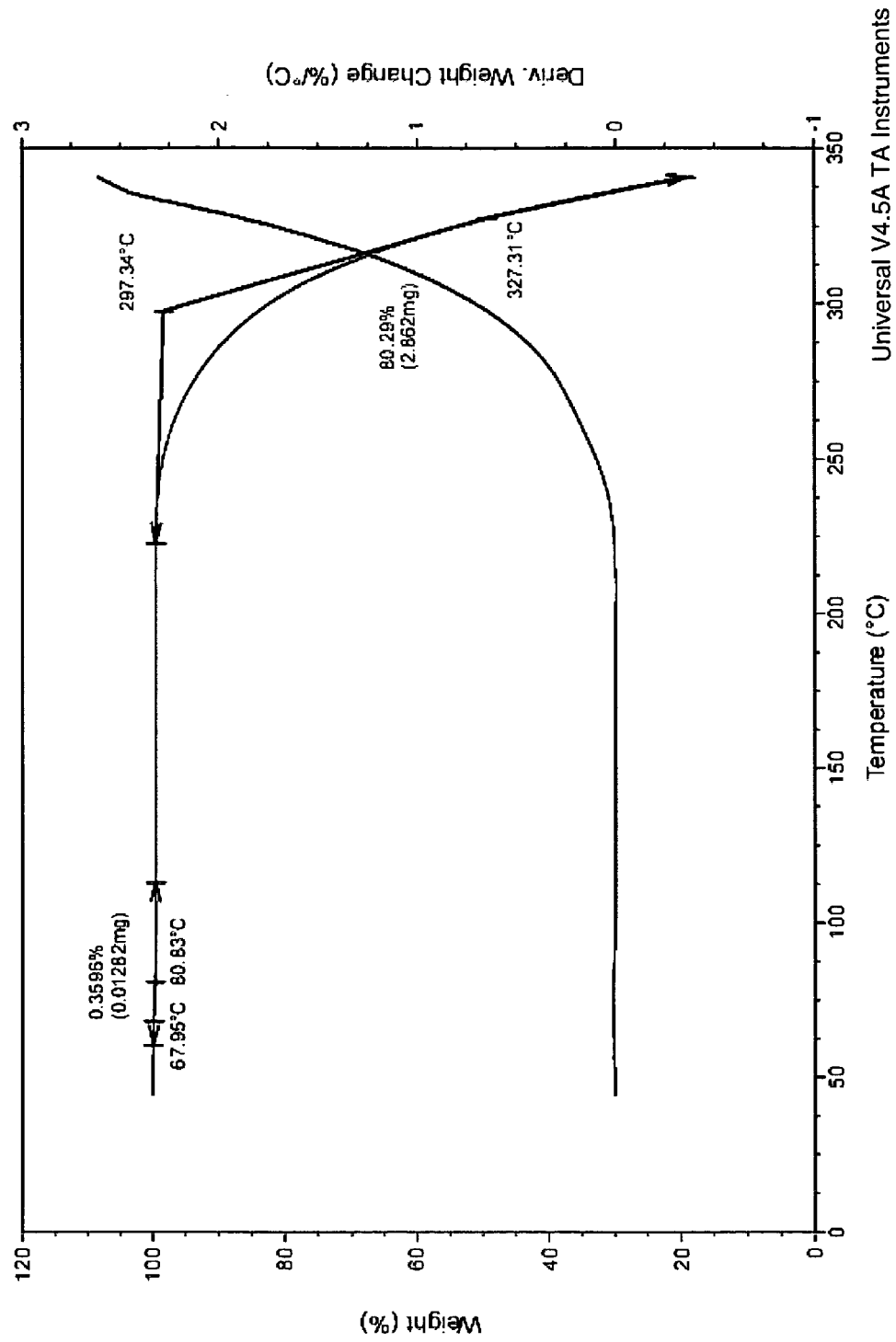
FIG. 20 is the TGA diagram of (S)—[N-3-(3'-fluoro-4'-(4"-phenyl piperazinyl))phenyl-2-oxo-5-oxazolidinyl]methyl acetamide 1/12 hydrate prepared in Example 253.

The crystalline compound obtained in Example 253 had a melting temperature of 210-214° C. measured by a capillary tube, and its XRPD and TGA analysis are shown in FIGS. 19 and 20. TGA data show that the water content of the crystalline compound in Example 253 was 0.40±0.15%, indicating that the crystalline compound was a 1/12 hydrate of (S)—[N-3-(3'-fluoro-4'-(4"-phenyl piperazinyl))phenyl-2-oxo-5-oxazolidinyl]methyl acetamide. The TGA and the melting temperature of the crystalline compounds prepared in Examples 254-336 were sufficiently similar to the TGA and the melting point of the 1/12 hydrate prepared in Example 253 to be consistent with the conclusion that all were the 1/12 hydrate prepared in Example 253.

TABLE 4

Preparation of the 1/12 hydrate (Examples 253~336)

| Ex. | Amount of the crude material (g) | Kind of solvent | Volumetric ratio | Amount (ml) | Stirring conditions T (° C.) | Time (hr) | Purity % | Yield % |
|---|---|---|---|---|---|---|---|---|
| 253 | 10 | water:ethanol | 2:8 | 200 | 30 | 8 | 98.9 | 52 |
| 254 | 10 | water:ethanol | 8:2 | 200 | 45 | 7 | 98.8 | 51 |
| 255 | 10 | water:ethanol | 3:7 | 200 | 50 | 7 | 98.8 | 55 |
| 256 | 10 | water:ethanol | 7:3 | 200 | 60 | 5 | 98.7 | 53 |
| 257 | 10 | water:ethanol | 4:6 | 200 | 70 | 4 | 99.2 | 46 |
| 258 | 10 | water:ethanol | 6:4 | 200 | 80 | 3 | 99.1 | 42 |
| 259 | 10 | water:ethanol | 5:5 | 200 | 55 | 6 | 99.0 | 48 |
| 260 | 10 | water:methanol | 2:8 | 200 | 30 | 8 | 99.1 | 54 |
| 261 | 10 | water:methanol | 8:2 | 200 | 45 | 7 | 99.0 | 51 |
| 262 | 10 | water:methanol | 3:7 | 200 | 50 | 7 | 98.9 | 57 |
| 263 | 10 | water:methanol | 7:3 | 200 | 60 | 5 | 98.9 | 42 |
| 264 | 10 | water:methanol | 4:6 | 200 | 70 | 4 | 98.8 | 54 |
| 265 | 10 | water:methanol | 6:4 | 200 | 80 | 3 | 98.8 | 54 |
| 266 | 10 | water:methanol | 5:5 | 200 | 55 | 6 | 98.8 | 55 |
| 267 | 10 | water:acetonitrile | 2:8 | 200 | 30 | 8 | 99.0 | 58 |
| 268 | 10 | water:acetonitrile | 8:2 | 200 | 45 | 7 | 99.0 | 43 |
| 269 | 10 | water:acetonitrile | 3:7 | 200 | 50 | 7 | 99.1 | 43 |
| 270 | 10 | water:acetonitrile | 7:3 | 200 | 60 | 5 | 99.2 | 44 |
| 271 | 10 | water:acetonitrile | 4:6 | 200 | 70 | 4 | 99.0 | 55 |
| 272 | 10 | water:acetonitrile | 6:4 | 200 | 80 | 3 | 99.0 | 44 |
| 273 | 10 | water:acetonitrile | 5:5 | 200 | 55 | 6 | 99.0 | 52 |
| 274 | 10 | water:1,2-propylene glycol | 2:8 | 200 | 30 | 8 | 99.0 | 50 |
| 275 | 10 | water:1,2-propylene glycol | 8:2 | 200 | 45 | 7 | 99.1 | 50 |
| 276 | 10 | water:1,2-propylene glycol | 3:7 | 200 | 50 | 7 | 98.9 | 51 |
| 277 | 10 | water:1,2-propylene glycol | 7:3 | 200 | 60 | 5 | 98.9 | 57 |

TABLE 4-continued

Preparation of the 1/12 hydrate (Examples 253~336)

| Ex. | Amount of the crude material (g) | Solvent Kind of solvent | Volumetric ratio | Amount (ml) | Stirring conditions T (°C.) | Time (hr) | Purity % | Yield % |
|---|---|---|---|---|---|---|---|---|
| 278 | 10 | water:1,2-propylene glycol | 4:6 | 200 | 70 | 4 | 98.8 | 48 |
| 279 | 10 | water:1,2-propylene glycol | 6:4 | 200 | 80 | 3 | 99.0 | 49 |
| 280 | 10 | water:1,2-propylene glycol | 5:5 | 200 | 55 | 6 | 98.9 | 48 |
| 281 | 10 | water:1,2-propylene glycol:methanol | 2:4:4 | 200 | 30 | 8 | 98.8 | 49 |
| 282 | 10 | water:1,2-propylene glycol:methanol | 8:1:1 | 200 | 45 | 7 | 98.8 | 48 |
| 283 | 10 | water:1,2-propylene glycol:methanol | 3:3:4 | 200 | 50 | 7 | 98.8 | 48 |
| 284 | 10 | water:1,2-propylene glycol:methanol | 7:2:1 | 200 | 60 | 5 | 99.3 | 49 |
| 285 | 10 | water:1,2-propylene glycol:methanol | 4:4:2 | 200 | 70 | 4 | 99.0 | 45 |
| 286 | 10 | water:1,2-propylene glycol:methanol | 6:2:2 | 200 | 80 | 3 | 99.0 | 46 |
| 287 | 10 | water:1,2-propylene glycol:methanol | 5:3:2 | 200 | 55 | 6 | 99.1 | 45 |
| 288 | 10 | water:1,2-propylene glycol:ethanol | 2:4:4 | 200 | 30 | 8 | 98.7 | 45 |
| 289 | 10 | water:1,2-propylene glycol:ethanol | 8:1:1 | 200 | 45 | 7 | 98.8 | 55 |
| 290 | 10 | water:1,2-propylene glycol:ethanol | 3:3:4 | 200 | 50 | 7 | 98.8 | 52 |
| 291 | 10 | water:1,2-propylene glycol:ethanol | 7:2:1 | 200 | 60 | 5 | 98.8 | 51 |
| 292 | 10 | water:1,2-propylene glycol:ethanol | 4:4:2 | 200 | 70 | 4 | 99.0 | 51 |
| 293 | 10 | water:1,2-propylene glycol:ethanol | 6:2:2 | 200 | 80 | 3 | 99.0 | 51 |
| 294 | 10 | water:1,2-propylene glycol:ethanol | 5:3:2 | 200 | 55 | 6 | 99.2 | 50 |
| 295 | 10 | water:1,2-propylene glycol:acetonitrile | 2:4:4 | 200 | 30 | 8 | 99.1 | 50 |
| 296 | 10 | water:1,2-propylene glycol:acetonitrile | 8:1:1 | 200 | 45 | 7 | 99.1 | 50 |
| 297 | 10 | water:1,2-propylene glycol:acetonitrile | 3:3:4 | 200 | 50 | 7 | 98.7 | 53 |
| 298 | 10 | water:1,2-propylene glycol:acetonitrile | 7:2:1 | 200 | 60 | 5 | 98.6 | 58 |
| 299 | 10 | water:1,2-propylene glycol:acetonitrile | 4:4:2 | 200 | 70 | 4 | 98.6 | 57 |
| 300 | 10 | water:1,2-propylene glycol:acetonitrile | 6:2:2 | 200 | 80 | 3 | 98.7 | 57 |
| 301 | 10 | water:1,2-propylene glycol:acetonitrile | 5:3:2 | 200 | 55 | 6 | 99.1 | 54 |
| 302 | 10 | water:isopropanol | 2:8 | 200 | 30 | 8 | 99.0 | 44 |
| 303 | 10 | water:isopropanol | 8:2 | 200 | 45 | 7 | 99.2 | 44 |
| 304 | 10 | water:isopropanol | 3:7 | 200 | 50 | 7 | 98.9 | 48 |
| 305 | 10 | water:isopropanol | 7:3 | 200 | 60 | 5 | 98.8 | 48 |
| 306 | 10 | water:isopropanol | 4:6 | 200 | 70 | 4 | 98.3 | 49 |
| 307 | 10 | water:isopropanol | 6:4 | 200 | 80 | 3 | 98.6 | 49 |
| 308 | 10 | water:isopropanol | 5:5 | 200 | 55 | 6 | 98.2 | 49 |
| 309 | 10 | water:n-propanol | 2:8 | 200 | 30 | 8 | 98.9 | 51 |
| 310 | 10 | water:n-propanol | 8:2 | 200 | 45 | 7 | 99.0 | 51 |
| 311 | 10 | water:n-propanol | 3:7 | 200 | 50 | 7 | 99.3 | 58 |
| 312 | 10 | water:n-propanol | 7:3 | 200 | 60 | 5 | 98.4 | 51 |
| 313 | 10 | water:n-propanol | 4:6 | 200 | 70 | 4 | 98.7 | 51 |
| 314 | 10 | water:n-propanol | 6:4 | 200 | 80 | 3 | 98.2 | 50 |
| 315 | 10 | water:n-propanol | 5:5 | 200 | 55 | 6 | 98.6 | 50 |
| 316 | 10 | water:2-butanol | 2:8 | 200 | 30 | 8 | 98.5 | 50 |
| 317 | 10 | water:2-butanol | 8:2 | 200 | 45 | 7 | 98.5 | 52 |
| 318 | 10 | water:2-butanol | 3:7 | 200 | 50 | 7 | 98.8 | 58 |
| 319 | 10 | water:2-butanol | 7:3 | 200 | 60 | 5 | 98.9 | 57 |
| 320 | 10 | water:2-butanol | 4:6 | 200 | 70 | 4 | 99.0 | 48 |
| 321 | 10 | water:2-butanol | 6:4 | 200 | 80 | 3 | 99.1 | 49 |
| 322 | 10 | water:2-butanol | 5:5 | 200 | 55 | 6 | 99.1 | 47 |
| 323 | 10 | water:isobutanol | 2:8 | 200 | 30 | 8 | 98.5 | 47 |
| 324 | 10 | water:isobutanol | 8:2 | 200 | 45 | 7 | 98.7 | 45 |

TABLE 4-continued

Preparation of the 1/12 hydrate (Examples 253~336)

| Ex. | Amount of the crude material (g) | Solvent Kind of solvent | Volumetric ratio | Amount (ml) | Stirring conditions T (° C.) | Time (hr) | Purity % | Yield % |
|---|---|---|---|---|---|---|---|---|
| 325 | 10 | water:isobutanol | 3:7 | 200 | 50 | 7 | 99.0 | 46 |
| 326 | 10 | water:isobutanol | 7:3 | 200 | 60 | 5 | 99.1 | 45 |
| 327 | 10 | water:isobutanol | 4:6 | 200 | 70 | 4 | 98.9 | 55 |
| 328 | 10 | water:isobutanol | 6:4 | 200 | 80 | 3 | 98.8 | 58 |
| 329 | 10 | water:isobutanol | 5:5 | 200 | 55 | 6 | 98.7 | 52 |
| 330 | 10 | water:glycol | 2:8 | 200 | 30 | 8 | 98.5 | 52 |
| 331 | 10 | water:glycol | 8:2 | 200 | 45 | 7 | 98.6 | 53 |
| 332 | 10 | water:glycol | 3:7 | 200 | 50 | 7 | 98.4 | 53 |
| 333 | 10 | water:glycol | 7:3 | 200 | 60 | 5 | 98.9 | 51 |
| 334 | 10 | water:glycol | 4:6 | 200 | 70 | 4 | 99.1 | 45 |
| 335 | 10 | water:glycol | 6:4 | 200 | 80 | 3 | 99.0 | 48 |
| 336 | 10 | water:glycol | 5:5 | 200 | 55 | 6 | 98.9 | 49 |

EXAMPLES 337-358

Preparation of (S)—[N-3-(3'-fluoro-4'-(4"-phenyl piperazinyl))phenyl-2-oxo-5-oxazolidinyl]methyl acetamide 3/4 hydrate ($C_{22}H_{25}N_4O_3 \cdot 3/4H_2O$)

Figure 21:
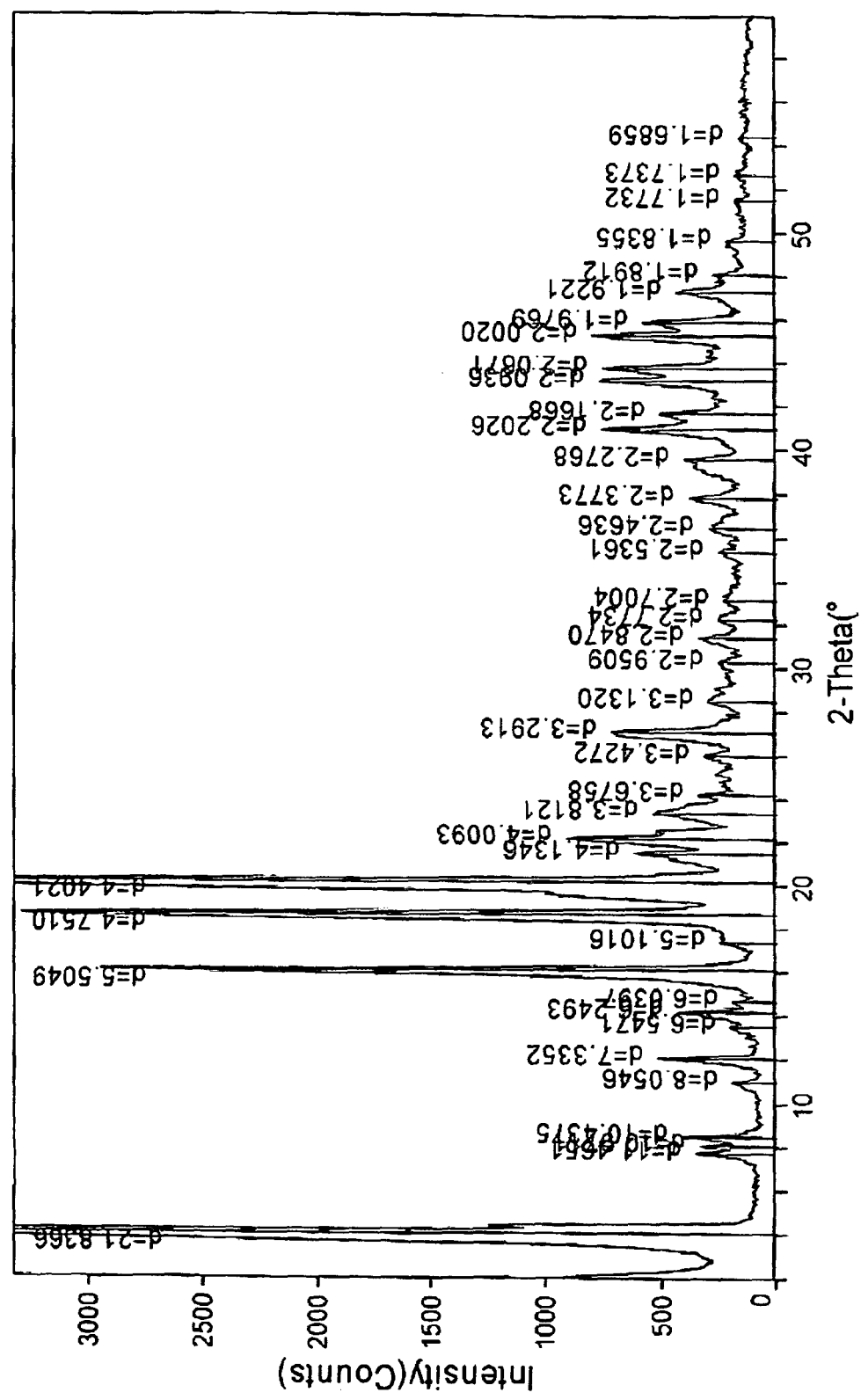
FIG. 21 is the X-ray diffractogram of the (S)—[N-3-(3'-fluoro-4'-(4"-phenyl piperazinyl))phenyl-2-oxo-5-oxazolidinyl]methyl acetamide 3/4 hydrate prepared in Example 337.
Figure 22:
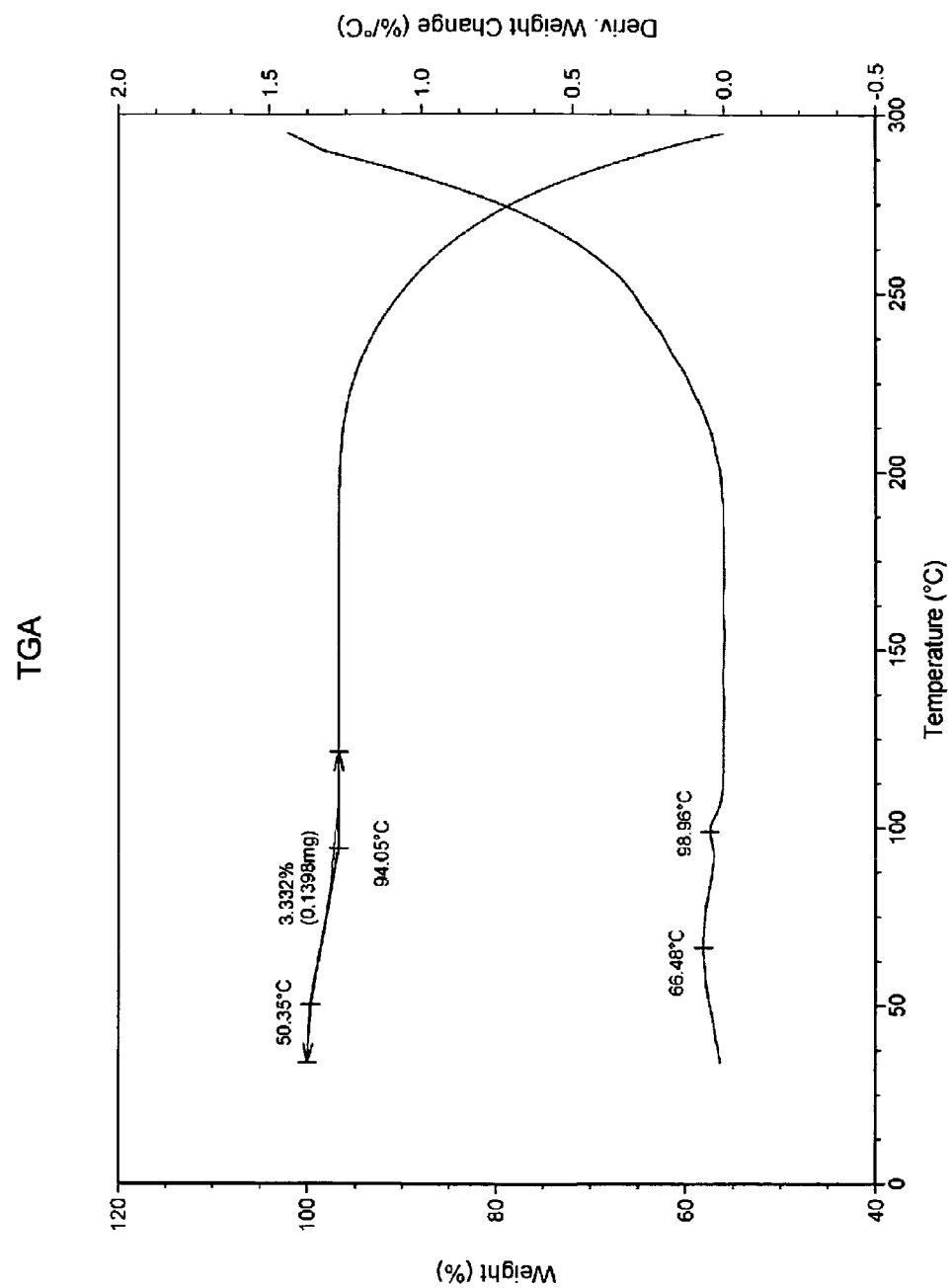
FIG. 22 is the TGA diagram of (S)—[N-3-(3'-fluoro-4'-(4"-phenyl piperazinyl))phenyl-2-oxo-5-oxazolidinyl]methyl acetamide 3/4 hydrate prepared in Example 337.

As shown in Table 5, a solultion of (S)—[N-3-(3'-fluoro-4'-(4"-phenyl piperazinyl))phenyl-2-oxo-5-oxazolidinyl]methyl acetamide was prepared by mixing 10 g of (S)—[N-3-(3'-fluoro-4'-(4"-phenyl piperazinyl))phenyl-2-oxo-5-oxazolidinyl]methyl acetamide crude prepared according to Example 1 with 200 ml of water or 200 ml of a mixed solvent containing water and dimethyl sulfoxide or Tween 80. The solution was then stirred, filtered, and crystallized according to the conditions listed in Table 5. The crystalline compound obtained in Example 337 had a melting temperature of 210-215° C. as measured by a capillary tube, and its XRPD and TGA analysis are shown in FIGS. 21 and 22. TGA data shows that the water content of the crystalline compound in Example 337 was 3.30±0.15%, indicating that the crystalline compound was a 3/4 hydrate of (S)—[N-3-(3'-fluoro-4'-(4"-phenyl piperazinyl))phenyl-2-oxo-5-oxazolidinyl]methyl acetamide. The TGA and the melting temperature of the crystalline compounds prepared in Examples 338-358 were sufficiently similar to the TGA and the melting point of the 3/4 hydrate prepared in Example 337 to be consistent with the conclusion that all were the 3/4 hydrate prepared in Example 337.

TABLE 5

Preparation of the 3/4 hydrates (Examples 337~358)

| Ex. | Amount of the crude material (g) | Solvent Kind of solvent | Volumetric ratio | Amount (ml) | Stirring conditions T (° C.) | Time (hr) | Purity % | Yield % |
|---|---|---|---|---|---|---|---|---|
| 337 | 10 | distilled water | / | 400 | 70 | 30 | 98.8 | 48 |
| 338 | 10 | distilled water | / | 400 | 65 | 30 | 99.0 | 49 |
| 339 | 10 | distilled water | / | 400 | 60 | 30 | 98.9 | 52 |
| 340 | 10 | distilled water | / | 400 | 55 | 30 | 98.9 | 51 |
| 341 | 10 | distilled water | / | 400 | 80 | 30 | 99.1 | 55 |
| 342 | 10 | distilled water | / | 400 | 70 | 20 | 98.7 | 47 |
| 343 | 10 | distilled water | / | 400 | 70 | 25 | 98.6 | 46 |
| 344 | 10 | distilled water | / | 400 | 70 | 35 | 98.9 | 53 |
| 345 | 10 | distilled water | / | 400 | 65 | 25 | 99.1 | 58 |
| 346 | 10 | distilled water | / | 400 | 65 | 35 | 99.0 | 50 |
| 347 | 10 | distilled water | / | 400 | 65 | 20 | 99.1 | 50 |
| 348 | 10 | dimethyl sulfoxide:distilled water | 1:4 | 250 | 60 | 30 | 99.0 | 42 |
| 349 | 10 | dimethyl sulfoxide:distilled water | 1:4 | 250 | 70 | 30 | 99.2 | 43 |
| 350 | 10 | dimethyl sulfoxide:distilled water | 4:6 | 200 | 65 | 25 | 98.8 | 41 |
| 351 | 10 | dimethyl sulfoxide:distilled water | 6:4 | 200 | 75 | 25 | 98.8 | 47 |
| 352 | 10 | dimethyl sulfoxide:distilled water | 1:1 | 200 | 75 | 25 | 98.5 | 48 |
| 353 | 10 | dimethyl sulfoxide:distilled water | 8:2 | 200 | 75 | 25 | 98.4 | 56 |
| 354 | 10 | dimethyl sulfoxide:distilled water | 7:3 | 200 | 75 | 25 | 99.0 | 52 |

TABLE 5-continued

Preparation of the 3/4 hydrates (Examples 337~358)

| Ex. | Amount of the crude material (g) | Solvent Kind of solvent | Volumetric ratio | Amount (ml) | T (° C.) | Stirring conditions Time (hr) | Purity % | Yield % |
|---|---|---|---|---|---|---|---|---|
| 355 | 10 | dimethyl sulfoxide:distilled water | 3:7 | 200 | 75 | 25 | 99.1 | 55 |
| 356 | 10 | dimethyl sulfoxide:distilled water | 2:8 | 200 | 75 | 25 | 98.7 | 50 |
| 357 | 10 | dimethyl sulfoxide:distilled water | 1:9 | 200 | 75 | 25 | 98.5 | 54 |
| 358 | 10 | Tween-80:water | 1:3 | 200 | 75 | 25 | 98.4 | 58 |

EXAMPLE 359

In vitro Studies of Antibacterial Activity of (S)—[N-3-(3'-fluoro-4'-(4''-phenylpiperazinyl))phenyl-2-oxo-5-oxazolelidinyl]methylacetamide hydrates Hydrates Samples:
The 1/2 hydrates prepared according to Example 2;
Content (purity % wt): 99.0%;
The 1/12 hydrates prepared according to Example 253;
Content (purity % wt): 98.9%;
The 2/7 hydrates prepared according to Example 106;
Content (purity % wt): 98.8%;
The 2/5 hydrates prepared according to Example 162;
Content (purity % wt): 99.0%;
The 3/4 hydrates prepared according to Example 337;
Content (purity % wt): 98.8%;
Preparation: dissolved in DMSO, and further diluted with sterile distilled water to desired concentration.
The hydrates samples were supplied by Sichuan Beilike Biotechnology LTD.
Anhydrous Sample:
The anhydrous compounds prepared according to Example 1.
Content (purity % wt): 98.6%;
Preparation: dissolved in DMSO, and further diluted with sterile distilled water to desired concentration;
The anhydrous sample was supplied by Sichuan Beilike Biotechnology LTD.
Control Samples
Vancomycin: provided by Sichuan Beilike Biotechnology LTD, purchased from Eli Lilly Japan K.K.
Lot No.: WM16151 (production date: Apr. 10, 2007, expiration date: Apr. 9, 2009).
Specification: 500 mg/bottle; solubility (physicochemical properties): soluble in water.
Linezolid (LZ): provided by Sichuan Beilike Biotechnology LTD.
Bacteria Strains
Clinically isolated strains: clinically isolated bacterial pathogens collected in Sichuan and Beijing areas from March 2007 to May 2008.
Species include: *Staphylococcus aureus* MRSA, *Staphylococcus aureus* MSSA, *S. epidermidis* MRSE, *S. epidermidis* MSSE, *E. feacalis*, and *E. feacium*, a total of 51 strains.
Quality control strains: *Staphylococcus aureus* ATCC27853 strain kept in Sichuan Industrial Institute of Antibiotics, purchased from the medical testing center of the Ministry of Health, China.

Experimental Method:
Measurement of the minimum inhibitory concentration (MIC) in vitro:
The minimum inhibitory concentration (MIC) of each test sample against test strains was measured by using the agar dilution method recommended by the U.S. National Committee for Clinical Laboratory Standards (CLSI/NCCIs).
Results and Analysis
Based on the CLSI/NCCL's testing standard with respect to vancomycin and linezolid (see Table 6), the minimum inhibitory concentration (MIC) values of every strain were reported, and the $MIC_{50}$ (the concentration that inhibits 50% of the different strains of bacteria), $MIC_{90}$ (the concentration that inhibits 90% of the different strains of bacteria), and $MIC_{range}$ (the range of the MIC value of the tested strains) were observed.
The MIC values of the anhydrous compounds and the hydrates of the present disclosure are shown in Tables 7, 8, and 9.
The $MIC_{50}$, $MIC_{90}$, $MIC_{range}$ of the hydrates of the present disclosure against 51 strains of clincally isolated pathogens are shown in Table 9. The range of the MIC value of the above-mentioned sample against *Staphylococcus aureus* MRSA, MSSA; *S. epidermidis* MRSE, MSSE; and *E. feacalis, E. feacium* was within 0.06-4 ug/ml. See Table 9.

TABLE 6

Vancomycin and linezolid susceptibility (CILS/NCCLs 2007)

| Bacterium | Drug | Inhibition zone S | I | R | MIC (µg/ml) S | I | R | Remarks |
|---|---|---|---|---|---|---|---|---|
| | 1/2 hydrate | | | | — | — | — | No standard |
| | 2/7 hydrate | | | | — | — | — | No standard |
| | 2/5 hydrate | | | | — | — | — | No standard |
| | 1/12 hydrate | | | | — | — | — | No standard |
| | 3/4 hydrate | | | | — | — | — | No standard |
| For *S. aureus* | Vancomycin | | | | ≤2 | 4-8 | ≥16 | |
| | Linezolid | | | | ≤4 | — | — | |
| For *S. pneumoniae* | Vancomycin | | | | ≤1 | — | — | |
| | Linezolid | | | | ≤2 | — | — | |
| For *E. fae* activated Calis added | Vancomycin | | | | ≤4 | 8-16 | ≥32 | |
| | Linezolid | | | | ≤2 | 4 | ≥8 | |

TABLE 7

The MIC values of the hydrates of the present disclosure (MIC ug/ml)

| No. | Test strains (No. of bacterium) | Anhydrous | 1/2 hydrate | 2/7 hydrate | 2/5 hydrate | 1/12 hydrate | 3/4 hydrate | Vancomycin | Linezolid | Bacterium control |
|---|---|---|---|---|---|---|---|---|---|---|
| 1 | S. AT C C25923 | 2 | 0.25 | 0.5 | 0.5 | 0.5 | 1 | 1 | 2 | + |
| 2 | S. MSSA 232 | 2 | 0.25 | 0.5 | 0.5 | 0.5 | 1 | 0.5 | 2 | + |
| 3 | S. MSSA 123 | 2 | 0.25 | 0.5 | 0.5 | 0.5 | 1 | 0.5 | 2 | + |
| 4 | S. MSSA 520 | 2 | 0.25 | 0.25 | 0.5 | 0.5 | 1 | 0.5 | 2 | + |
| 5 | S. MSSA 580 | 2 | 0.25 | 0.25 | 0.5 | 0.25 | 1 | 1 | 2 | + |
| 6 | S. MSSA 195 | 2 | 0.5 | 1 | 1 | 0.5 | 1 | 1 | 2 | + |
| 7 | S. MSSA 187 | 2 | 0.25 | 0.5 | 0.5 | 0.5 | 1 | 0.5 | 2 | + |
| 8 | S. MSSA 466 | 1 | 0.25 | 0.5 | 0.5 | 0.25 | 0.5 | 0.5 | 1 | + |
| 9 | S. MSSA 519 | 2 | 0.5 | 0.5 | 0.5 | 0.5 | 1 | 1 | 2 | + |
| 10 | S. MSSA 275 | 1 | 0.25 | 0.5 | 0.5 | 1 | 0.5 | 1 | 2 | + |
| 11 | S. MSSA 201 | 1 | 0.25 | 0.5 | 0.5 | 0.25 | 0.5 | 1 | 2 | + |
| 12 | S. MSSA 195 | 1 | 0.25 | 0.5 | 0.5 | 0.5 | 1 | 1 | 2 | + |
| 13 | S. MRSA 201 | 2 | 0.5 | 0.5 | 0.5 | 0.5 | 1 | 1 | 2 | + |
| 14 | S. MRSA 101 | 2 | 0.5 | 1 | 0.5 | 0.5 | 1 | 0.5 | 1 | + |
| 15 | S. MRSA 29 | 2 | 0.25 | 0.5 | 0.5 | 1 | 0.5 | 0.5 | 1 | + |
| 16 | S. MRSA B164 | 1 | 0.25 | 0.5 | 0.5 | 0.5 | 1 | 1 | 2 | + |
| 17 | S. MRSA B105 | 2 | 0.25 | 0.5 | 0.5 | 0.5 | 1 | 1 | 2 | + |
| 18 | S. MRSA B617 | 2 | 0.25 | 0.5 | 0.5 | 0.25 | 1 | 05 | 1 | + |
| 19 | S. MRSA B143 | 2 | 0.25 | 0.5 | 0.5 | 0.5 | 1 | 0.5 | 1 | + |
| 20 | S. MRSA B151 | 2 | 0.25 | 0.5 | 0.25 | 0.5 | 1 | 1 | 2 | + |
| 21 | S. MRSA B27 | 1 | 0.25 | 0.5 | 0.5 | 0.5 | 0.5 | 1 | 2 | + |
| 22 | S. MRSA B199 | 1 | 0.25 | 0.5 | 0.5 | 1 | 0.5 | 1 | 2 | + |
| 23 | S. ep MSSE87 | 1 | 0.06 | 0.125 | 0.125 | 0.125 | 0.5 | 0.125 | 0.5 | + |
| 24 | S. ep MSSE113 | 1 | 0.25 | 0.25 | 0.5 | 0.25 | 0.5 | 0.5 | 1 | + |
| 25 | S. ep MSSE116 | 1 | 0.25 | 0.25 | 0.5 | 0.125 | 0.5 | 0.125 | 0.5 | + |
| 26 | S. ep MSSE142 | 2 | 0.125 | 0.5 | 0.25 | 0.5 | 1 | 0.06 | 1 | + |
| 27 | S. ep MSSE119 | 2 | 0.25 | 0.25 | 0.125 | 0.125 | 1 | 0.125 | 1 | + |

TABLE 8

The MIC values of the hydrates of the present disclosure (MIC ug/ml)

| No. | Test strains (No. of bacterium) | Anhydrous compound | 1/2 hydrate | 2/7 hydrate | 2/5 hydrate | 1/12 hydrate | 3/4 hydrate | Vancomycin | Linezolid | Bacterium control |
|---|---|---|---|---|---|---|---|---|---|---|
| 1 | S. ep MSSE153 | 2 | 0.25 | 0.5 | 0.5 | 0.5 | 1 | 0.5 | 1 | + |
| 2 | S. ep MSSE118 | 1 | 0.25 | 0.5 | 0.5 | 0.5 | 0.5 | 1 | 2 | + |
| 3 | S. ep MSSE140 | 1 | 0.25 | 0.5 | 0.5 | 0.5 | 0.5 | 0.5 | 2 | + |
| 4 | S. ep MSSE137 | 2 | 0.25 | 0.5 | 0.5 | 0.5 | 1 | 1 | 2 | + |
| 5 | S. ep MSSE88 | 2 | 0.25 | 0.5 | 0.5 | 0.5 | 1 | 1 | 2 | + |
| 6 | S. ep MRSE20 | 2 | 0.25 | 0.5 | 0.5 | 0.25 | 1 | 1 | 1 | + |
| 7 | S. ep MRSE101 | 2 | 0.25 | 0.25 | 0.125 | 0.06 | 1 | 1 | 0.5 | + |
| 8 | S. ep MRSE211 | 2 | 0.25 | 0.5 | 0.5 | 0.25 | 1 | 0.5 | 1 | + |
| 9 | S. ep MRSE4 | 2 | 0.25 | 0.25 | 0.5 | 0.125 | 1 | 1 | 1 | + |
| 10 | S. ep MRSE90 | 2 | 0.25 | 0.5 | 0.5 | 0.125 | 1 | 1 | 2 | + |
| 11 | S. ep MRSE105 | 2 | 0.25 | 0.5 | 0.5 | 0.25 | 1 | 0.5 | 1 | + |
| 12 | S. ep MRSE142 | 2 | 0.25 | 0.5 | 0.5 | 0.25 | 1 | 0.5 | 1 | + |
| 13 | S. ep MRSE87 | 2 | 0.25 | 0.5 | 0.5 | 0.25 | 1 | 0.25 | 2 | + |
| 14 | S. ep MRSE140 | 2 | 0.25 | 0.5 | 0.5 | 0.5 | 1 | 1 | 1 | + |
| 15 | S. ep MRSE210 | 2 | 0.25 | 0.5 | 0.5 | 0.25 | 1 | 1 | 1 | + |
| 16 | Efa 116 | 4 | 0.25 | 0.5 | 0.5 | 0.25 | 2 | 0.5 | 1 | + |
| 17 | Efa 33748 | 8 | 0.25 | 0.5 | 0.5 | 0.125 | 4 | 0.25 | 2 | + |
| 18 | Efa 3006 | 4 | 0.06 | 0.25 | 0.25 | 0.125 | 2 | 2 | 1 | + |
| 19 | Efa 907 | 2 | 0.125 | 0.25 | 0.5 | 0.06 | 1 | 1 | 1 | + |
| 20 | Efa 54 | 4 | 0.06 | 0.125 | 0.125 | 0.125 | 2 | 1 | 1 | + |
| 21 | Efm 98 | 4 | 0.25 | 0.5 | 0.5 | 0.25 | 2 | 4 | 2 | + |
| 22 | Efm 197 | 2 | 0.5 | 0.5 | 1 | 0.5 | 1 | 4 | 2 | + |
| 23 | Efm N3 | 8 | 0.5 | 1 | 1 | 1 | 4 | 2 | 1 | + |
| 24 | Efm N4 | 8 | 1 | 1 | 1 | 0.5 | 4 | 8 | 4 | + |
| 25 | Efm 171 | 4 | 0.25 | 1 | 0.5 | 0.5 | 2 | 8 | 2 | + |

TABLE 9

The $MIC_{50}$, $MIC_{90}$, $MIC_{range}$ of the hydrates of the present disclosure against 51 strains of clincally isolated pathogens (ug/ml)

| Test strains (Numbers) | | Anhydrous compound | 1/2 hydrate | 2/7 hydrate | 2/5 hydrate | 1/12 hydrate | 3/4 hydrate | Vancomycin | Linezolid |
|---|---|---|---|---|---|---|---|---|---|
| S. MSSA (11) | $MIC_{50}$ | 2 | 0.25 | 0.5 | 0.5 | 0.5 | 1 | 1 | 2 |
| | $MIC_{90}$ | 2 | 0.25 | 0.5 | 0.5 | 0.5 | 1 | 1 | 2 |
| | $MIC_{range}$ | 1-2 | 0.25-0.5 | 0.5-1 | 0.5-1 | 0.25-0.5 | 0.5-1 | 0.5-1 | 1-2 |
| S. MRSA (10) | $MIC_{50}$ | 2 | 0.25 | 0.5 | 1 | 0.5 | 1 | 1 | 2 |
| | $MIC_{90}$ | 2 | 0.25 | 0.5 | 0.5 | 0.5 | 1 | 1 | 2 |
| | $MIC_{range}$ | 1-2 | 0.25-0.5 | 0.5-1 | 0.25-0.5 | 0.25-0.5 | 0.5-1 | 0.5-1 | 1-2 |
| S. ep MSSE (10) | $MIC_{50}$ | 1 | 0.25 | 0.5 | 0.5 | 0.25 | 0.5 | 0.5 | 1 |
| | $MIC_{90}$ | 2 | 0.25 | 0.5 | 0.5 | 0.5 | 1 | 1 | 2 |
| | $MIC_{range}$ | 1-2 | 0.06-0.25 | 0.25-0.5 | 0.125-0.5 | 0.125-0.5 | 0.5-1 | 0.06-1 | 0.5-2 |
| S. ep MRSE (10) | $MIC_{50}$ | 2 | 0.25 | 0.5 | 0.5 | 0.25 | 1 | 1 | 1 |
| | $MIC_{90}$ | 2 | 0.25 | 0.5 | 0.5 | 0.5 | 1 | 1 | 2 |
| | $MIC_{range}$ | 2 | 0.25 | 0.25-0.5 | 0.125-0.5 | 0.06-0.5 | 1 | 0.25-1 | 0.5-2 |
| E. feacalis (5) | $MIC_{50}$ | 4 | 0.125 | 0.25 | 0.5 | 0.125 | 2 | 1 | 1 |
| | $MIC_{90}$ | 8 | 0.25 | 0.5 | 0.5 | 0.25 | 4 | 2 | 2 |
| | $MIC_{range}$ | 2-8 | 0.06-0.25 | 0.125-0.5 | 0.125-0.5 | 0.06-0.25 | 1-4 | 0.25-2 | 1-2 |
| E. feacium (5) | $MIC_{50}$ | 4 | 0.5 | 1 | 1 | 0.5 | 2 | 4 | 2 |
| | $MIC_{90}$ | 8 | 1 | 1 | 1 | 1 | 4 | 8 | 4 |
| | $MIC_{range}$ | 2-8 | 0.25-1 | 0.5-1 | 0.5-1 | 0.25-1 | 1-4 | 2-8 | 1-4 |

EXAMPLE 360

The Stability and Solubility Test Results of the (S)—[N-3-(3'-fluoro-4'-(4"-phenylpiperazinyl))phenyl-2-oxo-5-oxazolelidinyl]methylacetamide hydrates of the Present Disclosure In order to further evaluate the effect of temperature, humidity and light on the quality of the crystalline compounds of the present disclosure, the hydrates were placed in a dessicator with a relative humidity of 75% and at a constant temperature of 40° C. The samples were then collected at 1, 2, 3, and 6 months. Results are shown in Tables 10-14, wherein the "related substances" mean all of the ingredients in a sample except the active material. The content of the related substances in a sample was measure by HPLC in accordance to the Chinese Pharmacopeia (2005 edition, Part II, Appendix V D).

TABLE 10

The ½ hydrate under high temperature and high humidity

| Time (Month) | Characters | TGA (%) | Related substances (%) |
|---|---|---|---|
| 0 | White powder | 2.14 | 0.90 |
| 1 | White powder | 2.15 | 0.88 |
| 2 | White powder | 2.16 | 0.92 |
| 3 | White powder | 2.20 | 0.90 |
| 6 | White powder | 2.10 | 0.94 |

TABLE 11

The 2/7 hydrate under high temperature and high humidity

| Time (Month) | Characters | TGA (%) | Related substances (%) |
|---|---|---|---|
| 0 | White powder | 1.20 | 0.91 |
| 1 | White powder | 1.21 | 0.89 |
| 2 | White powder | 1.19 | 0.90 |
| 3 | White powder | 1.23 | 0.91 |
| 6 | White powder | 1.21 | 0.95 |

TABLE 12

The 2/5 hydrate under high temperature and high humidity

| Time (Month) | Characters | TGA (%) | Related substances (%) |
|---|---|---|---|
| 0 | White powder | 1.71 | 0.93 |
| 1 | White powder | 1.73 | 0.89 |
| 2 | White powder | 1.70 | 0.91 |
| 3 | White powder | 1.72 | 0.93 |
| 6 | White powder | 1.72 | 0.92 |

TABLE 13

The 1/12 hydrate under high temperature and high humidity

| Time (Month) | Characters | TGA (%) | Related substances (%) |
|---|---|---|---|
| 0 | White powder | 0.40 | 0.94 |
| 1 | White powder | 0.38 | 0.88 |
| 2 | White powder | 0.39 | 0.90 |
| 3 | White powder | 0.40 | 0.92 |
| 6 | White powder | 0.42 | 0.93 |

TABLE 14

The 3/4 hydrate under high temperature and high humidity

| Time (Month) | Characters | TGA (%) | Related substances (%) |
|---|---|---|---|
| 0 | White powder | 3.10 | 0.94 |
| 1 | White powder | 3.11 | 0.88 |
| 2 | White powder | 3.10 | 0.90 |
| 3 | White powder | 3.09 | 0.92 |
| 6 | White powder | 3.10 | 0.93 |

The results above show that hydrates of the present disclosure at a relative humidity of 75% and at a constant temperature of 40° C. for 6 months were stable in comparison with the original state (i.e., 0 month). The related substances of hydrates of the present disclosure did not substantially change, and thus hydrates of the present disclosure could be used as pharmaceuticals.

The solubility of the (S)—[N-3-(3'-fluoro-4'-(4"-phenylpiperazinyl))phenyl-2-oxo-5-oxazolelidinyl]methylacetamide hydrates was tested with different solvents, and the test results are shown in Tables 15-19. The solubility was measured according to Chinese Pharmacopeia (2005 edition). The results show that the 1/2 hydrate, 1/12 hydrate, 3/4 hydrate, 2/7 hydrate, 2/5 hydrate of (S)—[N-3-(3'-fluoro-4'-(4"-phenylpiperazinyl))phenyl-2-oxo-5-oxazolelidinyl]methylacetamide are sometimes more soluble than the anhydride.

TABLE 15

The comparison of solubility of the ½ hydrate disclosed herein and anhydride

| Solvent | Name | Solute:Solvent (g:ml) | Result | Conclusion |
|---|---|---|---|---|
| Ethanol | Anhydride | 1:2000 | Dissolved | Very little dissolved |
| | ½ hydrate | 1:900 | Dissolved | Slightly soluble |
| Methanol | Anhydride | 1:1500 | Dissolved | Very little dissolved |
| | ½ hydrate | 1:600 | Dissolved | Slightly soluble |
| 0.1N Hydrochloric acid | Anhydride | 1:300 | Dissolved | Slightly soluble |
| | ½ hydrate | 1:100 | Dissolved | Little soluble |
| Acetonitrile | Anhydride | 1:800 | Dissolved | Slightly soluble |
| | ½ hydrate | 1:400 | Dissolved | Slightly soluble |
| Water | Anhydride | 1:10000 | Insoluble | Almost insoluble |
| | ½ hydrate | 1:5000 | Dissolved | Very little dissolved |
| 0.1N Sodium hydroxide | Anhydride | 1:10000 | Insoluble | Almost insoluble |
| | ½ hydrate | 1:10000 | Insoluble | Almost insoluble |

TABLE 16

The comparison of solubility of the ⅖ hydrate disclosed herein and anhydride

| Solvent | Name | Solute:Solvent (g:ml) | Result | Conclusion |
|---|---|---|---|---|
| Ethanol | Anhydride | 1:2000 | Dissolved | Very little dissolved |
| | ⅖ hydrate | 1:900 | Dissolved | Slightly soluble |
| Methanol | Anhydride | 1:1500 | Dissolved | Very little dissolved |
| | ⅖ hydrate | 1:600 | Dissolved | Slightly soluble |
| 0.1N Hydrochloric acid | Anhydride | 1:300 | Dissolved | Slightly soluble |
| | ⅖ hydrate | 1:100 | Dissolved | Little soluble |
| Acetonitrile | Anhydride | 1:800 | Dissolved | Slightly soluble |
| | ⅖ hydrate | 1:400 | Dissolved | Slightly soluble |
| Water | Anhydride | 1:10000 | Insoluble | Almost insoluble |
| | ⅖ hydrate | 1:5000 | Dissolved | Very little dissolved |
| 0.1N Sodium hydroxide | Anhydride | 1:10000 | Insoluble | Almost insoluble |
| | ⅖ hydrate | 1:10000 | Insoluble | Almost insoluble |

TABLE 17

The comparison of solubility of the ¾ hydrate disclosed herein and anhydride

| Solvent | Name | Solute:Solvent (g:ml) | Result | Conclusion |
|---|---|---|---|---|
| Ethanol | Anhydride | 1:2000 | Dissolved | Very little dissolved |
| | ¾ hydrate | 1:850 | Dissolved | Slightly soluble |
| Methanol | Anhydride | 1:1500 | Dissolved | Very little dissolved |
| | ¾ hydrate | 1:600 | Dissolved | Slightly soluble |
| 0.1N Hydrochloric acid | Anhydride | 1:300 | Dissolved | Slightly soluble |
| | ¾ hydrate | 1:90 | Dissolved | Little soluble |
| Acetonitrile | Anhydride | 1:800 | Dissolved | Slightly soluble |
| | ¾ hydrate | 1:400 | Dissolved | Slightly soluble |
| Water | Anhydride | 1:10000 | Insoluble | Almost insoluble |
| | ¾ hydrate | 1:5000 | Dissolved | Very little dissolved |
| 0.1N Sodium hydroxide | Anhydride | 1:10000 | Insoluble | Almost insoluble |
| | ¾ hydrate | 1:10000 | Insoluble | Almost insoluble |

TABLE 18

The comparison of solubility of the 2/7 hydrate disclosed herein and anhydride

| Solvent | Name | Solute:Solvent (g:ml) | Result | Conclusion |
|---|---|---|---|---|
| Ethanol | Anhydride | 1:2000 | Dissolved | Very little dissolved |
| | 2/7 hydrate | 1:950 | Dissolved | Slightly soluble |
| Methanol | Anhydride | 1:1500 | Dissolved | Very little dissolved |
| | 2/7 hydrate | 1:700 | Dissolved | Slightly soluble |
| 0.1N Hydrochloric acid | Anhydride | 1:300 | Dissolved | Slightly soluble |
| | 2/7 hydrate | 1:200 | Dissolved | Little soluble |
| Acetonitrile | Anhydride | 1:800 | Dissolved | Slightly soluble |
| | 2/7 hydrate | 1:500 | Dissolved | Slightly soluble |
| Water | Anhydride | 1:10000 | Insoluble | Almost insoluble |
| | 2/7 hydrate | 1:5000 | Dissolved | Very little dissolved |
| 0.1N Sodium hydroxide | Anhydride | 1:10000 | Insoluble | Almost insoluble |
| | 2/7 hydrate | 1:10000 | Insoluble | Almost insoluble |

TABLE 19

The comparison of solubility of the 1/12 hydrate disclosed herein and anhydride

| Solvent | Name | Solute:Solvent (g:ml) | Result | Conclusion |
|---|---|---|---|---|
| Ethanol | Anhydride | 1:2200 | Dissolved | Very little dissolved |
| | 1/12 hydrate | 1:950 | Dissolved | Slightly soluble |
| Methanol | Anhydride | 1:1400 | Dissolved | Very little dissolved |
| | 1/12 hydrate | 1:700 | Dissolved | Slightly soluble |
| 0.1N Hydrochloric acid | Anhydride | 1:350 | Dissolved | Slightly soluble |
| | 1/12 hydrate | 1:150 | Dissolved | Little soluble |
| Acetonitrile | Anhydride | 1:830 | Dissolved | Slightly soluble |
| | 1/12 hydrate | 1:420 | Dissolved | Slightly soluble |
| Water | Anhydride | 1:10800 | Insoluble | Almost insoluble |
| | 1/12 hydrate | 1:5400 | Dissolved | Very little dissolved |
| 0.1N Sodium hydroxide | Anhydride | 1:10200 | Insoluble | Almost insoluble |
| | 1/12 hydrate | 1:9800 | Insoluble | Almost insoluble |

As those skilled in the art will appreciate, numerous changes and modifications may be made to the embodiments of the disclosure without departing from the spirit of the disclosure. It is intended that all such variations fall within the scope of the disclosure.

What is claimed is:

1. At least one crystalline hydrate of (S)—[N-3-(3'-fluoro-4'-(4"-phenyl piperazinyl))phenyl-2-oxo-5-oxazolidinyl]methyl acetamide, with the following formula:

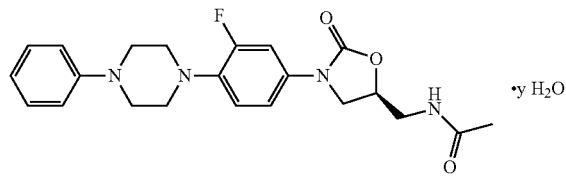 [SMILES: CC(=O)NC[C@H]1CN(c2ccc(N3CCN(c4ccccc4)CC3)c(F)c2)C(=O)O1]

·y H$_2$O wherein y is a number ranging from 1/12 to 1.

2. The at least one crystalline hydrate of claim 1 being at least 99% free of crystalline hydrates of (R)—[N-3-(3'-fluoro-4'-(4"-phenyl piperazinyl))phenyl-2-oxo-5-oxazolidinyl]methyl acetamide.

3. The at least one crystalline hydrate of claim 1 being at least 95% free of crystalline hydrates of (R)—[N-3-(3'-fluoro-4'-(4"-phenyl piperazinyl))phenyl-2-oxo-5-oxazolidinyl]methyl acetamide.

4. The at least one crystalline hydrate of claim 1 being at least 90% free of crystalline hydrates of (R)—[N-3-(3'-fluoro-4'-(4"-phenyl piperazinyl))phenyl-2-oxo-5-oxazolidinyl]methyl acetamide.

5. The at least one crystalline hydrate of claim 1 being at least 80% free of crystalline hydrates of (R)—[N-3-(3'-fluoro-4'-(4"-phenyl piperazinyl))phenyl-2-oxo-5-oxazolidinyl]methyl acetamide.

6. The at least one crystalline hydrate of claim 1 being at least 70% free of crystalline hydrates of (R)—[N-3-(3'-fluoro-4'-(4"-phenyl piperazinyl))phenyl-2-oxo-5-oxazolidinyl]methyl acetamide.

7. The at least one crystalline hydrate of claim 1 being at least 60% free of crystalline hydrates of (R)—[N-3-(3'-fluoro-4'-(4"-phenyl piperazinyl))phenyl-2-oxo-5-oxazolidinyl]methyl acetamide.

8. The at least one crystalline hydrate of claim 1 being more than at least 50% free of crystalline hydrates of (R)—[N-3-(3'-fluoro-4'-(4"-phenyl piperazinyl)) phenyl-2-oxo-5-oxazolidinyl]methyl acetamide.

9. The at least one crystalline hydrate of claim 1, wherein said at least one crystalline hydrate comprises no more than about 50% by weight of any other solid state form(s).

10. The at least one crystalline hydrate of claim 9, wherein said at least one crystalline hydrate comprises no more than about 10% by weight of any other polymorphic solid state form(s).

11. The at least one crystalline hydrate of claim 10, wherein said at least one crystalline hydrate comprises no more than about 5% by weight of any other polymorphic solid state form(s).

12. The at least one crystalline hydrate of claim 11, wherein said at least one crystalline hydrate comprises no more than about 1% by weight of any other polymorphic solid state form(s).

13. The at least one crystalline hydrate of claim 1, wherein y is chosen from 1/12, 2/7, 2/5, 1/2, and 3/4.

14. The at least one crystalline hydrate of claim 13 being at least 99% free of crystalline hydrates of (R)—[N-3-(3'-fluoro-4'-(4"-phenyl piperazinyl))phenyl-2-oxo-5-oxazolidinyl]methyl acetamide.

15. The at least one crystalline hydrate of claim 13 being at least 95% free of crystalline hydrates of (R)—[N-3-(3'-fluoro-4'-(4"-phenyl piperazinyl))phenyl-2-oxo-5-oxazolidinyl]methyl acetamide.

16. The at least one crystalline hydrate of claim 13 being at least 90% free of crystalline hydrates of (R)—[N-3-(3'-fluoro-4'-(4"-phenyl piperazinyl))phenyl-2-oxo-5-oxazolidinyl]methyl acetamide.

17. The at least one crystalline hydrate of claim 13 being at least 80% free of crystalline hydrates of (R)—[N-3-(3'-fluoro-4'-(4"-phenyl piperazinyl))phenyl-2-oxo-5-oxazolidinyl]methyl acetamide.

18. The at least one crystalline hydrate of claim 13 being at least 70% free of crystalline hydrates of (R)—[N-3-(3'-fluoro-4'-(4"-phenyl piperazinyl))phenyl-2-oxo-5-oxazolidinyl]methyl acetamide.

19. The at least one crystalline hydrate of claim 13 being at least 60% free of crystalline hydrates of (R)—[N-3-(3'-fluoro-4'-(4"-phenyl piperazinyl))phenyl-2-oxo-5-oxazolidinyl]methyl acetamide.

20. The at least one crystalline hydrate of claim 13 being more than at least 50% free of crystalline hydrates of (R)—[N-3-(3'-fluoro-4'-(4"-phenyl piperazinyl)) phenyl-2-oxo-5-oxazolidinyl]methyl acetamide.

21. The at least one crystalline hydrate of claim 1, wherein said at least one crystalline hydrate has a chemical purity of greater than about 95%.

22. The at least one crystalline hydrate of claim 21, wherein said at least one crystalline hydrate has a chemical purity of greater than about 98%.

23. The at least one crystalline hydrate of claim 22, wherein said at least one crystalline hydrate has a chemical purity of greater than about 99%.

24. A method for preparing at least one crystalline (S)—[N-3-(3'-fluoro-4'-(4"-phenyl piperazinyl))phenyl-2-oxo-5-oxazolidinyl]methyl acetamide hydrate according to claim 1, comprising:

forming a solution of (S)—[N-3-(3'-fluoro-4'-(4"-phenyl piperazinyl))phenyl-2-oxo-5-oxazolidinyl]methyl acetamide by dissolving (S)—[N-3-(3'-fluoro-4'-(4"-phenyl piperazinyl))phenyl-2-oxo-5-oxazolidinyl]methyl acetamide with at least one suitable solvent;
stirring the solution at an appropriate temperature; and
crystallizing at least one (S)—[N-3-(3'-fluoro-4'-(4"-phenyl piperazinyl))phenyl-2-oxo-5-oxazolidinyl]methyl acetamide hydrate from the solution.

25. A method for preparing at least one crystalline (S)—[N-3-(3'-fluoro-4'-(4"-phenyl piperazinyl))phenyl-2-oxo-5-oxazolidinyl]methyl acetamide hydrate according to claim 1, comprising:
forming a solution of (S)—[N-3-(3'-fluoro-4'-(4"-phenyl piperazinyl))phenyl-2-oxo-5-oxazolidinyl]methyl acetamide by dissolving (S)—[N-3-(3'-fluoro-4'-(4"-phenyl piperazinyl))phenyl-2-oxo-5-oxazolidinyl]methyl acetamide with at least one suitable solvent chosen from water, nonacidic organic solvents, and acidic solvents;
stirring the solution at a temperature ranging from 30° C. to 90° C.; and
crystallizing at least one (S)—[N-3-(3'-fluoro-4'-(4"-phenyl piperazinyl))phenyl-2-oxo-5-oxazolidinyl]methyl acetamide hydrate from the solution.

26. The method of claim 25, further comprising filtering the solution after the stirring operation.

27. The method of claim 25, further comprising adding activated carbon to said solution.

28. The method of claim 25, wherein crystallizing said at least one (S)—[N-3-(3'-fluoro-4'-(4"-phenyl piperazinyl))phenyl-2-oxo-5-oxazolidinyl]methyl acetamide hydrate from said solution comprises pouring the solution into a second solvent or adding the second solvent to the solution, wherein the second solvent does not dissolve (S)—[N-3-(3'-fluoro-4'-(4"-phenyl piperazinyl))phenyl-2-oxo-5-oxazolidinyl]methyl acetamide.

29. The method of claim 25, wherein the at least one suitable solvent comprises at least one acidic solvent having a pH value of less than or equal to 5, and wherein the at least one acidic solvent is chosen from hydrochloric acid, sulfuric acid, phosphoric acid, citric acid, acetic acid, permanganic acid, perchloric acid, hydrobromic acid, nitric acid, formic acid, tartaric acid, benzoic acid, phenylacetic acid, maleic acid, oxalic acid, trifluoroacetic acid, and dichloroacetic acid.

30. The method of claim 25, where the at least one suitable solvent further comprises at least one nonacidic organic solvent chosen from ethanol, methanol acetonitrile, ethyl acetate, tetrahydrofuran, and petroleum ether, and wherein the at least one acidic solvent and the at least one nonacidic organic solvent are mixed at a volumetric ratio ranging from 1:9 to 9:1.

31. The method of claim 25, wherein the at least one suitable solvent is a mixed solvent comprising at least one acidic solvent having a pH value ranging from 2 to 5, and at least one nonacidic organic solvent; wherein:
the at least one acidic solvent and the at least one nonacidic organic solvent are mixed at a volumetric ratio ranging from 1:9 to 9:1;
the at least one acidic solvent is chosen from hypophosphorous acid, metaphosphoric acid, meta-aluminic acid, lactic acid, and succinic acid; and
the at least one nonacidic organic solvent is chosen from propanol, glycol, n-butanol, and N,N-dimethylformamide.

32. The method of claim 25, wherein the at least one suitable solvent is a mixed solvent comprising water and at least one nonacidic organic solvent chosen from methyl acetate, ethyl acetate, propyl acetate, phenyl acetate, heptyl acetate, decyl acetate, isobutyl acetate, and glycol diacetate; and wherein the water and the at least one nonacidic organic solvent are mixed at a volumetric ratio ranging from 1:9 to 9:1.

33. The method of claim 25, wherein the at least one suitable solvent is a mixed solvent comprising water and at least one nonacidic organic solvent, wherein the at least one nonacidic organic solvent is chosen from methanol, ethanol, acetonitrile, 1,2-propylene glycol, isopropanol, n-propanol, s-butanol, isobutanol, and ethylene glycol; and wherein the water and the at least one nonacidic organic solvent are mixed at a volumetric ratio ranging from 1:9 to 9:1.

34. The method of claim 25, wherein the at least one suitable solvent is a mixed solvent comprising water and at least one nonacidic organic solvent, wherein the at least one nonacidic organic solvent is chosen from dimethyl sulfoxide and Tween-80, and wherein the water and the at least one nonacidic organic solvent are mixed at a volumetric ratio ranging from 1:9 to 9:1.

35. The method of claim 25, wherein the at least one suitable solvent is water.

36. The method of claim 25, wherein the solution is stirred at a temperature ranging from 35 to 70° C.

37. The method of claim 25, wherein the solution is stirred for at least one hour.

38. The method of claim 37, wherein the solution is stirred for a period of time ranging from 1 to 10 hours.

39. The method of claim 38, wherein the solution is stirred for a period of time ranging from 1 to 5 hours.

40. At least one crystalline hydrate of (S)—[N-3-(3'-fluoro-4'-(4"-phenyl piperazinyl))phenyl-2-oxo-5-oxazolidinyl]methyl acetamide according to claim 1 prepared from:
forming a solution of (S)—[N-3-(3'-fluoro-4'-(4"-phenyl piperazinyl))phenyl-2-oxo-5-oxazolidinyl]methyl acetamide by dissolving (S)—[N-3-(3'-fluoro-4'-(4"-phenyl piperazinyl))phenyl-2-oxo-5-oxazolidinyl]methyl acetamide with at least one suitable solvent chosen from water, nonacidic organic solvents, and acidic solvents;
stirring the solution at an appropriate temperature; and
crystallizing at least one (S)—[N-3-(3'-fluoro-4'-(4"-phenyl piperazinyl))phenyl-2-oxo-5-oxazolidinyl] methyl acetamide hydrate from the solution.

41. A mixture comprising (S)—[N-3-(3'-fluoro-4'-(4"-phenyl piperazinyl))phenyl-2-oxo-5-oxazolidinyl]methyl acetamide and at least one crystalline hydrate of (S)—[N-3-(3'-fluoro-4'-(4"-phenyl piperazinyl))phenyl-2-oxo-5-oxazolidinyl]methyl acetamide according to claim 1, wherein the at least one crystalline hydrate is at least 90% free of crystalline hydrates of (R)—[N-3-(3'-fluoro-4'-(4"-phenyl piperazinyl)) phenyl-2-oxo-5-oxazolidinyl]methyl acetamide.

42. The mixture of claim 1, wherein in the formula, y is chosen from 1/12, 2/7, 2/5, 1/2, and 3/4.

43. At least one crystalline hydrate comprising:

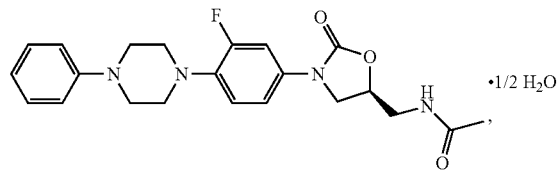 [SMILES: CC(=O)NC[C@H]1CN(c2ccc(N3CCN(c4ccccc4)CC3)c(F)c2)C(=O)O1]

wherein the at least one crystalline hydrate is at least 90% free of crystalline hydrates of (R)—[N-3-(3'-fluoro-4'-(4"-phenyl piperazinyl))phenyl-2-oxo-5-oxazolidinyl]methyl acetamide.

44. At least one crystalline hydrate comprising:

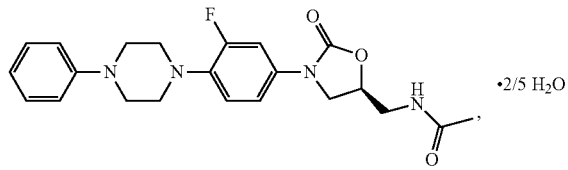 [SMILES: CC(=O)NC[C@H]1CN(c2ccc(N3CCN(c4ccccc4)CC3)c(F)c2)C(=O)O1]

·2/5 H₂O, wherein the at least one crystalline hydrate is at least 90% free of crystalline hydrates of (R)—[N-3-(3'-fluoro-4'-(4"-phenyl piperazinyl))phenyl-2-oxo-5-oxazolidinyl]methyl acetamide.

45. At least one crystalline hydrate comprising:

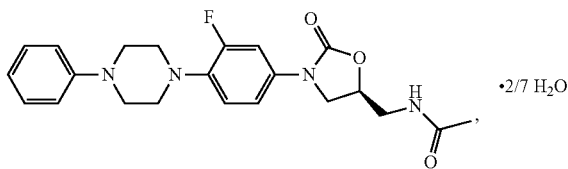 [SMILES: CC(=O)NC[C@H]1CN(c2ccc(N3CCN(c4ccccc4)CC3)c(F)c2)C(=O)O1]

·2/7 H₂O, wherein the at least one crystalline hydrate is at least 90% free of crystalline hydrates of (R)—[N-3-(3'-fluoro-4'-(4"-phenyl piperazinyl))phenyl-2-oxo-5-oxazolidinyl]methyl acetamide.

46. At least one crystalline hydrate comprising:

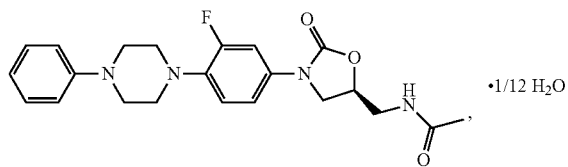 [SMILES: CC(=O)NC[C@H]1CN(c2ccc(N3CCN(c4ccccc4)CC3)c(F)c2)C(=O)O1]

·1/12 H₂O, wherein the at least one crystalline hydrate is at least 90% free of crystalline hydrates of (R)—[N-3-(3'-fluoro-4'-(4"-phenyl piperazinyl))phenyl-2-oxo-5-oxazolidinyl]methyl acetamide.

47. At least one crystalline hydrate comprising:

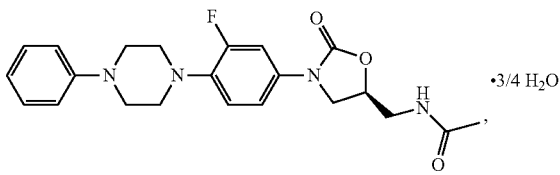 [SMILES: CC(=O)NC[C@H]1CN(c2ccc(N3CCN(c4ccccc4)CC3)c(F)c2)C(=O)O1]

·3/4 H₂O, wherein the at least one crystalline hydrate is at least 90% free of crystalline hydrates of (R)—[N-3-(3'-fluoro-4'-(4"-phenyl piperazinyl))phenyl-2-oxo-5-oxazolidinyl]methyl acetamide.

48. A pharmaceutical composition comprising:
a therapeutically effective amount of at least one crystalline hydrate of (S)—[N-3-(3'-fluoro-4'-(4"-phenyl piperazinyl))phenyl-2-oxo-5-oxazolidinyl]methyl acetamide according to claim 1, wherein the at least one crystalline hydrate is at least 90% free of crystalline hydrates of (R)—[N-3-(3'-fluoro-4'-(4"-phenyl piperazinyl))phenyl-2-oxo-5-oxazolidinyl]methyl acetamide; and
at least one ingredient chosen from pharmaceutically acceptable diluents and excipients.

49. A method of treating a subject having a gram positive bacterial infection and in recognized need of treatment therefor comprising administering to said subject in recognized need of treatment an effective amount of at least one crystalline hydrate of (S)—[N-3-(3'-fluoro-4'-(4"-phenyl piperazinyl))phenyl-2-oxo-5-oxazolidinyl]methyl acetamide according to claim 1, wherein the at least one crystalline hydrate is at least 90% free of crystalline hydrates of (R)—[N-3-(3'-fluoro-4'-(4"-phenyl piperazinyl))phenyl-2-oxo-5-oxazolidinyl]methyl acetamide, to treat said bacterial infection.

50. A method of treating a subject having a gram positive bacterial infection and in recognized need of treatment therefor comprising
administering to said subject in recognized need of treatment an effective amount of a pharmaceutical composition comprising:
at least one crystalline hydrate of (S)—[N-3-(3'-fluoro-4'-(4"-phenyl piperazinyl))phenyl-2-oxo-5-oxazolidinyl]methyl acetamide according to claim 1, wherein the at least one crystalline hydrate is at least 90% free of crystalline hydrates of (R)—[N-3-(3'-fluoro-4'-(4"-phenyl piperazinyl))phenyl-2-oxo-5-oxazolidinyl]methyl acetamide; and
at least one pharmaceutically acceptable diluents and/or carrier to provide said treatment.

\* \* \* \* \*